(12) United States Patent
McGoldrick et al.

(10) Patent No.: US 11,992,198 B2
(45) Date of Patent: May 28, 2024

(54) ARTERIOTOMY CLOSURE APPARATUS WITH SLOTTED SHOE FOR ADVANTAGEOUS PRESSURE DISTRIBUTION

(71) Applicant: Vivasure Medical Limited, Galway (IE)

(72) Inventors: Mark McGoldrick, Athlone (IE); Noelle Barrett, Knocknacarra (IE); Christopher Martin, Oughterard (IE); Peter Grant, Galway (IE); Bartosz Pawlikowski, Moycullen (IE); Gerard Brett, Claregalway (IE)

(73) Assignee: Vivasure Medical Limited, Galway (IE)

( * ) Notice: Subject to any disclaimer, the term of this patent is extended or adjusted under 35 U.S.C. 154(b) by 112 days.

(21) Appl. No.: 17/697,279

(22) Filed: Mar. 17, 2022

(65) Prior Publication Data

US 2022/0218322 A1    Jul. 14, 2022

Related U.S. Application Data

(63) Continuation of application No. 16/061,028, filed as application No. PCT/EP2016/081183 on Dec. 15, 2016, now Pat. No. 11,311,280.

(Continued)

(51) Int. Cl.
*A61B 17/00* (2006.01)

(52) U.S. Cl.
CPC ............ *A61B 17/0057* (2013.01); *A61B 2017/00004* (2013.01); *A61B 2017/00477* (2013.01);

(Continued)

(58) Field of Classification Search
CPC ........... A61B 2017/00575; A61B 2017/00615; A61B 17/0057; A61B 2017/00659;

(Continued)

(56) References Cited

U.S. PATENT DOCUMENTS

| 321,721 A | 7/1885 | Hassan |
|---|---|---|
| 2,001,638 A | 5/1935 | Tornsjo |

(Continued)

FOREIGN PATENT DOCUMENTS

| CN | 101400308 A | 4/2009 |
|---|---|---|
| CN | 104287803 A | 1/2015 |

(Continued)

OTHER PUBLICATIONS

U.S. Appl. No. 62/092,212, filed Dec. 15, 2014, McGoldrick et al.

(Continued)

*Primary Examiner* — Diane D Yabut
*Assistant Examiner* — Christina C Lauer
(74) *Attorney, Agent, or Firm* — Choate, Hall & Stewart LLP; Peter A. Flynn; Qing Hua Wang

(57) ABSTRACT

The disclosed technology provides a device for sealing an aperture in a tissue of a body lumen. The device comprises a flexible support member having a base having (i) a central portion and (ii) one or more lateral support portions, to engage and/or hold a sealable member of the device against an interior surface of the tissue when the device is in the sealing position. The lateral support portions provide additional support surfaces to engage peripheral portions of the sealable member against the interior surface of the tissue. A cage or shoe engaged with the support member on the exterior surface of the tissue can provide additional support and assist sealing the aperture.

20 Claims, 86 Drawing Sheets

Related U.S. Application Data

(60) Provisional application No. 62/267,644, filed on Dec. 15, 2015.

(52) U.S. Cl.
CPC ............ *A61B 2017/0053* (2013.01); *A61B 2017/00654* (2013.01); *A61B 2017/00659* (2013.01)

(58) Field of Classification Search
CPC ........... A61B 2017/00654; A61B 2017/00004; A61B 2017/0053; A61B 2017/00606; A61B 2017/00477
See application file for complete search history.

(56) References Cited

U.S. PATENT DOCUMENTS

| | | |
|---|---|---|
| 2,560,162 A | 7/1951 | Ferguson |
| 2,778,254 A | 1/1957 | Carapellotti |
| 3,874,388 A | 4/1975 | King et al. |
| 4,299,230 A | 11/1981 | Kubota |
| 4,583,540 A | 4/1986 | Malmin |
| 4,650,472 A | 3/1987 | Bates |
| 4,705,040 A | 11/1987 | Mueller et al. |
| 4,744,364 A | 5/1988 | Kensey |
| 4,852,568 A | 8/1989 | Kensey |
| 4,890,612 A | 1/1990 | Kensey |
| 4,896,668 A | 1/1990 | Popoff et al. |
| 5,021,059 A | 6/1991 | Kensey et al. |
| 5,037,433 A | 8/1991 | Wilk et al. |
| 5,053,046 A | 10/1991 | Janese |
| 5,085,661 A | 2/1992 | Moss |
| 5,127,412 A | 7/1992 | Cosmetto et al. |
| 5,171,258 A | 12/1992 | Bales et al. |
| 5,192,301 A | 3/1993 | Kamiya et al. |
| 5,269,804 A | 12/1993 | Bales et al. |
| 5,282,827 A | 2/1994 | Kensey et al. |
| 5,320,461 A | 6/1994 | Stanesic |
| 5,330,488 A | 7/1994 | Goldrath |
| 5,336,231 A | 8/1994 | Adair |
| 5,342,393 A | 8/1994 | Stack |
| 5,350,399 A | 9/1994 | Erlebacher et al. |
| 5,366,480 A | 11/1994 | Corriveau et al. |
| 5,391,182 A | 2/1995 | Chin |
| 5,431,639 A | 7/1995 | Shaw |
| 5,462,560 A | 10/1995 | Stevens |
| 5,470,337 A | 11/1995 | Moss |
| 5,501,691 A | 3/1996 | Goldrath |
| 5,501,700 A | 3/1996 | Hirata |
| 5,507,755 A | 4/1996 | Gresl et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,593,422 A | 1/1997 | Muijs Van de Moer et al. |
| 5,601,557 A | 2/1997 | Hayhurst |
| 5,601,571 A | 2/1997 | Moss |
| 5,620,461 A | 4/1997 | Muijs Van De Moer et al. |
| 5,653,716 A | 8/1997 | Malo et al. |
| 5,662,681 A | 9/1997 | Nash et al. |
| 5,665,096 A | 9/1997 | Yoon |
| 5,676,689 A | 10/1997 | Kensey et al. |
| 5,690,674 A | 11/1997 | Diaz |
| 5,700,273 A | 12/1997 | Buelna et al. |
| 5,700,277 A | 12/1997 | Nash et al. |
| 5,707,393 A | 1/1998 | Kensey et al. |
| 5,722,981 A | 3/1998 | Stevens |
| 5,755,727 A | 5/1998 | Kontos |
| 5,782,861 A | 7/1998 | Cragg et al. |
| 5,797,939 A | 8/1998 | Yoon |
| 5,814,065 A | 9/1998 | Diaz |
| 5,817,074 A | 10/1998 | Racz |
| 5,827,281 A | 10/1998 | Levin |
| 5,860,990 A | 1/1999 | Nobles et al. |
| 5,861,003 A | 1/1999 | Latson et al. |
| 5,868,762 A | 2/1999 | Cragg et al. |
| 5,916,236 A | 6/1999 | Muijs Van de Moer et al. |
| 5,935,147 A | 8/1999 | Kensey et al. |
| 5,941,899 A | 8/1999 | Granger et al. |
| 5,954,732 A | 9/1999 | Hart et al. |
| 5,997,515 A | 12/1999 | de la Torre et al. |
| 6,007,563 A | 12/1999 | Nash et al. |
| 6,033,427 A | 3/2000 | Lee |
| 6,056,768 A | 5/2000 | Cates et al. |
| 6,080,183 A | 6/2000 | Tsugita et al. |
| 6,126,675 A | 10/2000 | Shchervinsky et al. |
| 6,136,010 A | 10/2000 | Modesitt et al. |
| 6,179,863 B1 | 1/2001 | Kensey et al. |
| 6,190,400 B1 | 2/2001 | Van De Moer et al. |
| 6,200,328 B1 | 3/2001 | Cragg et al. |
| 6,206,895 B1 | 3/2001 | Levinson |
| 6,241,768 B1 | 6/2001 | Agarwal et al. |
| 6,245,080 B1 | 6/2001 | Levinson |
| 6,296,658 B1 | 10/2001 | Gershony et al. |
| 6,319,263 B1 | 11/2001 | Levinson |
| 6,350,274 B1 | 2/2002 | Li |
| 6,375,671 B1 | 4/2002 | Kobayashi et al. |
| 6,383,208 B1 | 5/2002 | Sancoff et al. |
| 6,395,015 B1 | 5/2002 | Borst et al. |
| 6,398,796 B2 | 6/2002 | Levinson |
| 6,425,911 B1 | 7/2002 | Akerfeldt et al. |
| 6,461,364 B1 | 10/2002 | Ginn et al. |
| 6,485,481 B1 | 11/2002 | Pfeiffer |
| 6,500,184 B1 | 12/2002 | Chan et al. |
| 6,508,828 B1 | 1/2003 | Akerfeldt et al. |
| 6,520,951 B1 | 2/2003 | Carrillo, Jr. et al. |
| 6,596,012 B2 | 7/2003 | Akerfeldt et al. |
| 6,596,014 B2 | 7/2003 | Levinson et al. |
| 6,596,915 B1 | 7/2003 | Satyapal et al. |
| 6,638,286 B1 | 10/2003 | Burbank et al. |
| 6,669,707 B1 | 12/2003 | Swanstrom et al. |
| 6,669,735 B1 | 12/2003 | Pelissier |
| 6,702,835 B2 | 3/2004 | Ginn |
| 6,730,112 B2 | 5/2004 | Levinson |
| 6,764,500 B1 | 7/2004 | Muijs Van De Moer et al. |
| 6,770,070 B1 | 8/2004 | Balbierz |
| 6,779,701 B2 | 8/2004 | Bailly et al. |
| 6,786,915 B2 | 9/2004 | Akerfeldt et al. |
| 6,860,895 B1 | 3/2005 | Akerfeldt et al. |
| 6,890,342 B2 | 5/2005 | Zhu et al. |
| 6,932,824 B1 | 8/2005 | Roop et al. |
| 6,939,363 B2 | 9/2005 | Akerfeldt |
| 6,942,674 B2 | 9/2005 | Belef et al. |
| 6,949,107 B2 | 9/2005 | McGuckin, Jr. et al. |
| 6,949,114 B2 | 9/2005 | Milo et al. |
| 6,964,668 B2 | 11/2005 | Modesitt et al. |
| 6,969,397 B2 | 11/2005 | Ginn |
| 6,984,219 B2 | 1/2006 | Ashby et al. |
| 6,989,022 B2 | 1/2006 | Nowakowski |
| 6,997,940 B2 | 2/2006 | Bonutti |
| 7,001,398 B2 | 2/2006 | Carley et al. |
| 7,001,400 B1 | 2/2006 | Modesitt et al. |
| 7,008,440 B2 | 3/2006 | Sing et al. |
| 7,008,441 B2 | 3/2006 | Zucker |
| 7,008,442 B2 | 3/2006 | Brightbill |
| 7,094,248 B2 | 8/2006 | Bachinski et al. |
| 7,144,411 B2 | 12/2006 | Ginn et al. |
| 7,169,168 B2 | 1/2007 | Muijs Van De Moer et al. |
| 7,326,221 B2 | 2/2008 | Sakamoto et al. |
| 7,462,188 B2 | 12/2008 | McIntosh |
| 7,534,248 B2 | 5/2009 | Mikkaichi et al. |
| 7,569,063 B2 | 8/2009 | Bailly et al. |
| 7,662,161 B2 | 2/2010 | Briganti et al. |
| 7,678,133 B2 | 3/2010 | Modesitt |
| 7,753,935 B2 | 7/2010 | Brett et al. |
| 7,846,180 B2 | 12/2010 | Cerier |
| 7,850,710 B2 | 12/2010 | Huss |
| 7,918,868 B2 | 4/2011 | Marshall et al. |
| 7,998,169 B2 | 8/2011 | Modesitt |
| 8,002,791 B2 | 8/2011 | Modesitt |
| 8,002,792 B2 | 8/2011 | Modesitt |
| 8,002,793 B2 | 8/2011 | Modesitt |
| 8,012,168 B2 | 9/2011 | Modesitt |

(56) References Cited

U.S. PATENT DOCUMENTS

| | | |
|---|---|---|
| 8,083,767 B2 | 12/2011 | Modesitt |
| 8,137,380 B2 | 3/2012 | Green et al. |
| 8,177,795 B2 | 5/2012 | Niese et al. |
| 8,241,325 B2 | 8/2012 | Modesitt |
| 8,267,942 B2 | 9/2012 | Szabo et al. |
| 8,361,092 B1 | 1/2013 | Asfora |
| 8,529,431 B2 | 9/2013 | Baker et al. |
| 8,597,324 B2 | 12/2013 | Briganti et al. |
| 8,652,166 B2 | 2/2014 | Åkerfeldt |
| 8,821,507 B2 | 9/2014 | Axelson, Jr. et al. |
| 8,906,050 B2 | 12/2014 | Brett et al. |
| 9,060,751 B2 | 6/2015 | Martin et al. |
| 9,610,070 B2 | 4/2017 | Martin |
| 9,850,013 B2 | 12/2017 | Grant et al. |
| 10,206,668 B2 | 2/2019 | McGoldrick et al. |
| 10,307,145 B2 | 6/2019 | Shipp |
| 10,314,727 B2 | 6/2019 | Liu et al. |
| 10,433,826 B2 | 10/2019 | Grant et al. |
| 11,141,142 B2 | 10/2021 | McGoldrick et al. |
| 11,311,280 B2 | 4/2022 | McGoldrick et al. |
| 11,357,486 B2 | 6/2022 | Martin et al. |
| 2001/0044631 A1 | 11/2001 | Akin et al. |
| 2002/0019648 A1 | 2/2002 | Akerfeldt et al. |
| 2002/0019649 A1 | 2/2002 | Sikora et al. |
| 2002/0055767 A1 | 5/2002 | Forde et al. |
| 2002/0107506 A1 | 8/2002 | McGuckin et al. |
| 2002/0169377 A1 | 11/2002 | Khairkhahan et al. |
| 2002/0177864 A1 | 11/2002 | Camrud |
| 2002/0198562 A1 | 12/2002 | Akerfeldt et al. |
| 2003/0050665 A1 | 3/2003 | Ginn |
| 2003/0060846 A1 | 3/2003 | Egnelov et al. |
| 2003/0078598 A1 | 4/2003 | Ginn et al. |
| 2003/0093093 A1 | 5/2003 | Modesitt et al. |
| 2003/0120305 A1 | 6/2003 | Jud et al. |
| 2003/0144695 A1 | 7/2003 | McGuckin et al. |
| 2003/0216756 A1 | 11/2003 | Klein et al. |
| 2004/0082906 A1 | 4/2004 | Tallarida et al. |
| 2004/0092964 A1 | 5/2004 | Modesitt et al. |
| 2004/0092969 A1 | 5/2004 | Kumar |
| 2004/0093025 A1 | 5/2004 | Egnelov |
| 2004/0098044 A1 | 5/2004 | Van de Moer et al. |
| 2004/0133238 A1 | 7/2004 | Cerier |
| 2004/0176798 A1 | 9/2004 | Epstein et al. |
| 2004/0243122 A1 | 12/2004 | Auth et al. |
| 2005/0021055 A1 | 1/2005 | Toubia et al. |
| 2005/0021059 A1 | 1/2005 | Cole et al. |
| 2005/0033326 A1 | 2/2005 | Briganti et al. |
| 2005/0070957 A1 | 3/2005 | Das |
| 2005/0143817 A1 | 6/2005 | Hunter et al. |
| 2005/0149065 A1 | 7/2005 | Modesitt |
| 2005/0181008 A1 | 8/2005 | Hunter et al. |
| 2005/0209613 A1 | 9/2005 | Roop et al. |
| 2005/0251201 A1 | 11/2005 | Roue et al. |
| 2005/0267520 A1 | 12/2005 | Modesitt |
| 2005/0273135 A1 | 12/2005 | Chanduszko et al. |
| 2005/0288706 A1 | 12/2005 | Widomski et al. |
| 2006/0100665 A1 | 5/2006 | Von Oepen et al. |
| 2006/0106418 A1 | 5/2006 | Seibold et al. |
| 2006/0142784 A1 | 6/2006 | Kontos |
| 2006/0142797 A1 | 6/2006 | Egnelov |
| 2006/0265008 A1 | 11/2006 | Maruyama et al. |
| 2006/0287673 A1 | 12/2006 | Brett et al. |
| 2007/0112385 A1 | 5/2007 | Conlon |
| 2007/0135826 A1 | 6/2007 | Zaver et al. |
| 2007/0179509 A1 | 8/2007 | Nagata et al. |
| 2007/0179527 A1 | 8/2007 | Eskuri et al. |
| 2007/0197858 A1 | 8/2007 | Goldfarb et al. |
| 2007/0255313 A1 | 11/2007 | Modesitt |
| 2007/0282351 A1 | 12/2007 | Harada et al. |
| 2007/0282373 A1 | 12/2007 | Ashby et al. |
| 2008/0004689 A1 | 1/2008 | Jahnke et al. |
| 2008/0109017 A1 | 5/2008 | Herweck et al. |
| 2008/0228204 A1 | 9/2008 | Hamilton et al. |
| 2008/0243148 A1 | 10/2008 | Mikkaichi et al. |
| 2008/0312646 A9 | 12/2008 | Auth et al. |
| 2009/0012521 A1 | 1/2009 | Axelson, Jr. et al. |
| 2009/0018574 A1 | 1/2009 | Martin |
| 2009/0048559 A1 | 2/2009 | Grathwohl |
| 2009/0088723 A1 | 4/2009 | Khosravi et al. |
| 2009/0112257 A1 | 4/2009 | Preinitz et al. |
| 2009/0143815 A1 | 6/2009 | Eidenschink et al. |
| 2009/0143821 A1 | 6/2009 | Stupak |
| 2009/0312786 A1 | 12/2009 | Trask et al. |
| 2009/0319017 A1 | 12/2009 | Berez et al. |
| 2010/0022823 A1 | 1/2010 | Goldfarb et al. |
| 2010/0094425 A1 | 4/2010 | Bentley et al. |
| 2010/0114159 A1 | 5/2010 | Roorda et al. |
| 2010/0125296 A1 | 5/2010 | Modesitt |
| 2010/0152772 A1 | 6/2010 | Brett et al. |
| 2010/0222796 A1 | 9/2010 | Brett et al. |
| 2010/0228184 A1 | 9/2010 | Mavani et al. |
| 2010/0292717 A1 | 11/2010 | Petter-Puchner et al. |
| 2011/0077667 A1 | 3/2011 | Singhatat et al. |
| 2011/0082495 A1 | 4/2011 | Ruiz |
| 2011/0087270 A1 | 4/2011 | Penner et al. |
| 2011/0224728 A1 | 9/2011 | Martin et al. |
| 2011/0270284 A1 | 11/2011 | Beauchamp et al. |
| 2012/0059399 A1 | 3/2012 | Hoke et al. |
| 2012/0089166 A1 | 4/2012 | Modesitt |
| 2012/0165957 A1 | 6/2012 | Everland et al. |
| 2012/0226308 A1 | 9/2012 | Martin et al. |
| 2012/0226309 A1 | 9/2012 | Jonsson |
| 2012/0296275 A1 | 11/2012 | Martin et al. |
| 2012/0302987 A1 | 11/2012 | Jonsson |
| 2013/0116799 A1 | 5/2013 | Derwin et al. |
| 2013/0218125 A1 | 8/2013 | Stopek et al. |
| 2013/0218201 A1 | 8/2013 | Obermiller et al. |
| 2013/0274795 A1* | 10/2013 | Grant .............. A61B 50/30 606/213 |
| 2014/0018846 A1 | 1/2014 | Grant et al. |
| 2014/0018847 A1 | 1/2014 | Grant et al. |
| 2014/0058439 A1 | 2/2014 | White |
| 2014/0180314 A1 | 6/2014 | Asfora |
| 2014/0194926 A1 | 7/2014 | Bailly et al. |
| 2014/0200597 A1* | 7/2014 | Klein .............. A61B 17/10 606/142 |
| 2014/0207183 A1 | 7/2014 | Shipp |
| 2014/0277113 A1 | 9/2014 | Stanley et al. |
| 2014/0345109 A1 | 11/2014 | Grant et al. |
| 2015/0045818 A1 | 2/2015 | Kim et al. |
| 2016/0051239 A1 | 2/2016 | Martin et al. |
| 2016/0166241 A1 | 6/2016 | McGoldrick et al. |
| 2017/0181736 A1 | 6/2017 | McGoldrick et al. |
| 2017/0281142 A1 | 10/2017 | Martin et al. |
| 2019/0021710 A1 | 1/2019 | McGoldrick et al. |
| 2020/0138421 A1 | 5/2020 | Grant et al. |
| 2022/0218323 A1 | 7/2022 | Martin et al. |
| 2023/0000477 A1 | 1/2023 | Grant et al. |
| 2023/0157679 A1 | 5/2023 | Walters et al. |
| 2023/0165578 A1 | 6/2023 | Walters et al. |

FOREIGN PATENT DOCUMENTS

| | | |
|---|---|---|
| CN | 104771200 A | 7/2015 |
| CN | 105073064 A | 11/2015 |
| DE | 19711288 B4 | 11/2004 |
| DE | 102010048908 A1 | 4/2012 |
| DE | 102013101338 A1 | 8/2014 |
| EP | 0551198 | 7/1993 |
| EP | 0761250 A1 | 3/1997 |
| EP | 0894475 A1 | 2/1999 |
| EP | 1 046 375 A1 | 10/2000 |
| EP | 1879505 B1 | 1/2008 |
| EP | 2260770 A2 | 12/2010 |
| EP | 2 292 147 A1 | 3/2011 |
| EP | 2 628 592 A1 | 8/2013 |
| EP | 2 777 543 A1 | 9/2014 |
| EP | 4190248 A1 | 6/2023 |
| WO | WO-1994/008513 A1 | 4/1994 |
| WO | WO-00/07520 A1 | 2/2000 |
| WO | WO-2000/033744 A1 | 6/2000 |
| WO | WO-2002/102236 A2 | 12/2002 |
| WO | WO-2004/012601 A2 | 2/2004 |
| WO | WO-2004/012603 A2 | 2/2004 |

(56) References Cited

FOREIGN PATENT DOCUMENTS

| WO | WO-2004/012627 A1 | 2/2004 |
|---|---|---|
| WO | WO-2006/117766 A2 | 11/2006 |
| WO | WO-2007/011353 A2 | 1/2007 |
| WO | WO-2007/057933 A1 | 5/2007 |
| WO | WO-2007/089603 A2 | 8/2007 |
| WO | WO-2008/042229 A2 | 4/2008 |
| WO | WO-2008/152617 A2 | 12/2008 |
| WO | WO-2009/070651 A1 | 6/2009 |
| WO | WO-2009/149455 A1 | 12/2009 |
| WO | WO-2010/027693 A2 | 3/2010 |
| WO | WO-2010/123821 A1 | 10/2010 |
| WO | WO-2011/080588 A2 | 7/2011 |
| WO | WO-2012/090069 A2 | 7/2012 |
| WO | WO-2012/156819 A2 | 11/2012 |
| WO | WO-2013/007534 A1 | 1/2013 |
| WO | WO-2013/128292 A2 | 9/2013 |
| WO | WO-2013/188351 A2 | 12/2013 |
| WO | WO-2014/140325 A1 | 9/2014 |
| WO | WO-2014/141209 A1 | 9/2014 |
| WO | WO-2014/149642 A2 | 9/2014 |
| WO | WO-2016/096930 A1 | 6/2016 |
| WO | WO-2016/096932 A1 | 6/2016 |
| WO | WO-2017/102941 A1 | 6/2017 |

OTHER PUBLICATIONS

U.S. Appl. No. 62/092,235, filed Dec. 15, 2014, Grant et al.
U.S. Appl. No. 62/092,240, filed Dec. 15, 2014, Grant et al.
European Patent Office Partial Supplementary Search Report. Application No. 12784868.7, dated Jan. 12, 2015, 5 pages.
Extended European Search Report, Application No. EP 11852355.4, dated Sep. 28, 2015, 7 pages.
Grant, et al., Hales' 1733 Haemastaticks, Anesthesiology, 112(1) (2010).
Hales, Stephen, Statical Essays, vol. 2 (1773).
International Preliminary Report on Patentability, PCT/IB2010/003461, dated Jul. 12, 2012, 10 pages.
International Preliminary Report on Patentability, PCT/IE2006/000043, dated Oct. 30, 2007, 10 pages.
International Search Report, PCT/EP2015/079904, 7 pages, dated Mar. 1, 2016.
International Search Report, PCT/EP2015/079906 (Closure Apparatus With Flexible Sealable Member and Flexible Support Member, filed Dec. 15, 2015), 7 pages, dated May 24, 2016.
International Search Report, PCT/EP2016/081183, 5 pages, dated Mar. 20, 2017.
International Search Report, PCT/IB2010/003461, dated Oct. 11, 2011, 6 pages.
International Search Report, PCT/IB2011/003295, dated Jun. 29, 2012, 4 pages.
International Search Report, PCT/IB2012/001101, dated Jan. 30, 2013, 3 pages.
International Search Report, PCT/IB2013/000839, dated Jan. 14, 2014, 6 pages.
International Search Report, PCT/IB2014/059848, dated Jul. 7, 2014, 5 pages.
Office Action for U.S. Appl. No. 12/982,852, 13 pages (dated Feb. 13, 2014).
Office Action for U.S. Appl. No. 13/473,483, 7 pages (dated Aug. 13, 2014).
Written Opinion, PCT/EP2015/079904, 8 pages, dated Mar. 1, 2016.
Written Opinion, PCT/EP2015/079906 (Closure Apparatus With Flexible Sealable Member and Flexible Support Member, filed Dec. 15, 2015), 11 pages, dated May 24, 2016.
Written Opinion, PCT/EP2016/081183, 12 pages, dated Mar. 20, 2017.
Written Opinion, PCT/IB2010/003461, dated Oct. 11, 2011, 9 pages.
Written Opinion, PCT/IB2011/003295, dated Jun. 29, 2012, 5 pages.
Written Opinion, PCT/IB2012/001101, dated Jan. 30, 2013, 5 pages.
Written Opinion, PCT/IB2013/000839, dated Jan. 14, 2014, 11 pages.
Written Opinion, PCT/IB2014/059848, dated Jul. 7, 2014, 8 pages.
Written Opinion, PCT/IE2006/000043, dated Oct. 29, 2007, 9 pages.

* cited by examiner

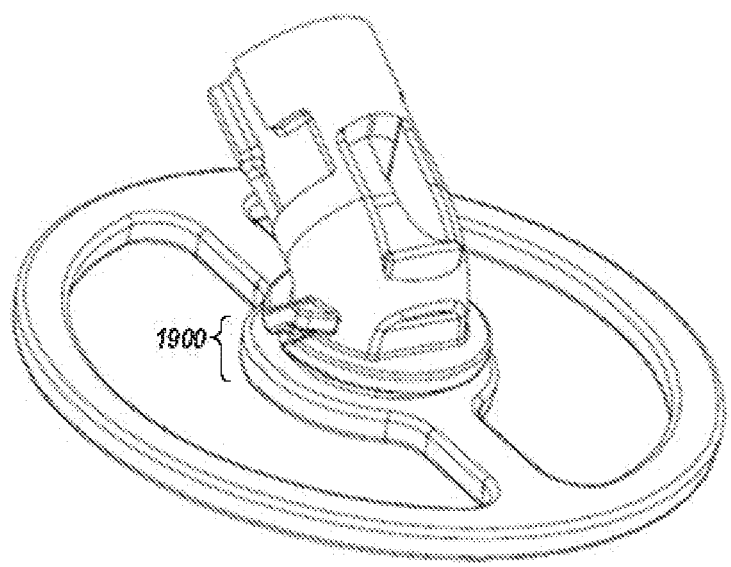
FIG. 19A
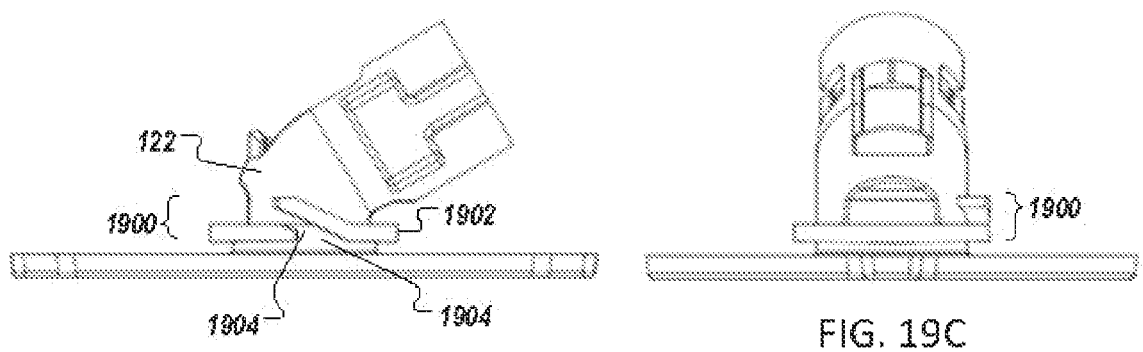
FIG. 19B
FIG. 19C

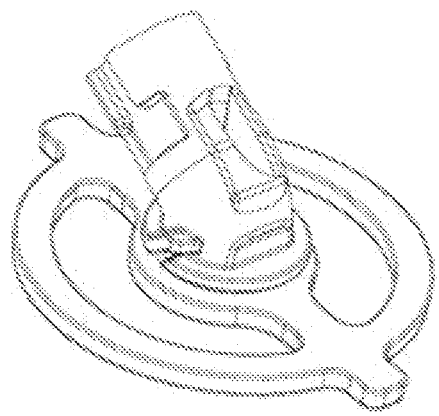
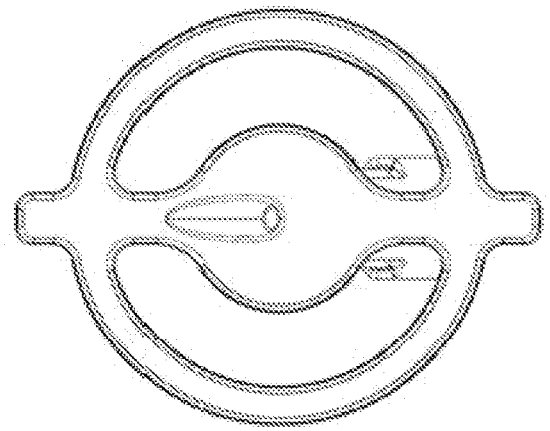
FIG. 32A
FIG. 32B
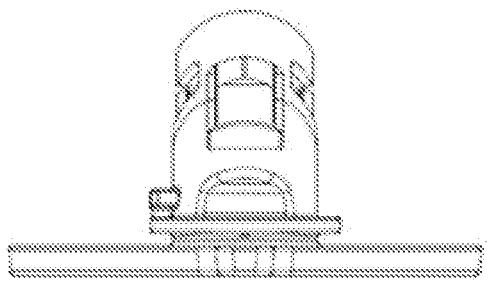
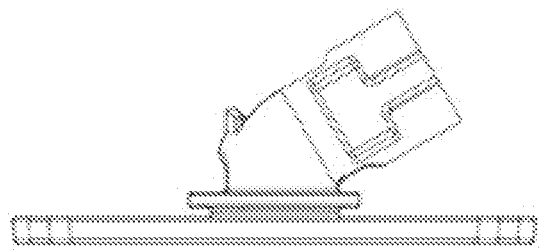
FIG. 32C
FIG. 32D

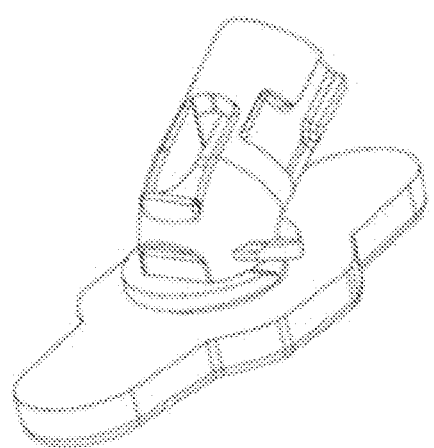
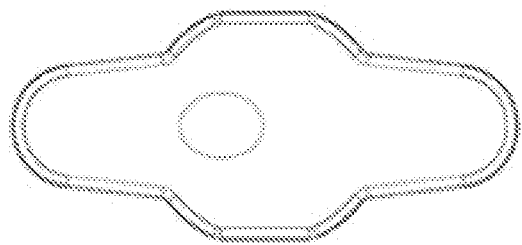
FIG. 45A  FIG. 45B
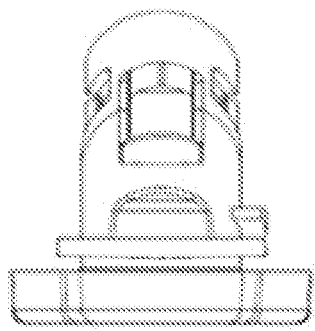
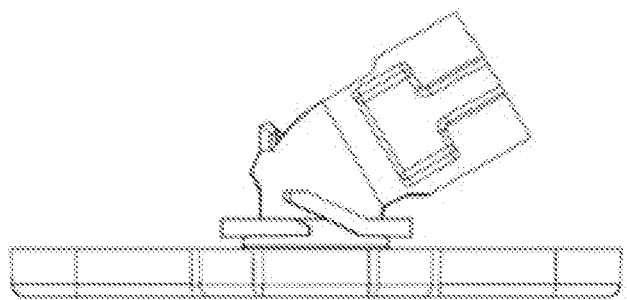
FIG. 45C  FIG. 45D

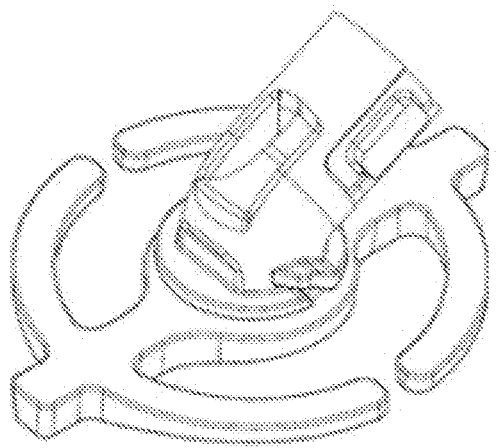
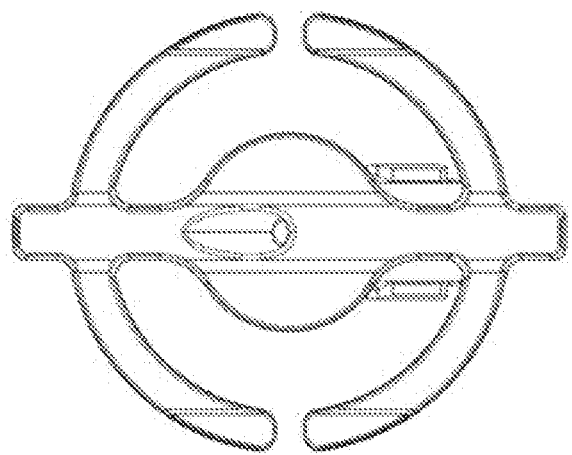
FIG. 61A
FIG. 61B
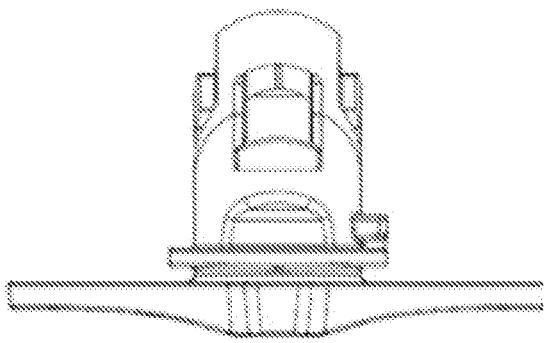
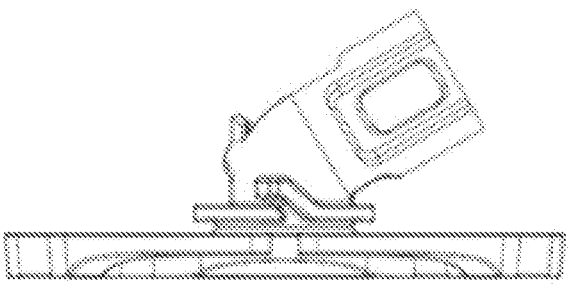
FIG. 61C
FIG. 61D

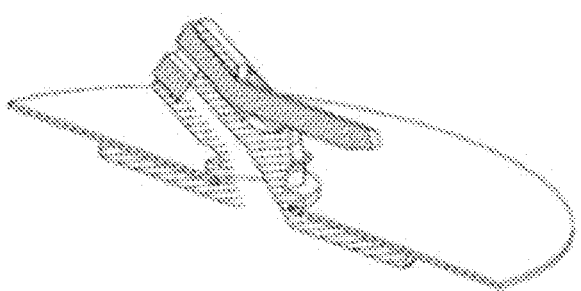
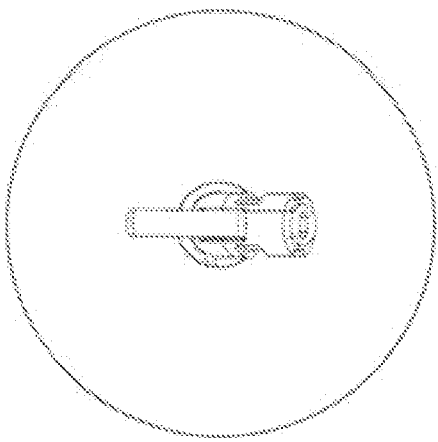
FIG. 69A
FIG. 69B
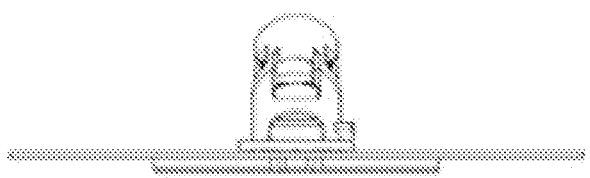
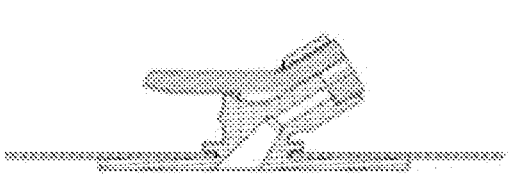
FIG. 69C
FIG. 69D

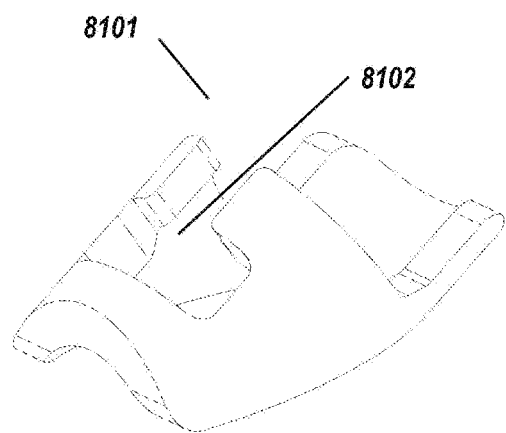 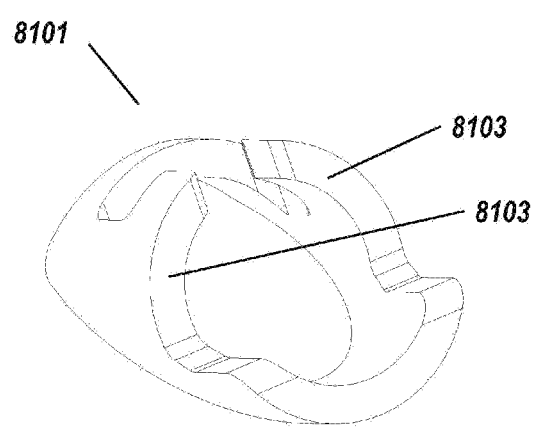
FIG. 81A  FIG. 81B
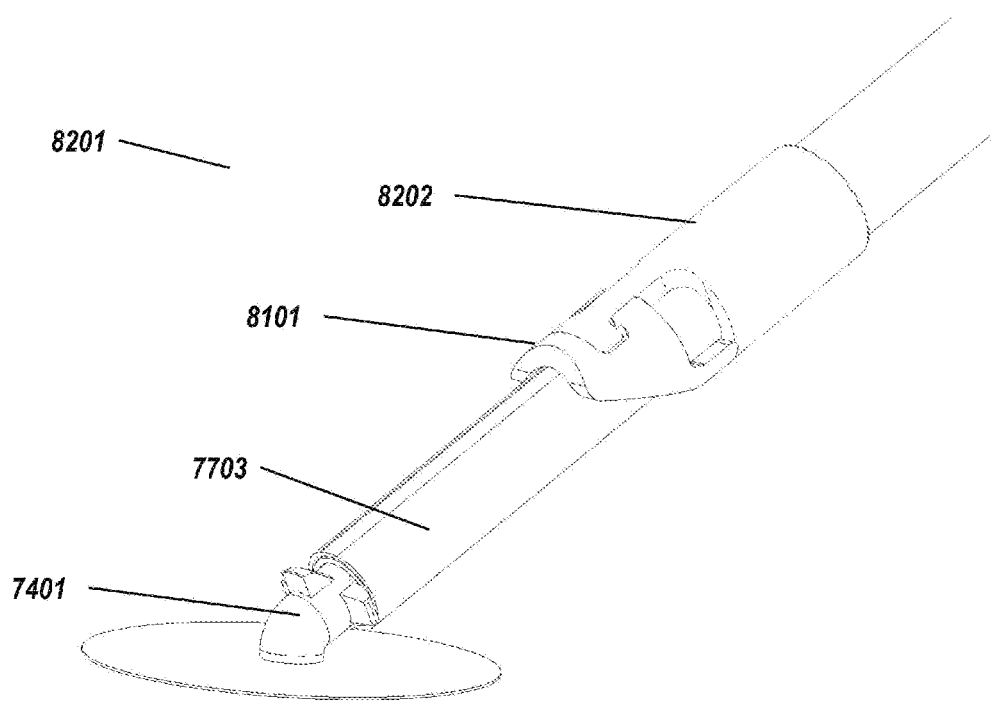
FIG. 82

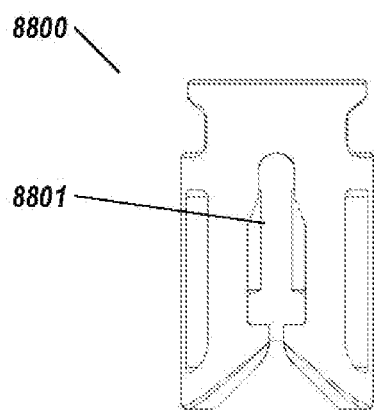
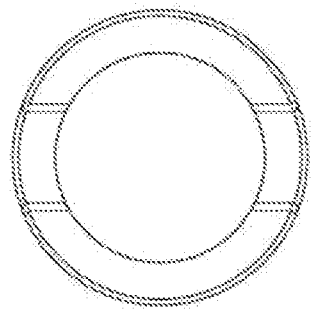
FIG. 88A                FIG. 88B
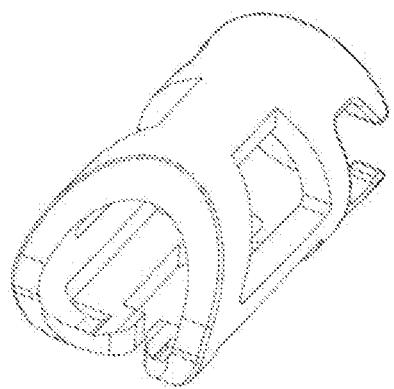
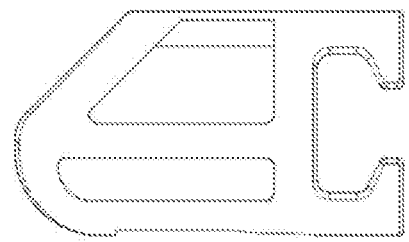
FIG. 88C                FIG. 88D

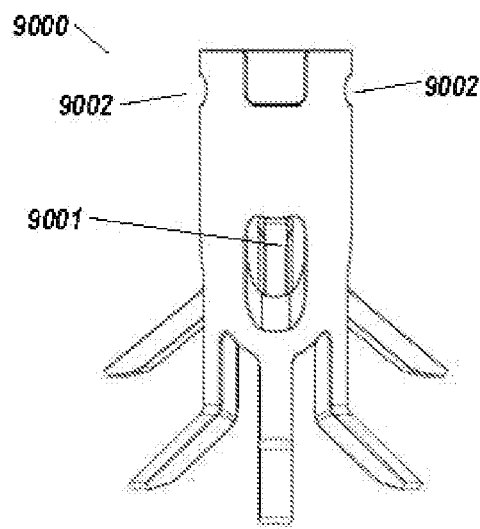
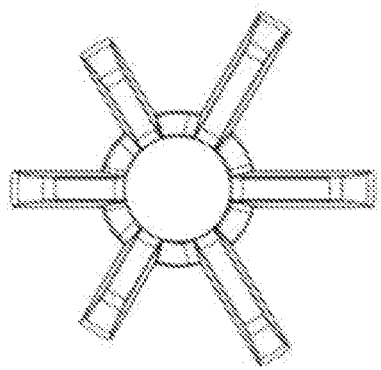
FIG. 90A          FIG. 90B
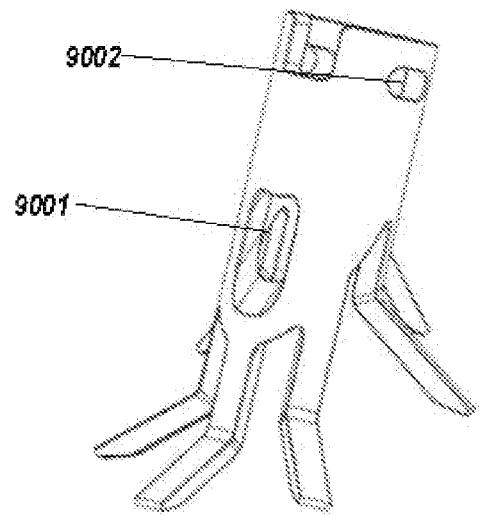
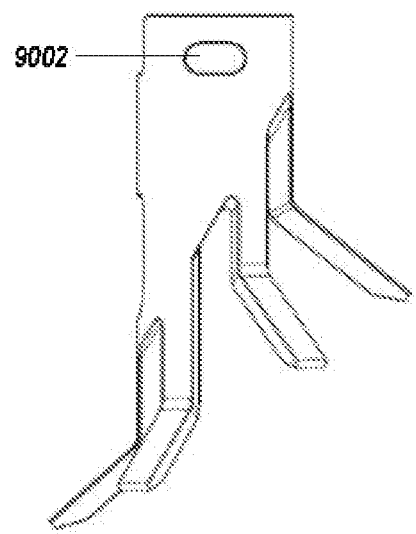
FIG. 90C          FIG. 90D

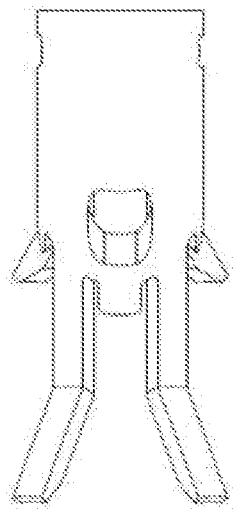
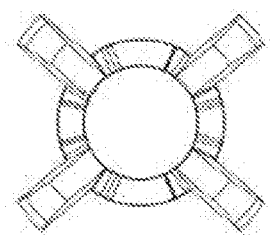
FIG. 91A                    FIG. 91B
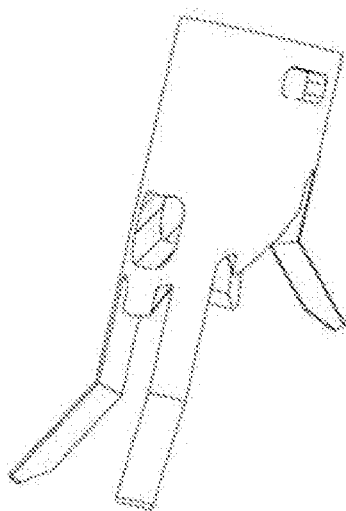
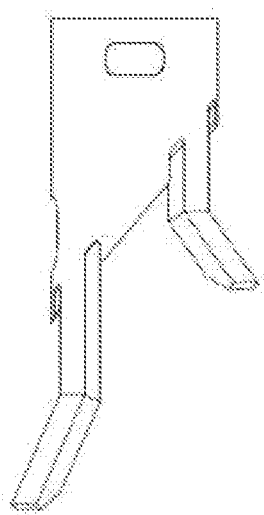
FIG. 91C                    FIG. 91D

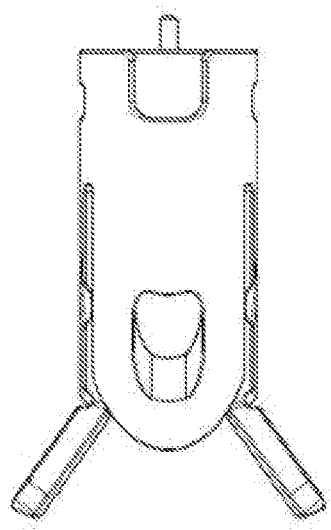
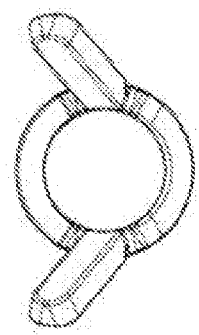
FIG. 92A      FIG. 92B
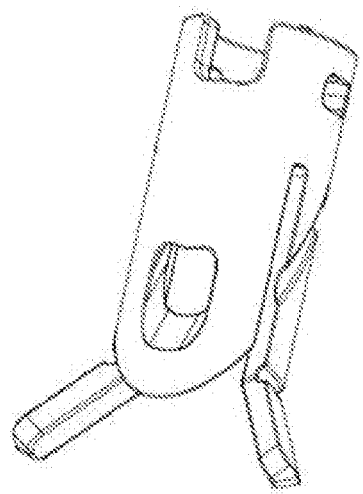
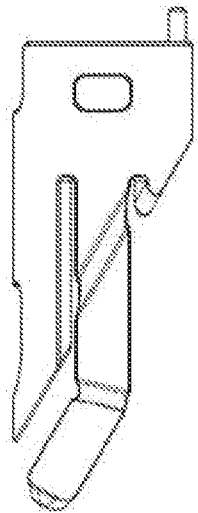
FIG. 92C      FIG. 92D

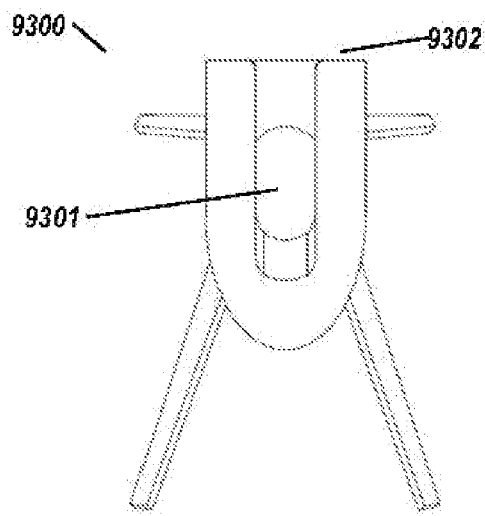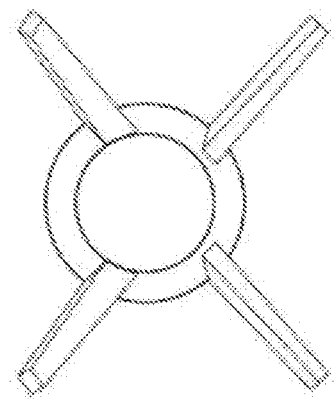
FIG. 93A  FIG. 93B
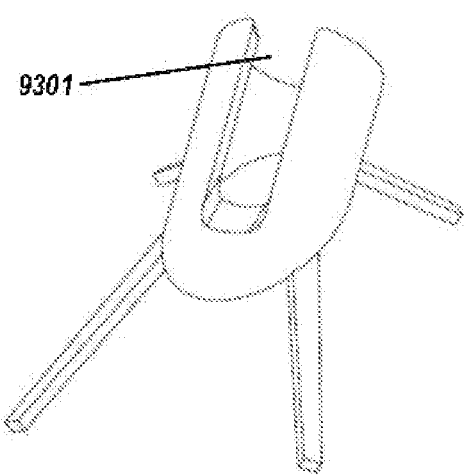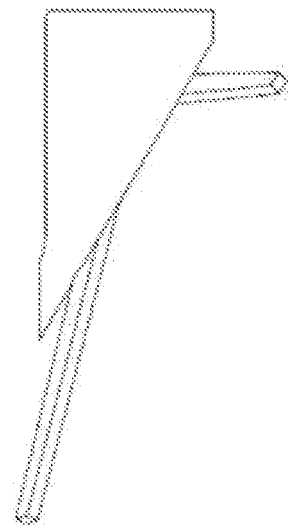
FIG. 93C  FIG. 93D

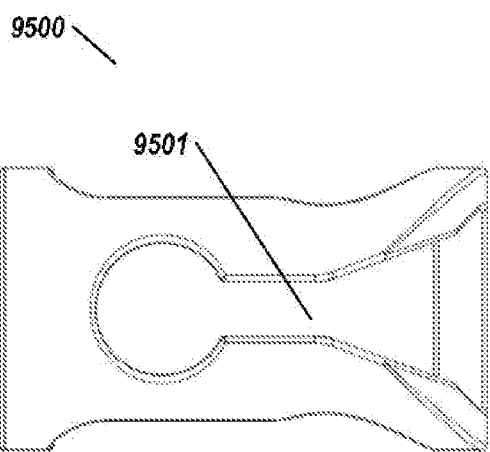
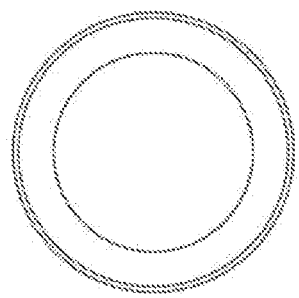
FIG. 95A  FIG. 95B
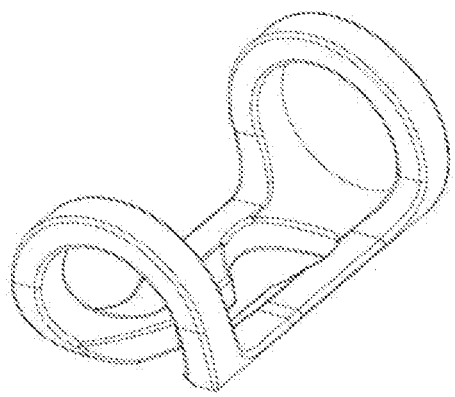
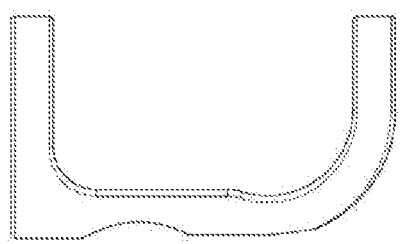
FIG. 95C  FIG. 95D

ARTERIOTOMY CLOSURE APPARATUS WITH SLOTTED SHOE FOR ADVANTAGEOUS PRESSURE DISTRIBUTION

CROSS REFERENCE TO RELATED APPLICATIONS

This application is a continuation of U.S. Non-Provisional patent application Ser. No. 16/061,028 filed Jun. 11, 2018, which claims priority to International Application No. PCT/EP2016/081183 filed Dec. 15, 2016, which claims priority to and the benefit of U.S. Provisional Application No. 62/267,644 filed Dec. 15, 2015, the entire contents of each of which are hereby incorporated by reference.

BACKGROUND

During a surgical or endoscopic operation on a body lumen, e.g., a blood vessel, an aperture is formed (e.g., from an arteriotomy) in the tissue of the lumen. Following the procedure, the aperture has to be closed in order for the lumen to heal. One relatively new type of closure apparatus has a flexible disc that is delivered into the body lumen to seal the aperture. The disc maintains the tissue in apposition until the lumen is healed, allowing the wound to heal from the inside of the lumen. The disc may operate in conjunction with a rigid core, which prevents the disc from dislodging from the sealing position.

In certain patient groups, the area surrounding the tissue within the body lumen is diseased and/or has accumulation (e.g., plaque or calcified lesions on the tissue wall). Due to the irregular surface topology of such areas, the effectiveness of the seal made by certain closure apparatuses is reduced, as channels are formed between the disc and the tissue surface.

There are benefits of improving the seal formed by a closure apparatus when closing an aperture formed in the tissue of the body lumen.

SUMMARY

During a surgical or endoscopic or other minimally invasive operation on a body lumen, e.g., a blood vessel, an aperture is formed (e.g., from an arteriotomy or a veinotomy) in the tissue of the lumen. Closure and healing can be assisted by a closure apparatus, e.g., an apparatus that has a flexible disc that is delivered into the body lumen to seal the aperture, and/or a rigid core, which prevents the disc from dislodging from the sealing position. The disclosed technologies can improve the seal formed by a closure apparatus when closing an aperture formed in the tissue of the body lumen. In certain embodiments, the disclosed technologies assist the closure of an aperture, e.g., by providing a compressive force on the exterior surface of a vessel, e.g., using an extra-arterial cage or shoe.

In one aspect, the invention is directed to a device for fixating an implant, the device comprising a shoe comprising one or more engagement elements for engagement with a column or support member of the implant. In certain embodiments, the shoe has a caged structure. In certain embodiments, the shoe comprises one or more concave structural elements. In certain embodiments, at least one structural element of the shoe is selected from the group consisting of indentations, ridges, shoulders, planes, curved planes, cavities, notches, holes, slots surfaces, and grooves. In certain embodiments, the device comprises at least one hole and one shoulder. In certain embodiments, the device is bioabsorbable. In certain embodiments, the device comprises at least one material selected from the group consisting of Polydioxanone, Poly-L-lactide, Poly-D-lactide, Poly-DL-lactide, Polyglycolide, ε-Caprolactone, and Polyethylene glycol. In some embodiments, the material of the support member and/or sealable member is a co-polymer of, for example, but not limited to, Polydioxanone, Poly-L-lactide, Poly-D-lactide, Poly-DL-lactide, Polyglycolide, ε-Caprolactone, and Polyethylene glycol.

In another aspect, the invention is directed to a device for sealing an aperture in a tissue of a body lumen, the device comprising: (i) a flexible support member comprising a base and a sealable member; (ii) a column comprising a centering tab and/or one or more locking tabs; and (iii) an extra-arterial shoe comprising one or more engagement elements for engagement with the flexible support member. In certain embodiments, the extra-arterial shoe comprises a shoulder. In certain embodiments, the one or more locking tabs engage with the extra-arterial shoe by snap fitting with the shoe. In certain embodiments, the one or more locking tabs engage with the extra-arterial shoe by engaging the shoulder of the shoe. In certain embodiments, the column comprises two locking tabs. In certain embodiments, the locking tabs are positioned opposite to each other along the circumference of a cylindrical portion of the flexible support member. In certain embodiments, the centering tab reversibly engages one or more features of the extra-arterial shoe. In certain embodiments, the one or more features are a notch, a hole, surface, or a groove. In certain embodiments, the device comprises a delivery system comprising an external shaft. In certain embodiments, the extra-arterial shoe is mounted on the external shaft and is slideably moveable along a longitudinal axis of the external shaft. In certain embodiments, the device comprises a shoe pusher. In certain embodiments, the shoe pusher is mounted on the external shaft and is slideably moveable along a longitudinal axis of the external shaft.

In another aspect, the invention is directed to a device for sealing an aperture in a tissue of a body lumen, the device comprising: (i) a flexible support member comprising a base and a sealable member; (ii) a column comprising a centering tab and/or one or more locking tabs; (iii) an extra-arterial shoe comprising one or more engagement elements for engagement with the flexible support member; (iv) a delivery system comprising an external shaft having a longitudinal axis; and (v) a shoe pusher. In certain embodiments, the extra-arterial shoe is mounted on the external shaft and is slideably moveable along a longitudinal axis of the external shaft, and the shoe pusher is mounted on the external shaft and is slideably moveable along a longitudinal axis of the external shaft. In certain embodiments, the shoe pusher is reversibly engageable to the external shoe. In certain embodiments, the shoe pusher and the extra-arterial shoe are moveable between a first, proximal position and a second, distal position, such that in the first position, the shoe pusher and the extra-arterial shoe are reversibly engaged and slideably moveable along the longitudinal axis, and such that in the second position, the extra-arterial shoe engages the flexible support member. In certain embodiments, the shoe pusher is moveable to a third, proximal position. In certain embodiments, the extra-arterial shoe, upon deployment and engagement, is capable of exerting pressure on an exterior surface of the tissue. In certain embodiments, the aperture in a tissue of a body lumen is a surgical or endoscopic perforation in a body cavity.

In another aspect, the invention is directed to a device for sealing an aperture in a tissue of a body lumen, the device comprising: (i) a flexible support member comprising a base and a sealable member; (ii) a column comprising a locking neck; and (iii) an extra-arterial shoe comprising one or more engagement elements for engagement with the flexible support member. In certain embodiments, the extra-arterial shoe comprises an engagement slot. In certain embodiments, the locking neck engages with the extra-arterial shoe by snap fitting with the shoe. In certain embodiments, the locking neck engages with the extra-arterial shoe by engaging the engagement slot. In certain embodiments, the device comprises a delivery system comprising an external shaft. In certain embodiments, the extra-arterial shoe is mounted on the external shaft and is slideably moveable along a longitudinal axis of the external shaft. In certain embodiments, the device comprises a shoe pusher. In certain embodiments, the shoe pusher is mounted on the external shaft and is slideably moveable along a longitudinal axis of the external shaft.

In certain embodiments, the body lumen is the inside space of a biological structure selected from the group consisting of gastrointestinal tract, heart, peritoneal cavity, esophagus, vagina, rectum, trachea, bronchi, and blood vessel, e.g., the femoral artery, iliac artery, subclavian artery, ascending and descending aorta, auxiliary and brachial arteries, femoral vein, iliac vein, subclavian vein, and vena cava.

Further features and aspects of example embodiments of the present invention are described in more detail below with reference to the appended Figures.

BRIEF DESCRIPTION OF THE DRAWING

FIGS. 19A, 19B, and 19C are diagrams of a perspective view, a side view, and a front view of a closure device with a threaded portion to allow assembly of the sealable member to the support member without distortion and/or deformation of the sealable member.

FIGS. 32A, 32B, 32C, and 32D are diagrams of perspective, top, front, and side views of an illustrative embodiment of a closure apparatus.

FIGS. 45A, 45B, 45C, and 45D are diagrams of perspective, top, front, and side views of an illustrative embodiment of a closure apparatus.

FIGS. 61A, 61B, 61C, and 61D are diagrams of perspective, top, front, and side views of an illustrative embodiment of a closure apparatus.

FIGS. 69A, 69B, 69C, and 69D are diagrams of perspective, top, front, and side views of an illustrative embodiment of a closure apparatus.

FIGS. 81A and 81B are diagrams showing perspective views of an exemplary extra-arterial shoe according to an illustrative embodiment.

FIG. 82 is a diagram of an exemplary shoe connected to an exemplary delivery system in an initial position, according to an illustrative embodiment.

FIGS. 88A, 88B, 88C, and 88D are diagrams showing a bottom view, a rear view, a perspective view, and a side view of an exemplary extra-arterial shoe.

FIGS. 90A, 90B, 90C, and 90D are diagrams showing front, top, perspective and side views of an alternative embodiment of an extra-arterial shoe.

FIGS. 91A, 91B, 91C, and 91D are diagrams showing front, top, perspective and side views of an alternative embodiment of an extra-arterial shoe.

FIGS. 92A, 92B, 92C, and 92D are diagrams showing front, top, perspective and side views of an alternative embodiment of an extra-arterial shoe.

FIGS. 93A, 93B, 93C, and 93D are diagrams showing front, top, perspective and side views of an alternative embodiment of an extra-arterial shoe.

FIGS. 95A, 95B, 95C, and 95D are diagrams showing front, top, perspective and side views of an alternative embodiment of an extra-arterial shoe.

DETAILED DESCRIPTION

As described herein, illustrative embodiments provide surgical closure systems, devices, and methods useful for (i) bringing about alignment of the tissues surrounding a perforation in a body lumen, thereby closing the aperture in the body lumen, (ii) forming a tamponade at the aperture when bringing about the alignment of the tissues, and (iii) maintaining the tissues surrounding the perforation in alignment until the perforation is sealed. The systems, devices, and methods are used, in some embodiments, to close a surgical perforation in a body cavity, such as the gastrointestinal tract, heart, peritoneal cavity, esophagus, vagina, rectum, trachea, bronchi, and blood vessel, including for example, but not limited to the femoral artery, subclavian artery, ascending and descending aorta, auxiliary and brachial arteries femoral vein, iliac vein, subclavian vein, and vena cava.

Figure 1A:
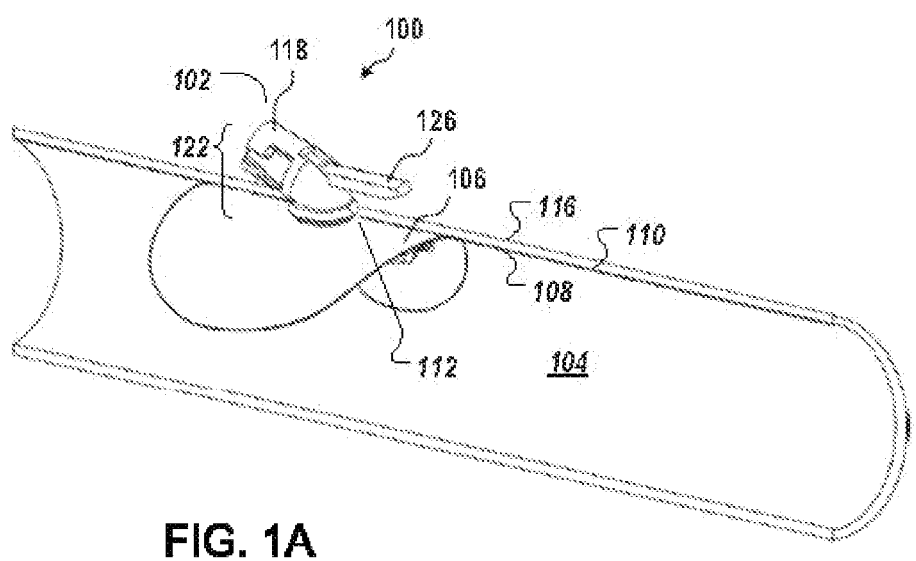
FIGS. 1A and 1B are diagrams showing a perspective view and a cross-sectional view of an exemplary closure device deployed at a sealing position in a body lumen.
Figure 1B:
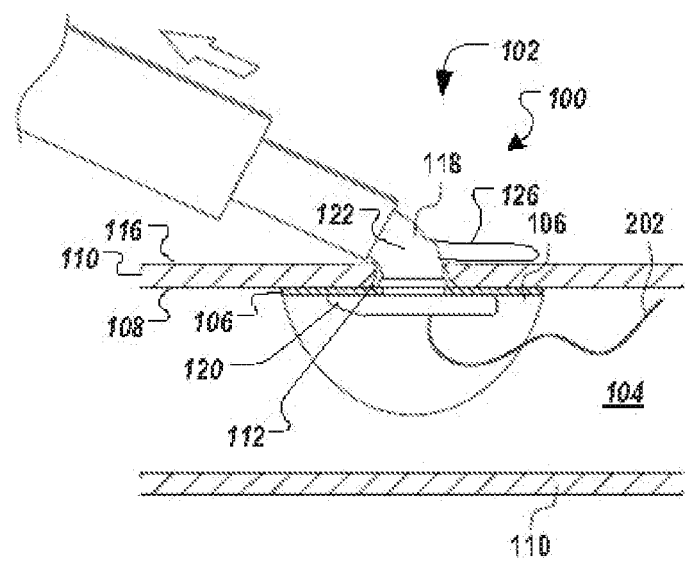

FIGS. 1A and 1B are diagrams showing a perspective view and a cross-sectional view of an exemplary closure device 100 deployed at a sealing position 102 in a body lumen 104.

The closure device 100 includes a sealable member 106 (e.g., a flexible wing) positionable against an interior surface 108 of the tissue 110 adjacent the aperture 112 in the tissue (e.g., so as to form a tamponade at the aperture 112). Although flat or slightly curved when in a relaxed state, the sealable member 106 flexibly curves to conform to the interior surface 108 of the lumen 104 to which it engages, in the deployed state.

The closure device 100 includes a support member 118 (e.g., a foot) comprising a base 120 (e.g., an O-ring foot-core) and a column 122. The base 120 supports the sealable member 106 during the delivery and deployment of the sealable member 106 in the body lumen 104 by retaining and/or holding the sealable member 106 against the interior surface 108 of the tissue 110 when the closure device 100 is in the sealing position. In some embodiments, the base 120 exerts a force to bias the sealable member 106 against the tissue.

Figure 2A:
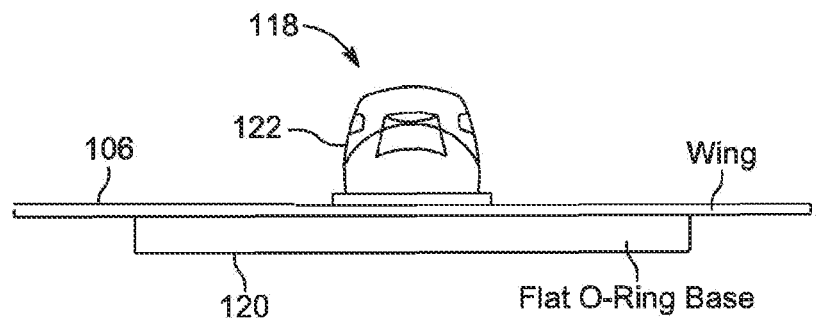
FIG. 2A is a diagram of the closure device in a stowed position, according to an illustrative embodiment.
Figure 2B:
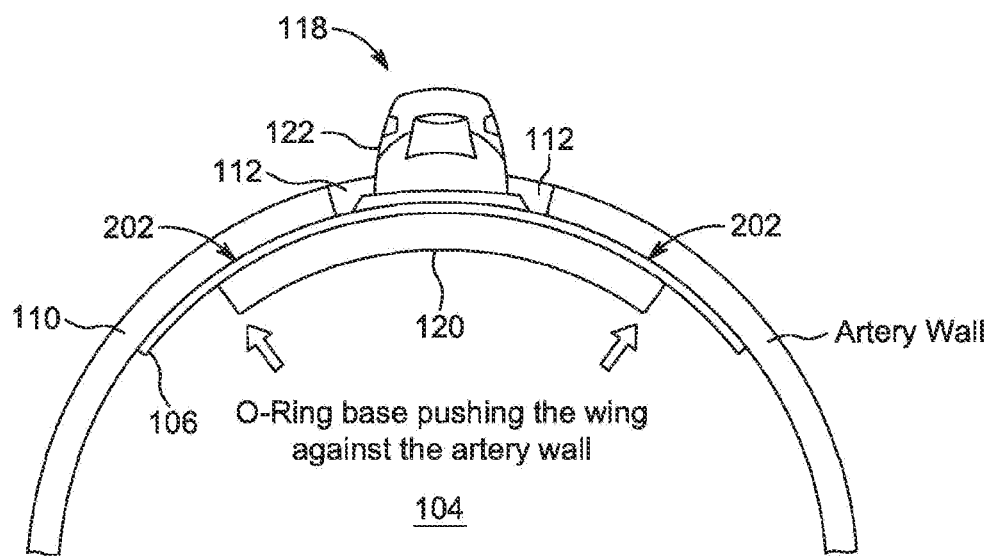
FIG. 2B is a diagram of the closure device in a deployed state at the sealing position, according to an illustrative embodiment.

FIG. 2A is a diagram of the sealable member 106 and the base 120 of the support member 118 in a relaxed position, according to an illustrative embodiment. FIG. 2B is a diagram of the members in a deployed state at the sealing position, according to an illustrative embodiment. In certain embodiments, the base 120 slightly bends when in the relaxed position.

In some embodiments, once implanted in the body lumen, the base 120 presses against the interior shape of the lumen 104 by hydraulic pressure exerted by fluids in the body lumen 104 (e.g., by hemodynamic hydraulic forces exerted by blood in a blood vessel). In doing so, the base 120 improves the seal formed by the sealable member 106 over the aperture 112, thus, providing a faster and more secure closure of the aperture 112. The base 120 connects to the column 122, which is disposed, when the device is in the sealing position, in and through the aperture 110. In certain embodiments, a guard member 126 (see FIGS. 1A and 1B) maintains the column 122 in position at the sealing position once the device 100 is deployed, whereby the guard member 126 prevents the dislodgement of the sealable member 106 from the sealing position, e.g., due to impact near the aperture or movement of the patient.

In some embodiments, once implanted in the body lumen, the base 120 bends against the interior shape of the lumen 104 so as to compress the peripheral portions of the sealable member 106 against the interior surface 108 of the tissue 110. Hydraulic pressure, as discussed above, may contribute to the bending of the base 120 in such embodiments. The base 120, in these embodiments, also improves the seal formed by the sealable member 106 over the aperture 112, thus, providing a faster and more secure closure of the aperture 112. The support member 118 may also include a guard member 126 to prevent the dislodgement of the sealable member 106 from the sealing position, e.g., due to impact near the aperture or movement of the patient.

In some embodiments, the support member 118 may include a guard member 126 to prevent the dislodgement of the sealable member 106 from the sealing position, when hydraulic pressure of a blood vessel is relatively low. The guard member may provide a mean to compress the implant into a vessel (e.g., by an operator).

Lateral Support Portions of the Base

Figure 3A:
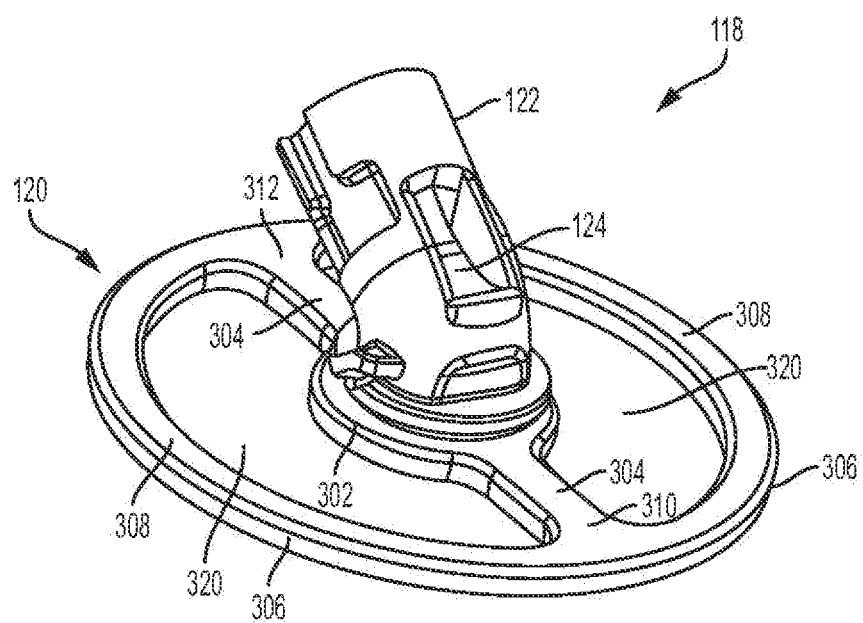
FIGS. 3A and 3B are diagrams showing a perspective view and a bottom view of a support member of the closure device, according to an illustrative embodiment.
Figure 3B:
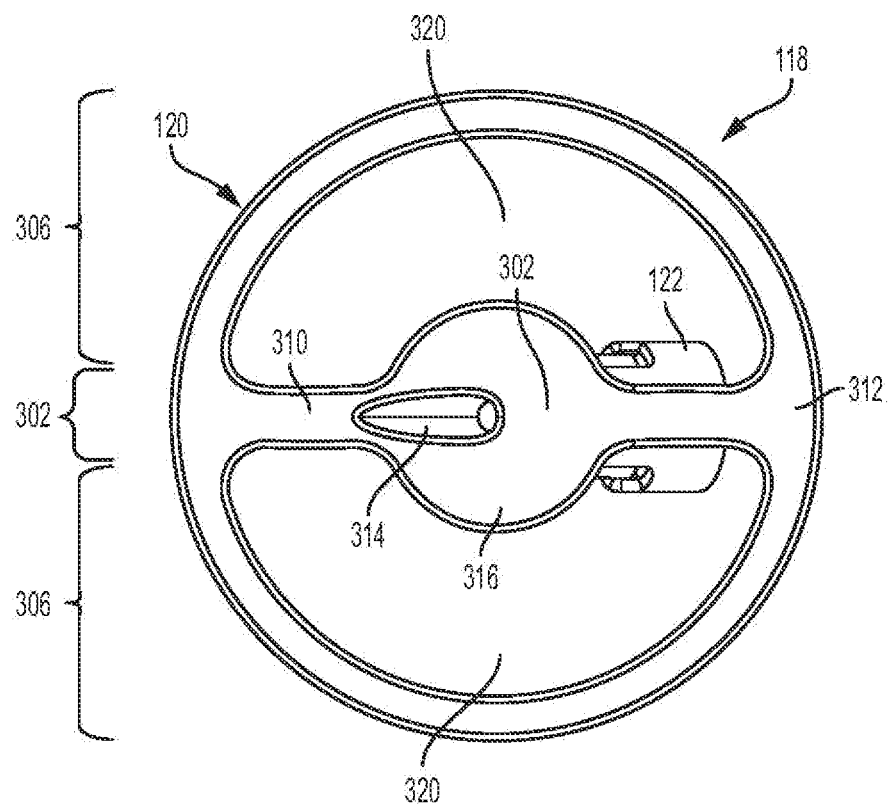

FIGS. 3A and 3B are diagrams showing a perspective view and a bottom view of a support member of the closure device, according to an illustrative embodiment. The base 120 of the support member 118 includes (i) a central portion 302 that connects to column 122 and (ii) one or more lateral support portions 306 extending from the central portion 302. The lateral support portions 306 have support surfaces 308 that retain and/or hold the peripheral portions of the sealable member 106 against the interior surface 108 of the tissue 110. In certain embodiments, the lateral support portion 306 retains and/or holds the peripheral portions and exerts a force that biases the sealable member 106 against the tissue. In certain embodiments, the force is compressive. The lateral support portions 306 in conjunction with the sealable member 106 increase the rigidity of the closure device 100 at regions of contact with the tissue 110, while allowing the closure device 100 to bend during the deployment and during the delivery. The increased rigidity reduces the risk that of inadvertent dislodgment of the closure device 100 after it has been deployed in the body lumen 104, e.g., due to an impact near the closure device or movements of the patient or of inadvertent pull-out of the device 100 (e.g., through the aperture) during its deployment into the body lumen 104.

In some embodiments, the central portion 302 forms a rigid core to which the lateral support portions 306 flexibly connect. In some embodiments, the central portion 302 and the lateral support portions 306 form a single unitary body.

In some embodiments, the lateral support portions 306 forms a gap 320 with respect to the central portion 302.

Still referring to FIGS. 3A and 3B, the central portion 302 of the base 120 includes an anterior support portion 310 and a posterior support portion 312. The contact surfaces 304 of both the anterior and posterior support portions 310, 312 contact and/or press against the anterior and posterior portions of the sealable member 106. The lateral support portions 306 extend from at least one of the anterior support portion 310 and the posterior support portion 312. As shown, the posterior support portion 312, in some embodiments, is disposed proximally to the column 122 of the support member 118, and the anterior support portion 312 is disposed distally to the column 122.

Directionally-Inducted Rigidity of the Devices

In another aspect, the flexible support member 118 may be shaped to provide more rigidity to peripheral portions of the sealable member 106 along a direction to which the sealable member is pulled during the deployment of the closure device 100. The directionally-induced rigidity ameliorates the risk of an accidental pull-out of the sealable member from the lumen 104 during deployment.

Figure 4A:
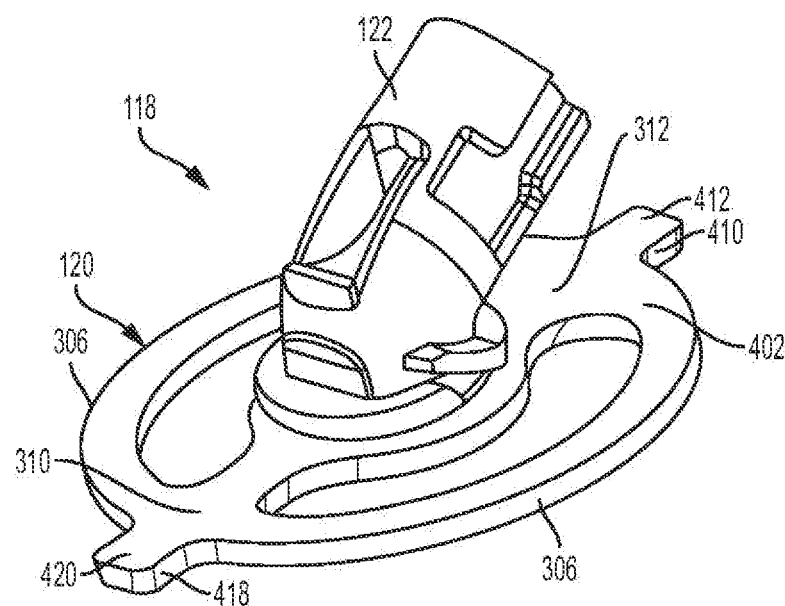
FIGS. 4A and 4B are diagrams showing a perspective view and a bottom view of a support member of the closure device with directionally-induced rigidity, according to an illustrative embodiment.
Figure 4B:
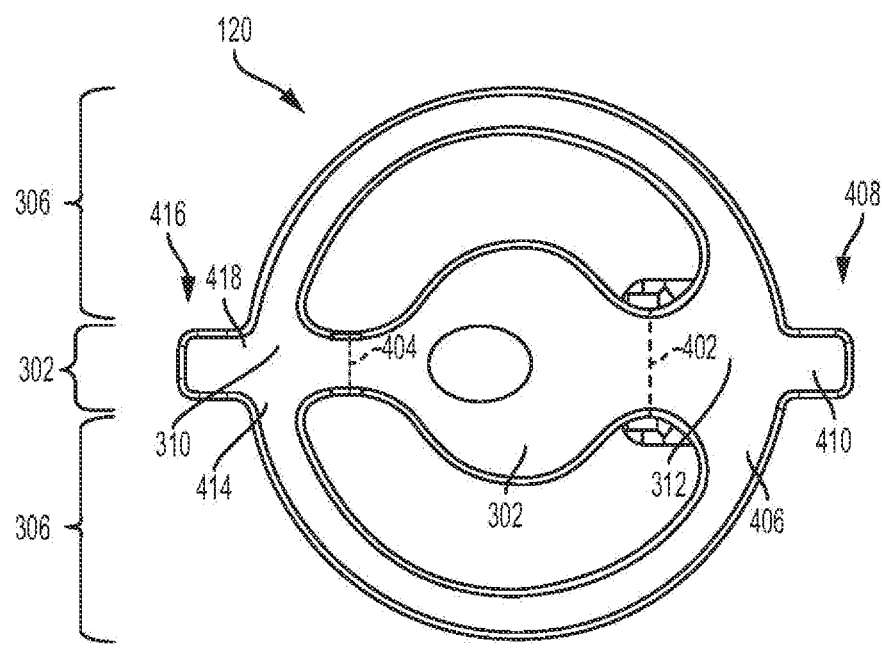

FIGS. 4A and 4B are diagrams showing a support member 118 of the closure apparatus 100 with directionally-induced rigidity. This increased rigidity is employed at a specific part of the base 120 that, preferably, corresponds to the direction of the column 122. In certain embodiments, the base 120 provides more resistance, for example, at region 312, making the portion of the sealable member 106 corresponding to such region subject to less bending. Thus, greater force may be applied to that region of the sealable member 106 before the sealable member 106 would pull through the aperture 112. This reduces the risk that the implant can dislodge from its deployed position due to, for example, movements by the patient and/or impact to the nearby area. The greater force also gives the surgeon a better tactile feel of sealable member 106 during the deployment and creates better apposition of the sealable member 106 against the inner lumen of the body lumen 104. Thus, a faster and more effective seal can be created.

As shown in FIGS. 4A and 4B, the posterior support portion 312 is disposed proximally to the column 122 of the support member 118 and has first maximum cross-sectional area 402. The anterior support portion 310 is disposed distally to the column 122 of the support member 118 and has a second maximum cross-sectional area 404. The first maximum cross-sectional area 402, in certain embodiments, is larger than the second maximum cross-sectional area 404 such that the posterior support portion 312 (and/or adjacent portions of the lateral support member) is more rigid than the anterior support portion 310.

In certain embodiments, the base 120 of the support member 118 has a varying cross-sectional thickness along the direction between the anterior support portion 310 and the posterior support portion 312. The varying thickness along this direction may provide greater rigidity at the posterior support portion 312 of the base 120 than the anterior support portion 310.

Referring still to FIG. 4B, in certain embodiments, the lateral support portions 306 extend from the posterior support portion 312 at a location 406 between (i) a posterior end 408 of the posterior support portion 312 and (ii) the central portion 302, thereby forming a region 410. The region 410 can be characterized as a tab 410 that extends from a perimeter defined by the lateral support portions 306 around the central portion 302. The tab 410 provides additional surface area 412 (see FIG. 4A) to the posterior region of the sealable member 106.

In addition, the lateral support portions 306 may extend from the anterior support portion 310 at a location 414 between an anterior end 416 of the anterior support portion 310 and the central portion 302, thereby forming a region 418. This region 418 can also be characterized as a tab 418. The tab 418 provides additional surface area 420 to the anterior region of the sealable member 106.

Figure 4C:
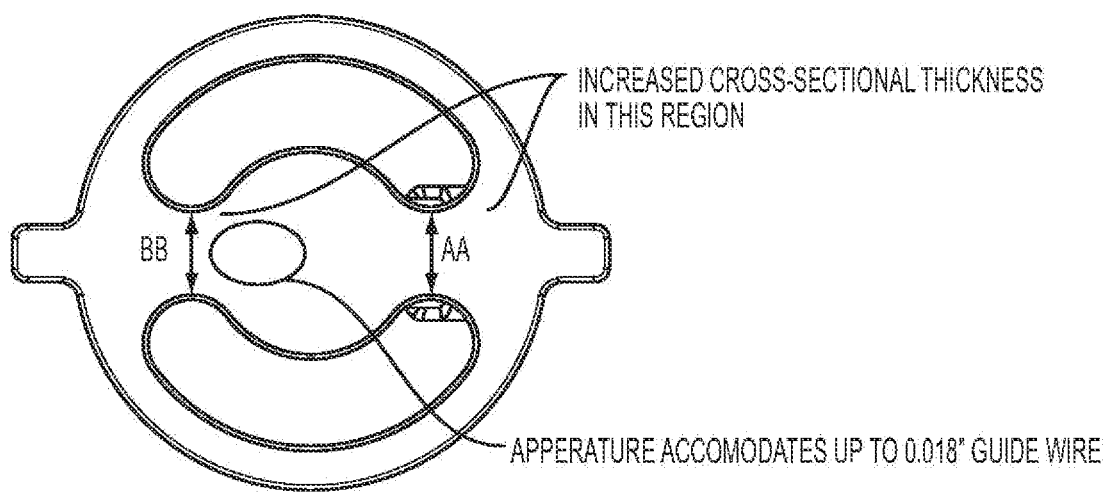
FIG. 4C is a diagram showing a bottom view of a support member of the closure device with directionally-induced rigidity, according to an illustrative embodiment.

In some embodiments, as shown in FIG. 4C, the support member has increased the first maximum cross-sectional area AA and the second maximum cross-sectional area BB. The increased cross-sectional area may provide more rigid support, so that the support member 118 has better user tactic feel. The increased cross-sectional area may reduce risk of dislocation of the supporting member from arteriotomy.

Figure 4D:
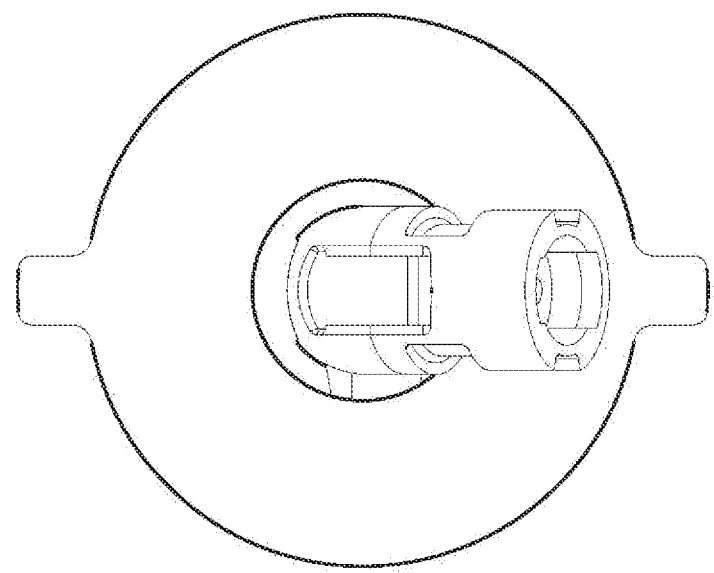
FIGS. 4D and 4E are diagrams showing a perspective view and a bottom view of a support member of the closure device with directionally-induced rigidity, according to an illustrative embodiment.
Figure 4E:
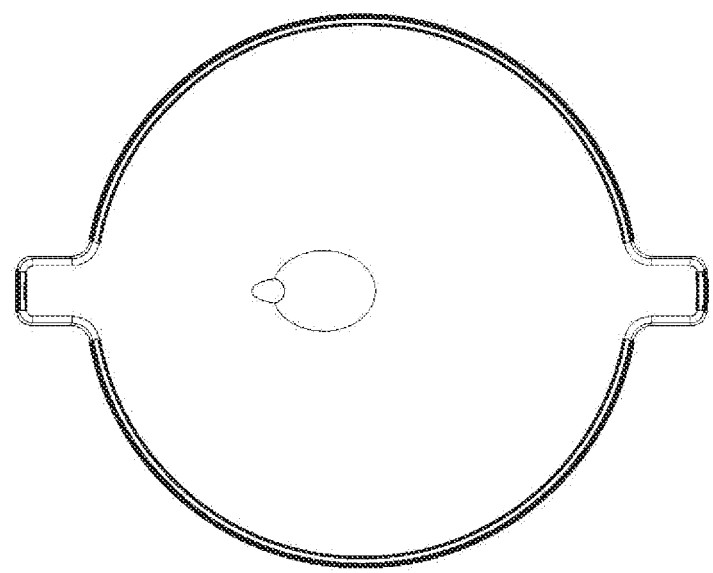

In some embodiments, as shown in FIGS. 4D and 4E, the base may not have a gap between the one or more lateral support portions and the central portion. The continuous surface may facilitate faster endothelial cell coverage and encapsulation when implanted in vivo.

Figure 5:
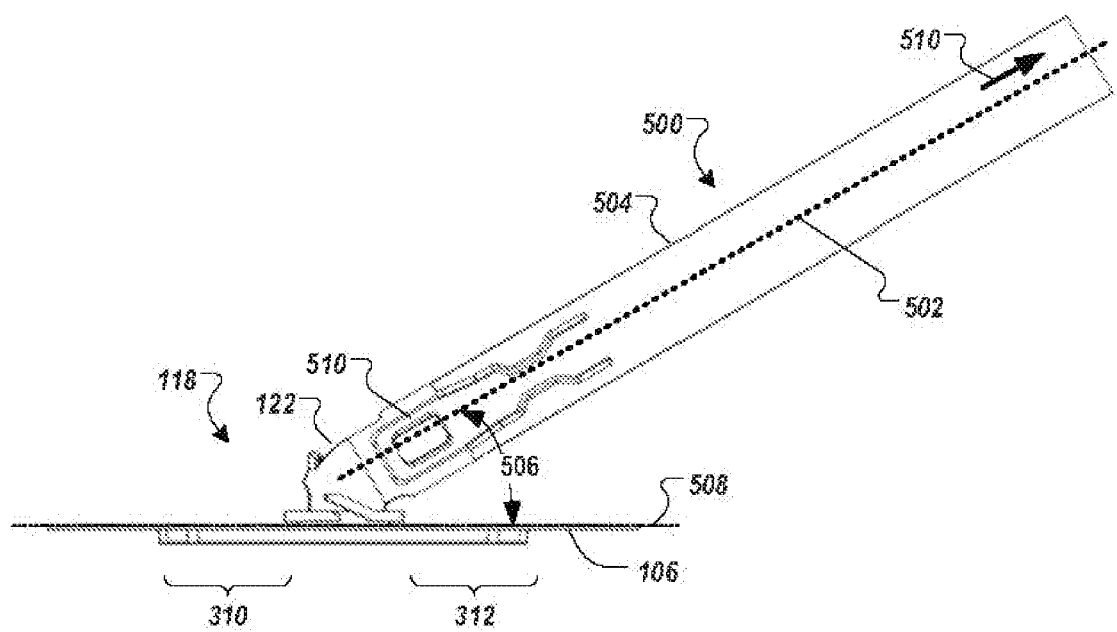
FIG. 5 is a diagram of an example closure device (e.g., of FIG. 7) secured to a delivery apparatus.

FIG. 5 is a diagram of an example closure device 100 secured to a delivery apparatus 500 of the device 100. The apparatus 500 is equipped with an appropriate docking mechanism for a given closure device 100. In certain embodiments, the docking mechanism comprises a T-shaped engagement arm that engages a corresponding recess on the closure device 100. In some embodiments, the recess and engagement arms may include a pin or protrusion, e.g., for alignment.

As shown, the column 122 of the support member 118 is angularly disposed, when secured to the apparatus 500, along an axis 502 corresponding to a longitudinal axis of a delivery shaft 504 to which the closure device 100 is releasably attached. The delivery shaft 504 may engage the column 122, in some embodiments, at two recesses 510 located on the proximal tip of the column 122. In certain embodiments, the column 122 forms an angle 506 between a plane 508 corresponding to the sealable member 106 in a rest configuration and the longitudinal axis 502 of the delivery shaft 504. In certain embodiments, the angle 506 is between about 10 degrees and about 70 degrees, including, but not limited to, 10, 15, 20, 25, 30, 35, 40, 45, 50, 55, 60, 65, and 70 degrees.

Additional examples of the delivery apparatus is found in U.S. Patent Application Publication No. US 2014/0018846, titled "Implants and Methods for Percutaneous Perforation Closure," the content of which is incorporated herein in its entirety.

Examples of the Support Member

Various embodiments of the lateral support portions are now described. In some embodiments, the lateral support portions 306 extend from the central portion 302 to form a continuous structure, for example, but not limited to, a ring (e.g., circle, oval, rectangular, ellipse, diamond) around the central portion 302 of the base 120. In other embodiments, the lateral support portions 306 form one or more cantilevers that extend from the central portion 302. FIGS. 6-16 are diagrams showing perspective views of other exemplary embodiments of the support members 118.

Figure 6:
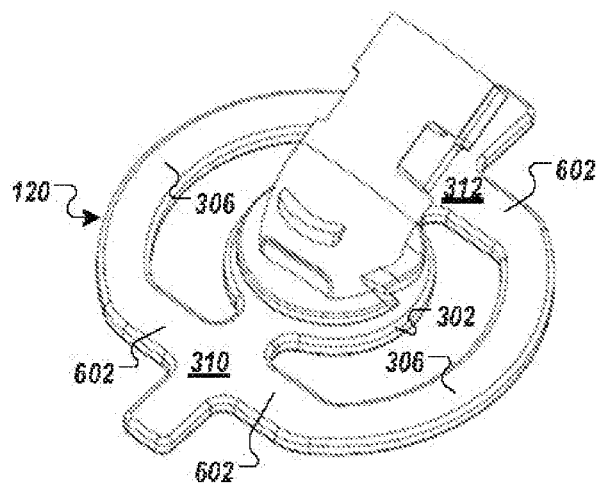
FIG. 6 is a diagram showing a perspective view of an alternative embodiment of a support member.

As shown in FIGS. 6-9, the lateral support portions 306 form a continuous structure around the central portion 302. Specifically, as shown in FIG. 6, the lateral support member 306 forms a straight connection region 602 that extends from the anterior support portion 310 and the posterior support portion 312 of the base 120.

Figure 7:
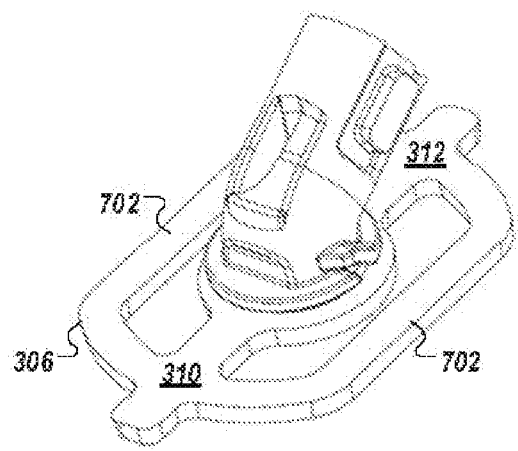
FIG. 7 is a diagram showing a perspective view of an alternative embodiment of a support member.

As shown in FIG. 7, each of the lateral support members 306 forms a straight support region 702. Each of the straight support regions 702 is parallel to the anterior support portion 310 and the posterior support portion 312 of the base 120.

Figure 8:
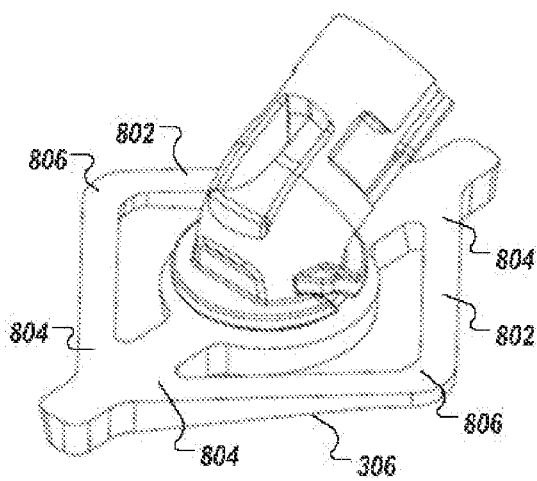
FIG. 8 is a diagram showing a perspective view of an alternative embodiment of a support member.

As shown in FIG. 8, the lateral support member 306 forms a diamond-shaped support region 802. In certain embodiments, the diamond-shaped support region 802 has a uniform cross-sectional thickness. In other embodiments, the diamond-shaped support region 802 has a varying cross-sectional thickness in which the thickness is greater at the point of connection 804 than at the peripheral portion 806.

Figure 9:
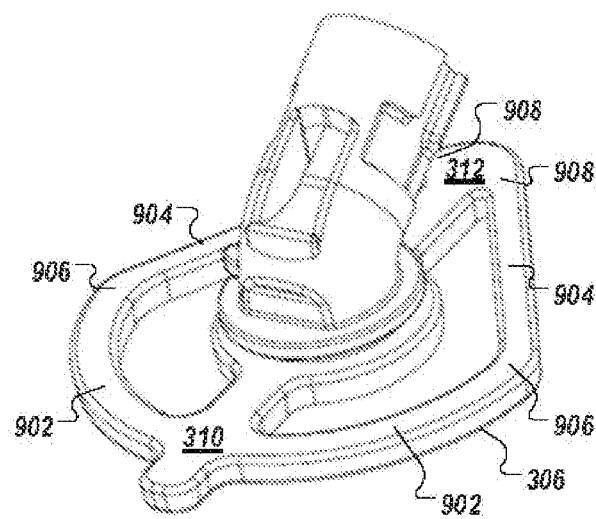
FIG. 9 is a diagram showing a perspective view of an alternative embodiment of a support member.

As shown in FIG. 9, the lateral support member 306 has a wide base at one region, which then tapers to a point of connection with the central portion 302. As shown, a protruded region 902 extends from the anterior support portion 310. The protruded region 902 then tapers to the point of connection 908. This shape can be characterized as a snow shoe or a leaf. Alternatively, in certain embodiments, the protruded region 902 extends from the posterior support portion 312, and the taper region 904 extends from the anterior support portion 310.

Figure 10:
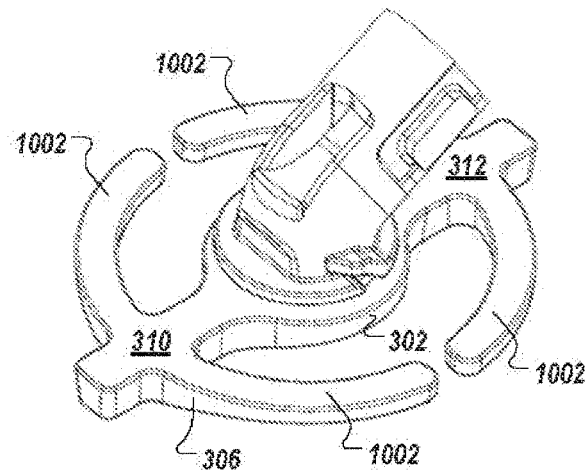
FIG. 10 is a diagram showing a perspective view of an alternative embodiment of a support member.
Figure 11:
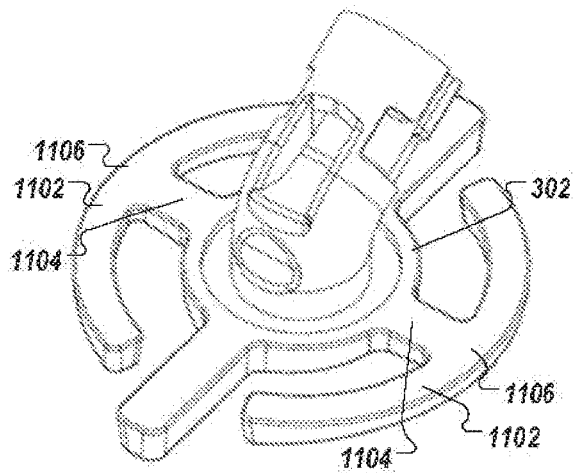
FIG. 11 is a diagram showing a perspective view of an alternative embodiment of a support member.
Figure 12:
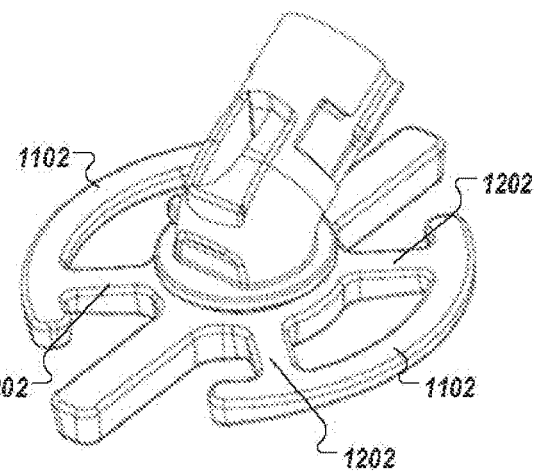
FIG. 12 is a diagram showing a perspective view of an alternative embodiment of a support member.

As shown in FIGS. 10 to 12, each of the lateral support portions 306 forms a non-continuous structure around the central portion 302. Specifically, in FIG. 10, the lateral support member 306 forms an arcuate structure 1002 around the central portion 302. Each of arcuate portions 1002 extends from the anterior support portion 310 and the posterior support portion 312 of the base 120 of the support member 118.

In FIGS. 11 and 12, each of the lateral support members 306 also forms an arcuate portion 1102 around the central portion 302. The arcuate portion 1102 has a connection region 1104 that extends from the central portion 302 of the base 120. In FIG. 11, each of the arcuate portions 1102 has a single connection region 1104. In FIG. 12, each of the arcuate portions 1102 has a plurality of connection regions 1202.

Referring still to FIGS. 11 and 12, in certain embodiments, the cross-sectional thickness of the base 120 is varied between the central portion 302 and the peripheral regions 1106 of the lateral support portions 306.

Figure 13:
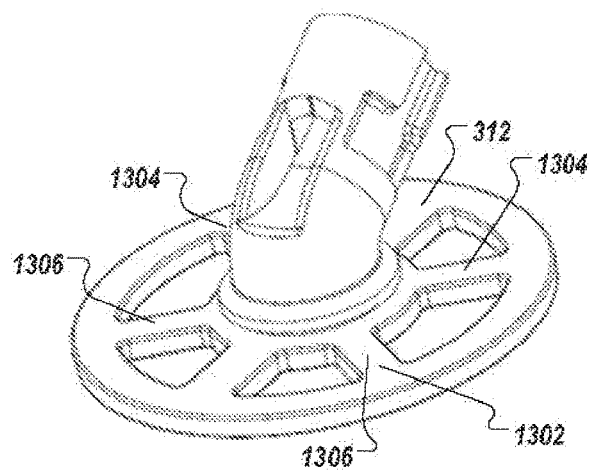
FIG. 13 is a diagram showing a perspective view of an alternative embodiment of a support member.

In FIG. 13, the lateral support portions 306 form a continuous structure around and connected through the central portion 302. The structure can be characterized as a wagon wheel. In such embodiments, the lateral support portion 306 have between 4 and 20 connection regions 1302. In certain embodiments, the connection regions 1302 are uniformly spaced apart from each other. In other embodiments, the spacing between the connection regions 1302 is varying. For example, the connection regions 1304 proximally located to the posterior support portion 312 may be spaced more closely to one another than connection regions 1306 distally located to the posterior support portion 312.

Figure 14:
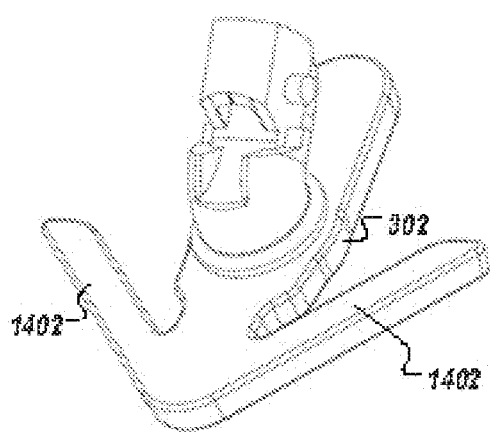
FIG. 14 is a diagram showing a perspective view of an alternative embodiment of a support member.
Figure 15:
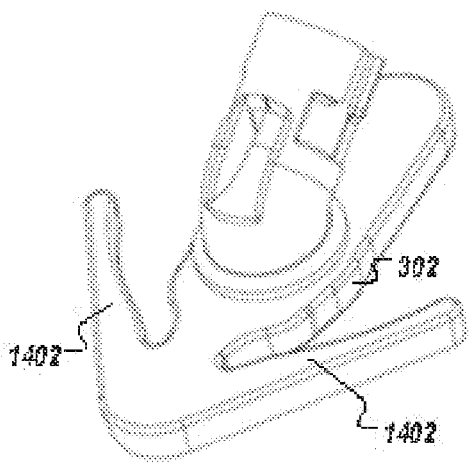
FIG. 15 is a diagram showing a perspective view of an alternative embodiment of a support member.

In FIGS. 14 to 15, the lateral support portions 306 form one or more cantilevers 1402 that extend from the central portion 302 (or the anterior support portion). In some embodiments, the cantilevers 1402 have a uniform cross-sectional thickness (see FIG. 14). In other embodiments, the cantilevers 1402 have a varying cross-sectional thickness (see FIG. 15).

Figure 16:
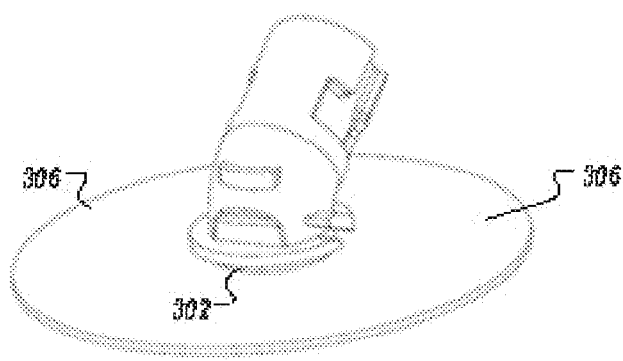
FIG. 16 is a diagram showing a perspective view of an alternative embodiment of a support member.

In FIG. 16, the lateral support portions 306 form a continuous surface with the central portion 302. The structure can be characterized as a disc.

Additional views of the various embodiments, as well as further examples of the closure device 100, are provided in FIGS. 23A-72C.

Other Components of the Closure Device

Referring back to FIG. 3A, the column 122 of the support member 118, in some embodiments, has an engagement portion 124 to secure the guard member 126 (e.g., an insertable or engagable pin or cage in FIG. 18A) to the support member 118. In some embodiments, the guard member 126 is maintained at a location relative to the exterior surface 116 of the tissue 110 when the closure device 100 is in the sealing position. In some embodiments, the guard member 126 compresses against the exterior surface 116 of the tissue 110 when the closure device 100 is in the sealing position. In some embodiments, the guard member 126 is moveable, from a stowed state to a deployed state, to engage exterior surface 116 of the tissue adjacent the aperture such that a portion of the tissue is disposed between the guard member 126 and the sealable member 106 when the closure device 100 is in the sealing position. In certain embodiments, and as shown in FIG. 3A, the engagement portion 124 comprises a cavity 124 in the column 122 to allow an extra-luminal pin (as the guard member 126) to be inserted therethrough.

Examples of the extra-luminal pin are described U.S. Patent Application Publication No. US 2014/0018847, titled "Percutaneous Perforation Closure Systems, Devices, and Methods." In other embodiments, the engagement portion 124 is a protrusion or a recess on the exterior surface of the column 122 to which a slotted cage or shoe (as a guard member) can engage.

In certain embodiments, the base 120 of the support member 118 has a uniform thickness between about 0.1 mm and about 1.5 mm, including 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, 1.25, 1.30, 1.35, 1.40, 1.45, and 1.5 mm. In other embodiments, the thickness is varying.

The sealable member 106, in some embodiments, is sized to be larger than the diameter of the aperture (e.g., between 12 F and 30 F). In some embodiments, the sealable member 106 has a thickness preferably between about 0.05 mm and about 0.6 mm. In some embodiments, the sealable member 106 has a thickness between about 0.005 mm and 4 mm, e.g., depending on the size of the aperture and the size of the vessel/lumen.

In certain embodiments, the thickness of the sealable member and/or support member, as deployed in the vessel/lumen, is selected based on the size of the aperture to be sealed and/or the size of the blood vessel/hollow vessel. Table 1 lists exemplary ranges of thicknesses of a sealable member to close an aperture based on the aperture/incision size that is formed. Table 2 lists exemplary ranges of thicknesses of the sealable member to close an aperture based on the vessel diameter size. Table 3 lists exemplary ranges of thicknesses of sealable member to close an aperture base on the size of the hollow vessel.

TABLE 1

Example thicknesses of a sealable member for closure of a blood vessel (e.g., having an internal diameter between about 6 and 12 mm), selected based on the incision/puncture size at the blood vessel.

| French size | Hole Size (mm) | Sealable Member Thickness (mm) | |
|---|---|---|---|
| | | Min | Max |
| 6 | 2 | 0.04 | 0.5 |
| 9 | 3 | 0.04 | 0.75 |
| 12 | 4 | 0.04 | 1 |
| 15 | 5 | 0.04 | 1.5 |
| 18 | 6 | 0.04 | 2 |
| 21 | 7 | 0.04 | 2.5 |
| 24 | 8 | 0.04 | 3 |
| 27 | 9 | 0.04 | 4 |

TABLE 2

Example thicknesses of a sealable member for closure of a blood vessel, selected based on the size of the blood vessel.

| Vessel Size (Internal Diameter, mm) | Sealable Member Thickness (mm) | |
|---|---|---|
| | Min | Max |
| 5 | 0.04 | 0.5 |
| 6 | 0.04 | 0.75 |
| 7 | 0.04 | 1 |
| 9 | 0.04 | 1.5 |
| 11 | 0.04 | 2 |
| 15 | 0.04 | 3 |
| 20 | 0.04 | 3.5 |
| 30 | 0.04 | 4 |

TABLE 3

Example thicknesses of a sealable member for closure of a non-blood carrying hollow vessel (e.g., having an internal diameter between 15 and 100+ mm), selected based on the size of the hollow vessel.

| Vessel Size (Internal Diameter, mm) | Sealable Member Thickness (mm) | |
|---|---|---|
| | Min | Max |
| 15 | 0.04 | 3 |
| 40 | 0.04 | 8 |
| >100 | 0.04 | 20+ |

The sealable member 106 is preferably circular in shape. It should be understood, however, that other geometries may be provided for the hole and/or the disk portion, including, but not limited to, ovals. The sealable member 106 has a hole (e.g., located at or near the center of the member) sized to accept the column 122. In some embodiments, the sealable member 106 is free to rotate relative to the base 120 of the support member 118 about an axis concentric to the column 122. Other examples of the sealable member is described in U.S. Patent Application Publication No. US 2014/0018847, titled "Percutaneous Perforation Closure Systems, Devices, and Methods," and U.S. Provisional Application No. 62/092,212, titled "Implantable Sealable Member with Mesh Layer," the content of each of these applications is incorporated by reference herein in its entirety.

The sealable member and/or the base comprises, in some embodiments, at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the sealable member and/or the base is a copolymer of Polydioxanone, Poly-L-lactide, Poly-D-lactide, Poly-DL-lactide, Polyglycolide, ε-Caprolactone, and Polyethylene glycol. In some embodiments, the copolymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable. One of ordinary skill in the art will appreciate that other suitable biodegradable material may be employed.

In certain embodiments, the thickness of the support member 118 and the sealable member 106 are selected such that the members 106, 118 are bendable to be loaded into the cannula 2202 while having sufficient rigidity to form and maintain a tamponade at the aperture when the device 100 is in the sealing position. In some embodiments, the thickness of the support member 118 and the sealable member 106 are selected such that a portion of the members 106, 118 is rigid.

Figure 21A:
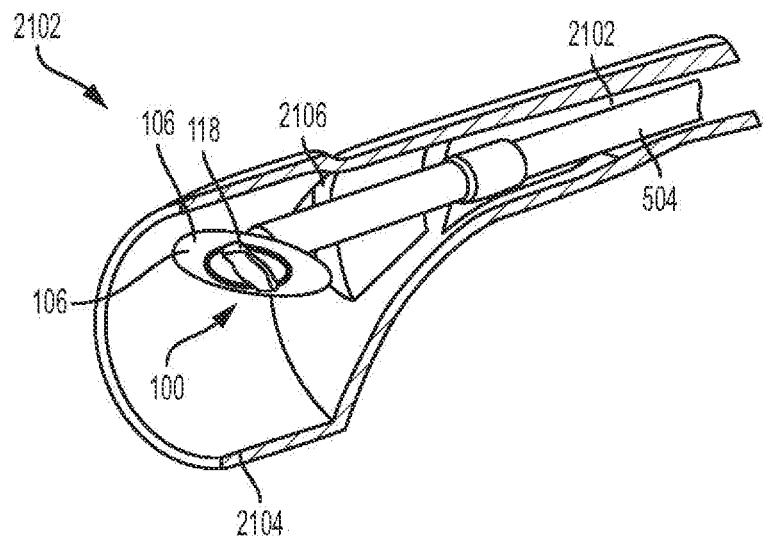
FIGS. 21A, 21B, and 21C are diagrams showing a sequence of the transition of the sealable member and the support member from a stowed state to a delivery state when the closure apparatus is loaded in a delivery cannula.
Figure 21B:
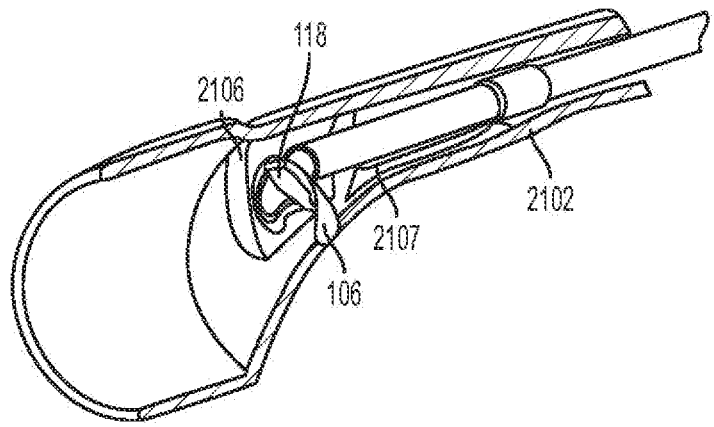
Figure 21C:
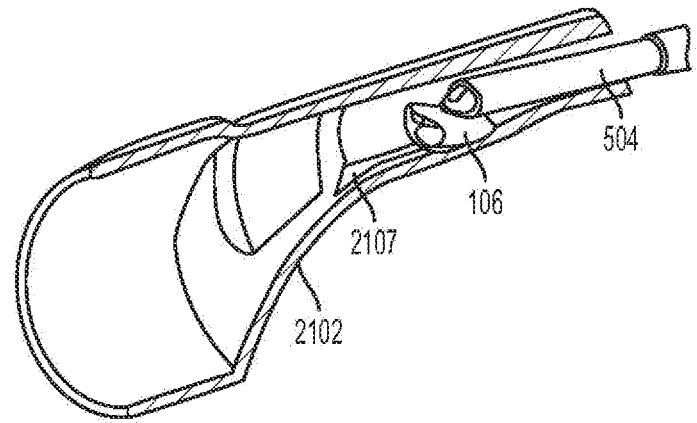

In some embodiments, the base 120 of the support member 118 is sufficiently flexible to roll into a delivery funnel used for delivering the implant into the body lumen. FIGS. 21A, 21B, and 21C are diagrams showing a sequence of the transition, in some embodiments, of the sealable member and the support member from a stowed state to a delivery state when the closure apparatus is loaded in a delivery cannula.

In some embodiments, during deployment to close a hole, e.g., in a hollow vessel, the implant 100 is loaded into a delivery cannula 2102 through a loading funnel 2102 which reduces the cross-sectional area of the implant 100 (e.g., support member 118 and sealable member 106) to make it possible to deliver the implant through an introducer catheter into a hollow vessel (such as an artery or a vein) within which there had been made an access hole to perform a minimally invasive procedure. During this delivery and deployment of the implant, the support member 118 (e.g., O-ring foot core) supports the wing.

As shown in FIG. 21A, the device 100 is in an open configuration. The sealable member 106 and the base 120 are in a resting state. It should be appreciated that in certain embodiments, the base 120 may be pre-loaded to bias the sealable member 106 when in the resting state.

FIG. 21B shows the sealable member 106 and the base 120 of the support member 118 progressively folded down as they pass proximally through a narrowing zone 2106 of the funnel 2102. In certain embodiments, the narrowing zone 2106 includes a first offset surface to initiate folding of the sealable member 106 along one of its side. A second offset surface then initiates folding of the other side as the support member 118 continues to pass through the funnel 2102. The different initiation of the folding of the base 120 and sealable member 106 ensures that they fold in an overlapping manner. In some embodiments, the funnel 2102 includes a third surface 2107.

Figure 22:
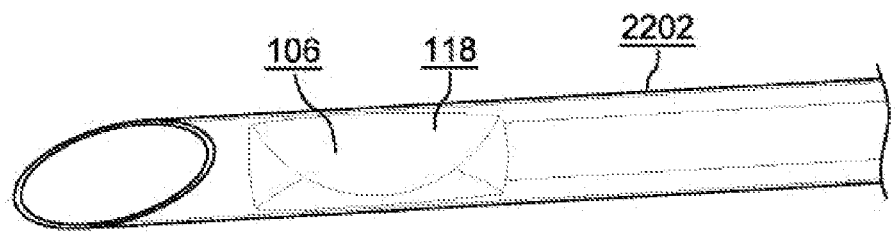
FIG. 22 is a diagram of the sealable member and the support member in the delivery configuration.
Figure 23A:
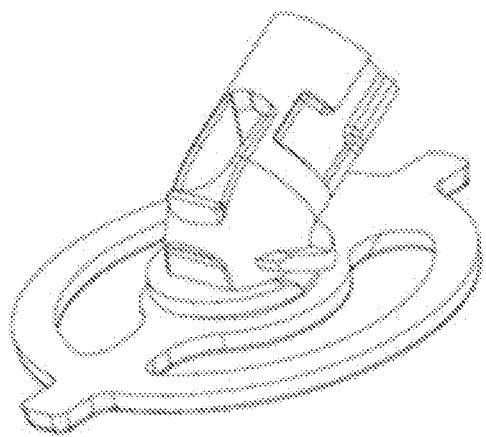
FIGS. 23A, 23B, 23C, and 23D are diagrams of perspective, top, front, and side views of an illustrative embodiment of a closure apparatus.
Figure 23B:
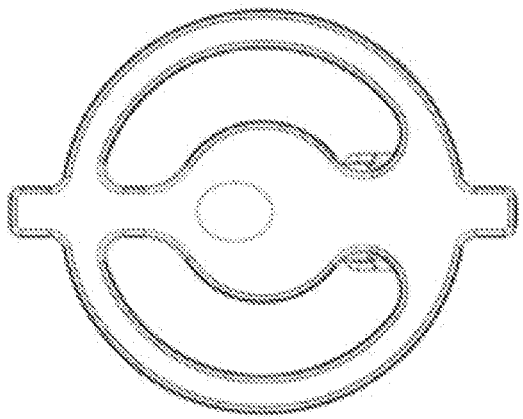
Figure 23C:
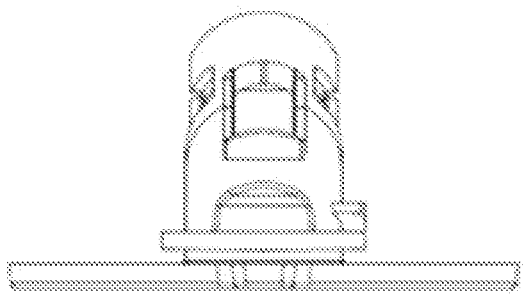
Figure 23D:
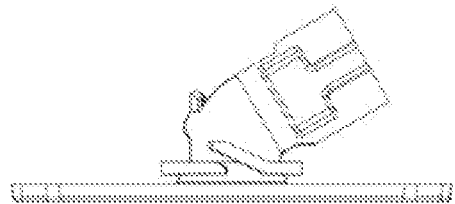
Figure 24A:
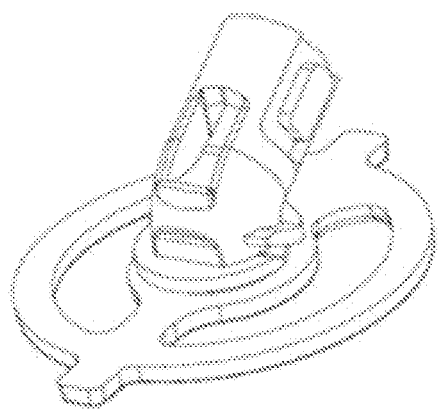
FIGS. 24A, 24B, 24C, and 24D are diagrams of perspective, top, front, and side views of an illustrative embodiment of a closure apparatus.
Figure 24B:
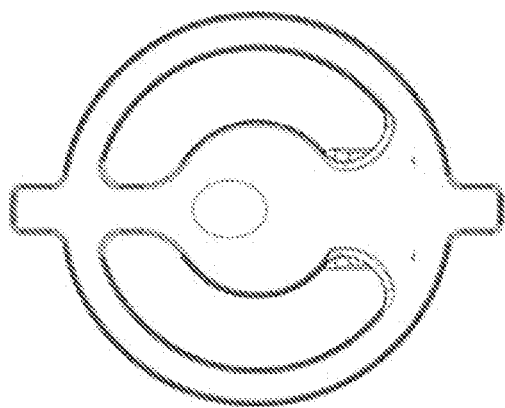
Figure 24C:
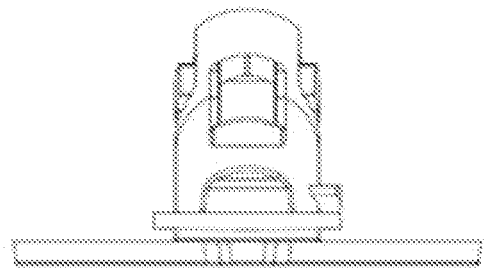
Figure 24D:
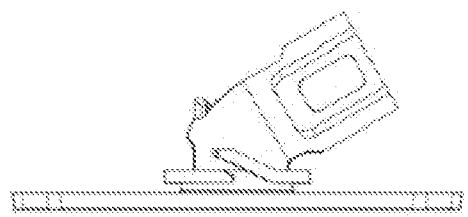
Figure 25A:
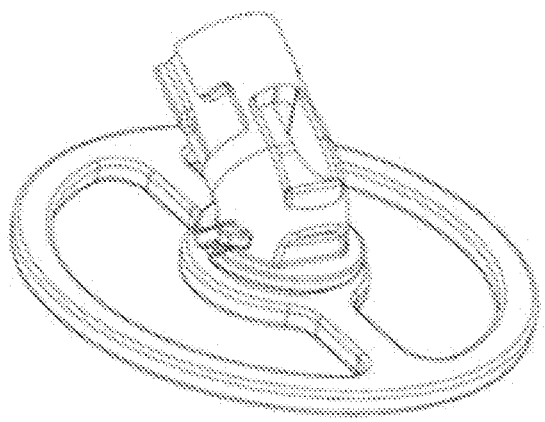
FIGS. 25A, 25B, 25C, and 25D are diagrams of perspective, top, front, and side views of an illustrative embodiment of a closure apparatus.
Figure 25B:
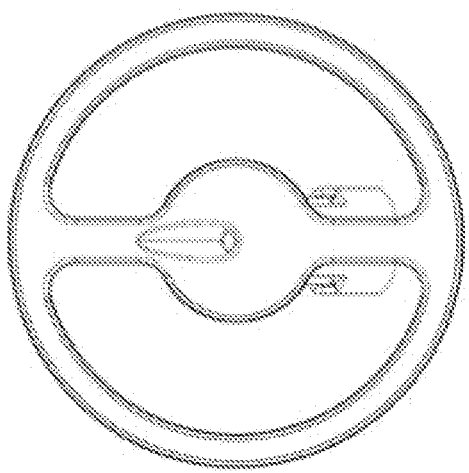
Figure 25C:
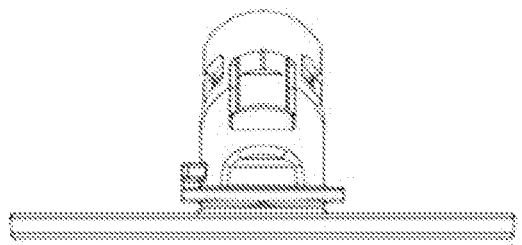
Figure 25D:
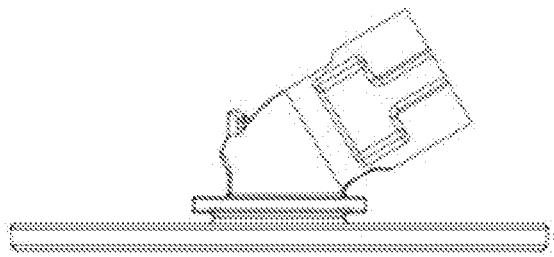
Figure 26A:
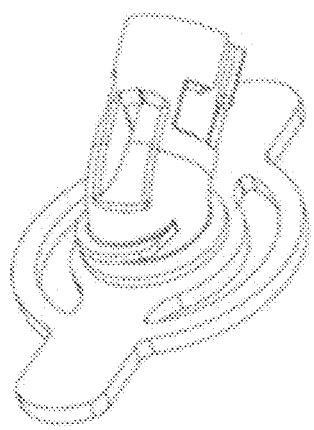
FIGS. 26A, 26B, 26C, and 26D are diagrams of perspective, top, front, and side views of an illustrative embodiment of a closure apparatus.
Figure 26B:
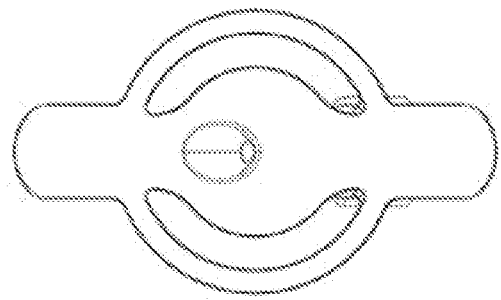
Figure 26C:
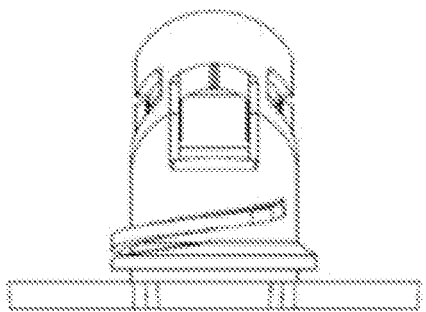
Figure 26D:
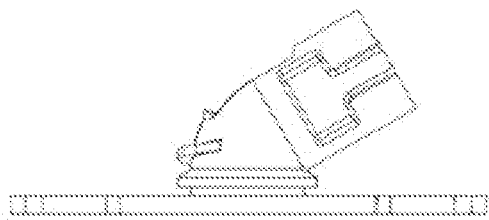
Figure 27A:
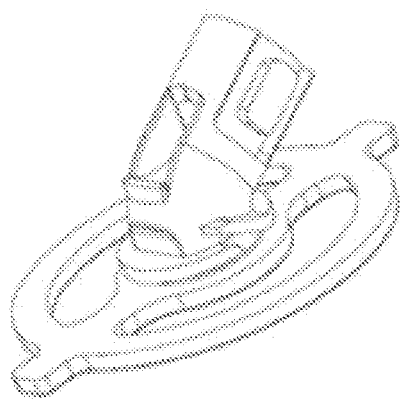
FIGS. 27A, 27B, 27C, and 27D are diagrams of perspective, top, front, and side views of an illustrative embodiment of a closure apparatus.
Figure 27B:
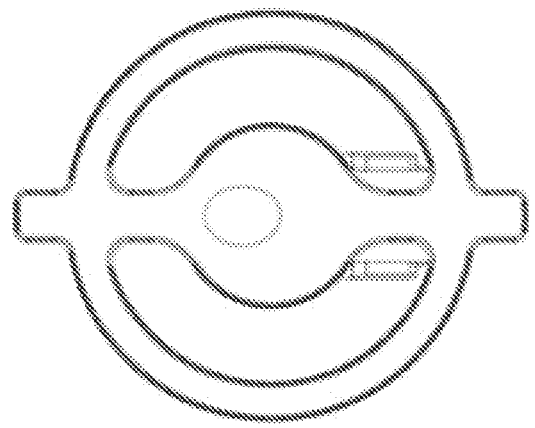
Figure 27C:
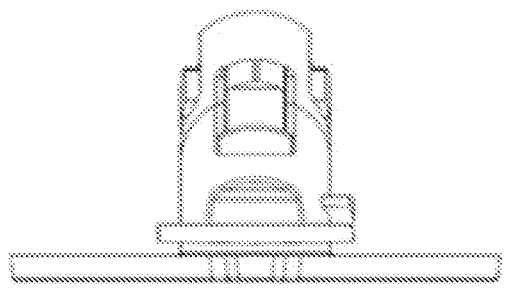
Figure 27D:
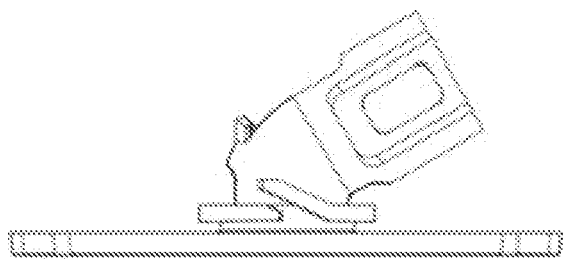
Figure 28A:
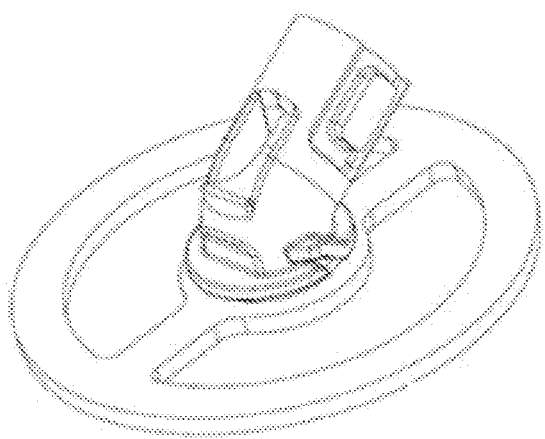
FIGS. 28A, 28B, 28C, and 28D are diagrams of perspective, top, front, and side views of an illustrative embodiment of a closure apparatus.
Figure 28B:
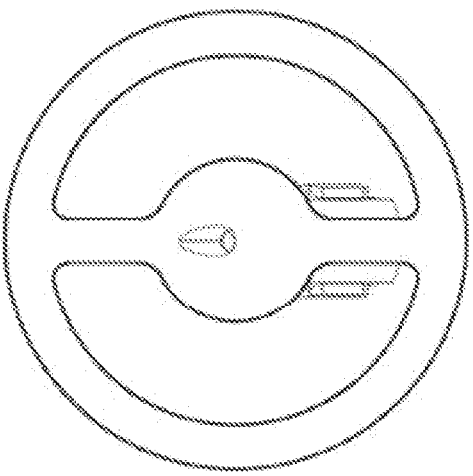
Figure 28C:
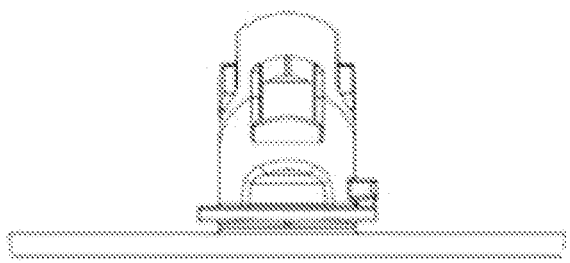
Figure 28D:
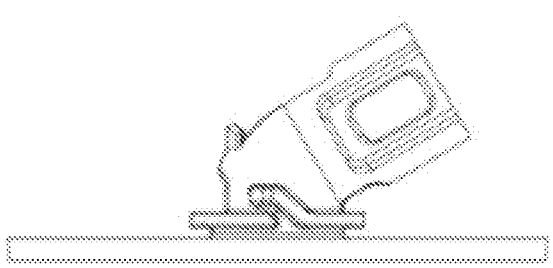
Figure 29A:
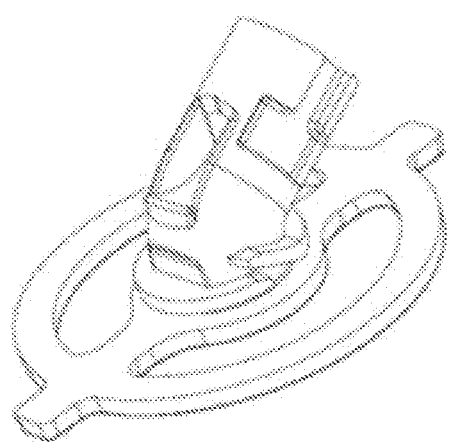
FIGS. 29A, 29B, 29C, and 29D are diagrams of perspective, top, front, and side views of an illustrative embodiment of a closure apparatus.
Figure 29B:
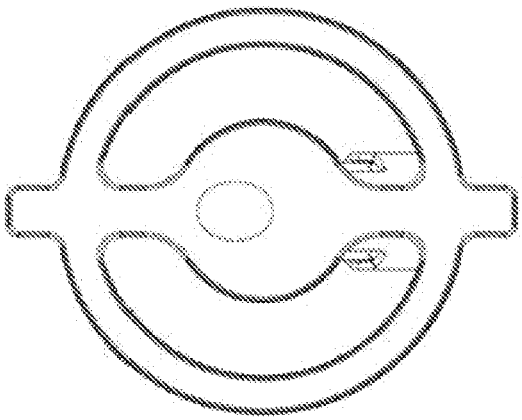
Figure 29C:
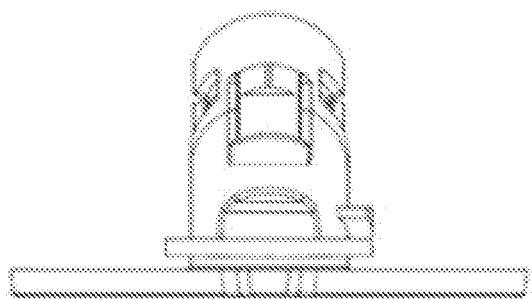
Figure 29D:
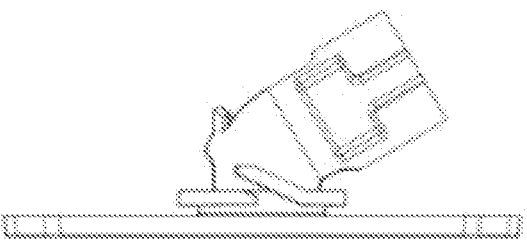
Figure 30A:
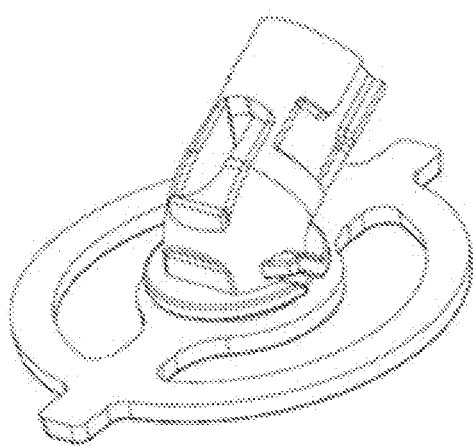
FIGS. 30A, 30B, 30C, and 30D are diagrams of perspective, top, front, and side views of an illustrative embodiment of a closure apparatus.
Figure 30B:
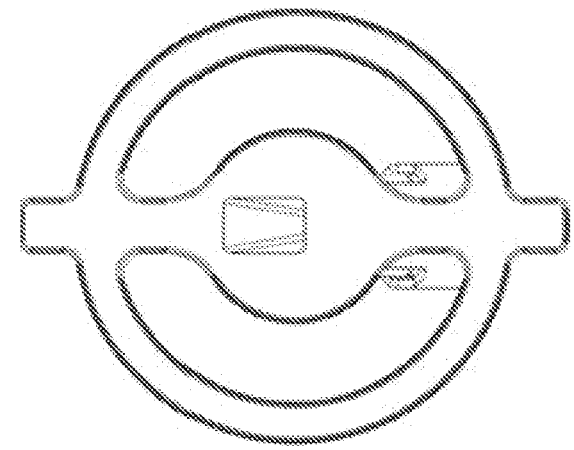
Figure 30C:
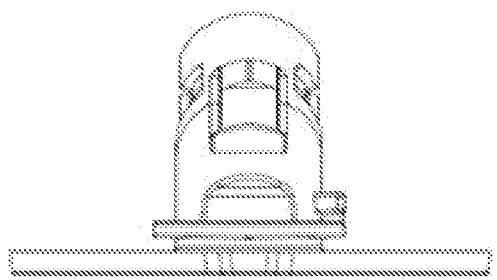
Figure 30D:
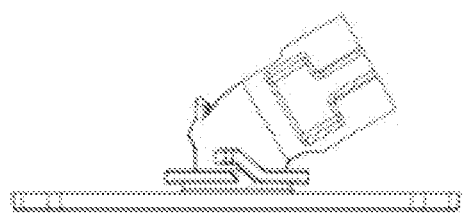
Figure 31A:
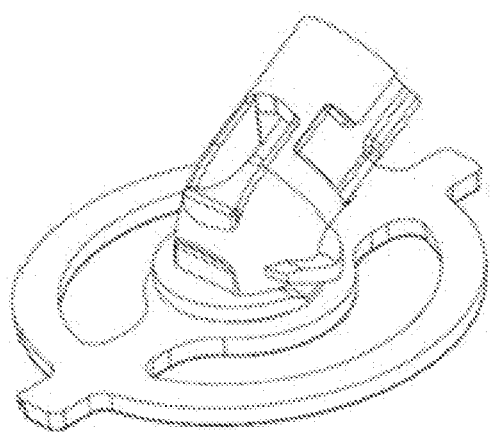
FIGS. 31A, 31B, 31C, and 31D are diagrams of perspective, top, front, and side views of an illustrative embodiment of a closure apparatus.
Figure 31B:
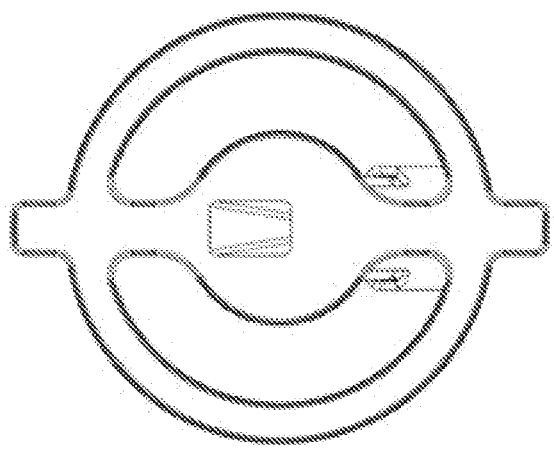
Figure 31C:
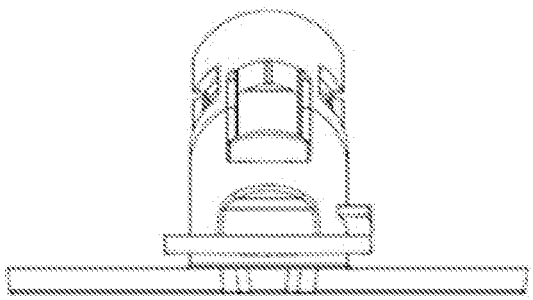
Figure 31D:
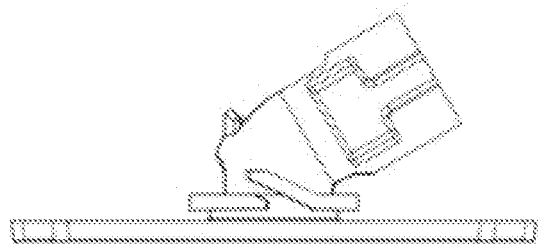
Figure 33A:
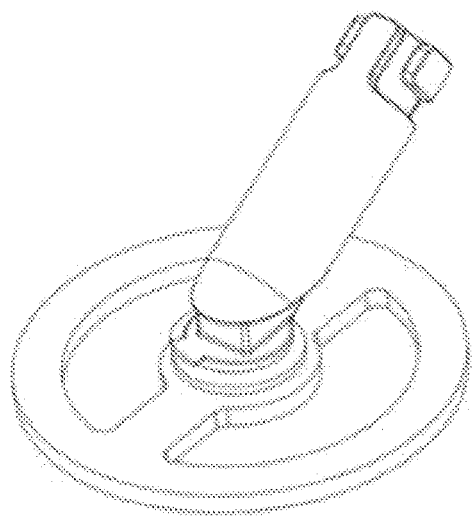
FIGS. 33A, 33B, 33C, and 33D are diagrams of perspective, top, front, and side views of an illustrative embodiment of a closure apparatus.
Figure 33B:
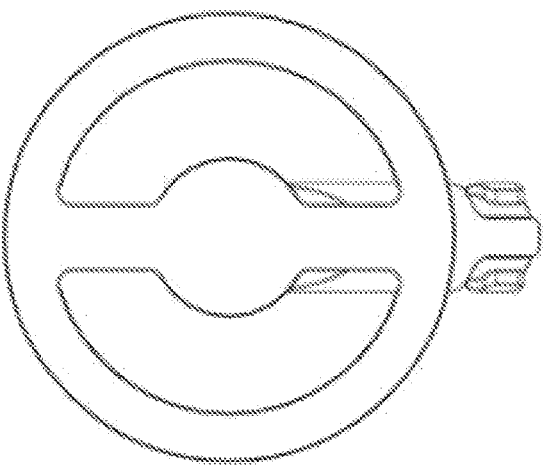
Figure 33C:
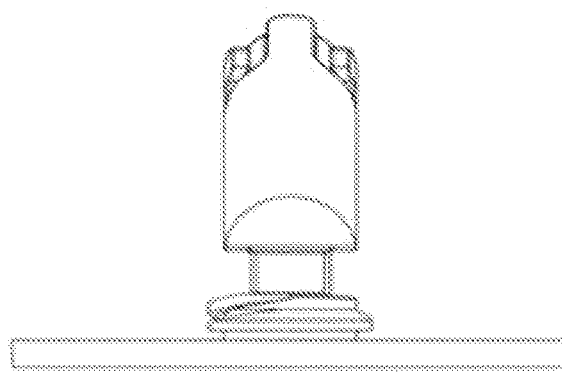
Figure 33D:
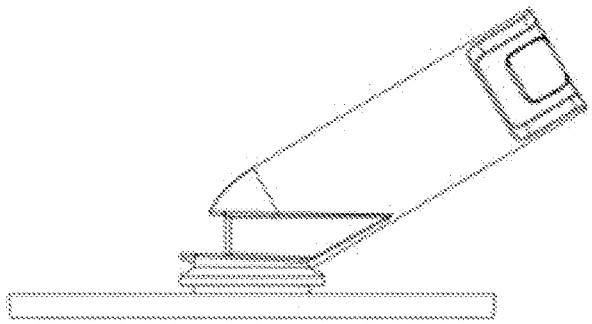
Figure 34A:
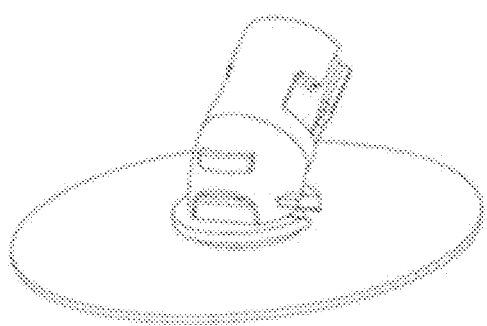
FIGS. 34A, 34B, 34C, and 34D are diagrams of perspective, top, front, and side views of an illustrative embodiment of a closure apparatus.
Figure 34B:
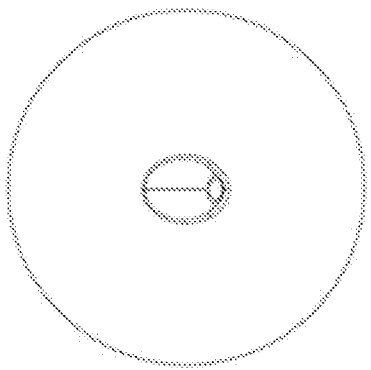
Figure 34C:
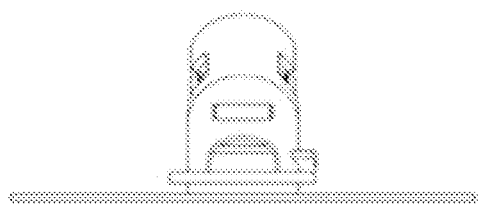
Figure 34D:
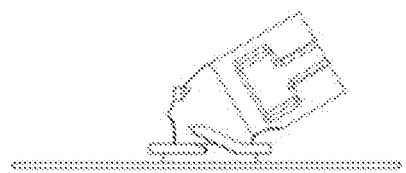
Figure 35A:
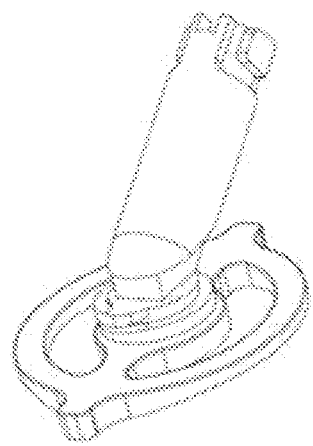
FIGS. 35A, 35B, 35C, and 35D are diagrams of perspective, top, front, and side views of an illustrative embodiment of a closure apparatus.
Figure 35B:
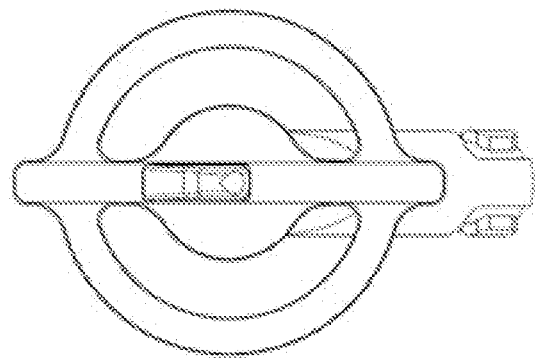
Figure 35C:
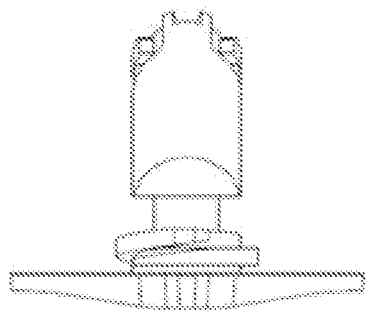
Figure 35D:
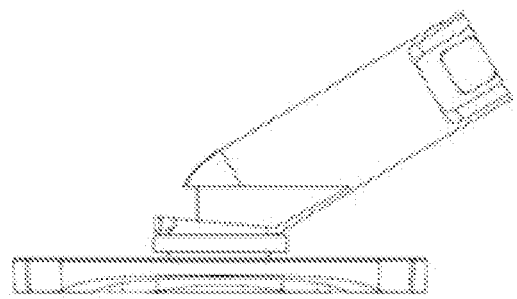
Figure 36A:
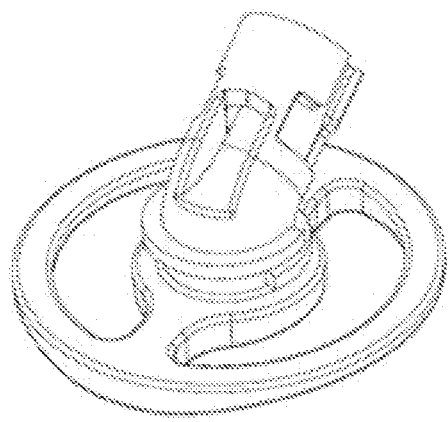
FIGS. 36A, 36B, 36C, and 36D are diagrams of perspective, top, front, and side views of an illustrative embodiment of a closure apparatus.
Figure 36B:
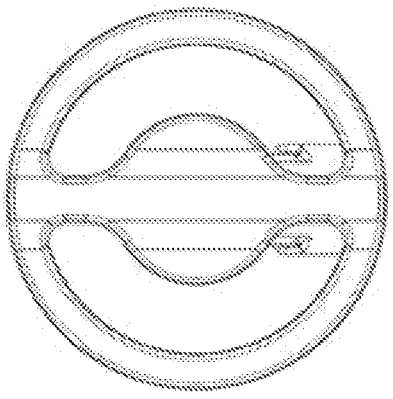
Figure 36C:
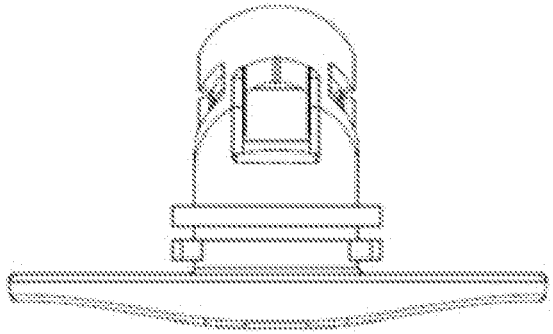
Figure 36D:
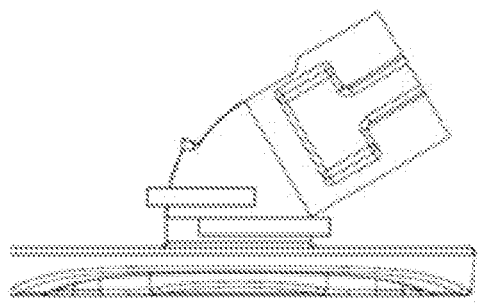
Figure 37A:
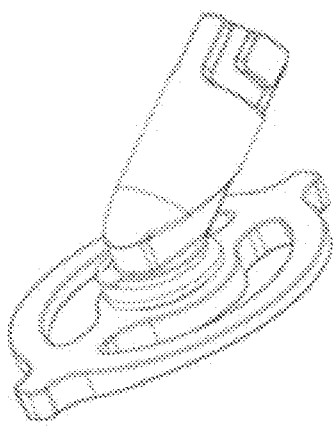
FIGS. 37A, 37B, 37C, and 37D are diagrams of perspective, top, front, and side views of an illustrative embodiment of a closure apparatus.
Figure 37B:
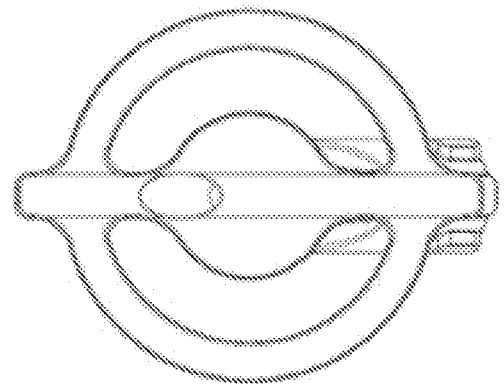
Figure 37C:
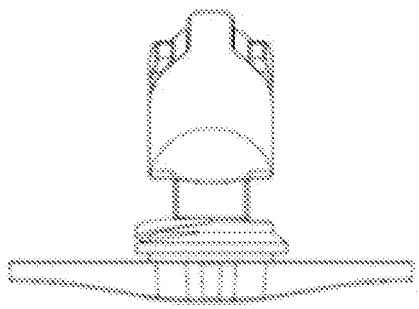
Figure 37D:
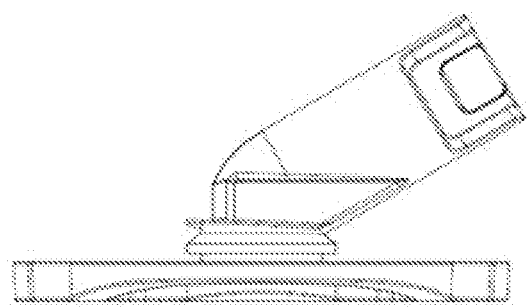
Figure 38A:
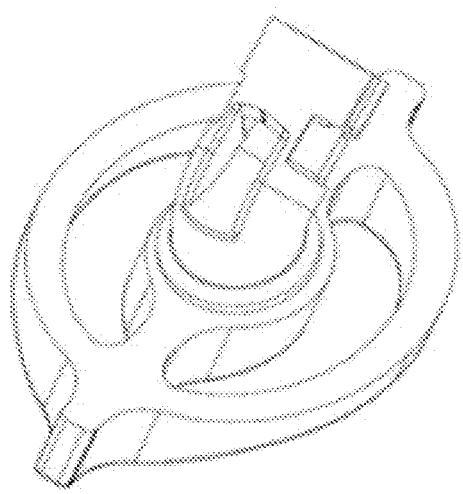
FIGS. 38A, 38B, 38C, and 38D are diagrams of perspective, top, front, and side views of an illustrative embodiment of a closure apparatus.
Figure 38B:
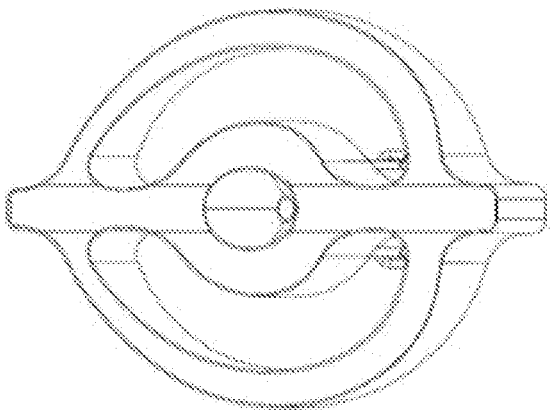
Figure 38C:
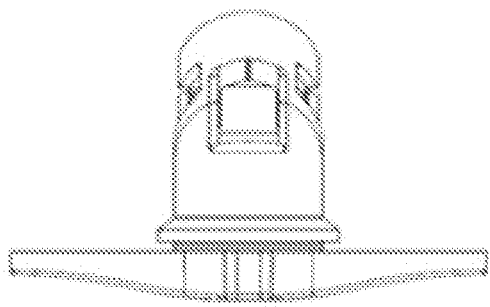
Figure 38D:
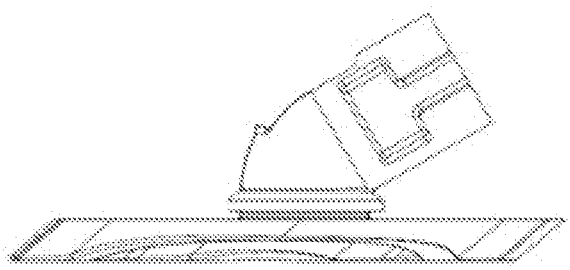
Figure 39A:
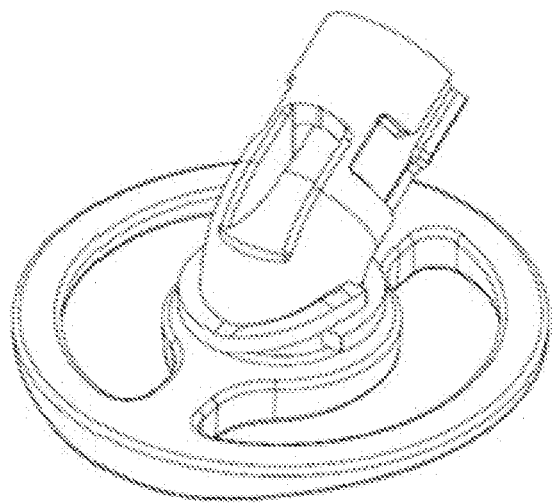
FIGS. 39A, 39B, 39C, and 39D are diagrams of perspective, top, front, and side views of an illustrative embodiment of a closure apparatus.
Figure 39B:
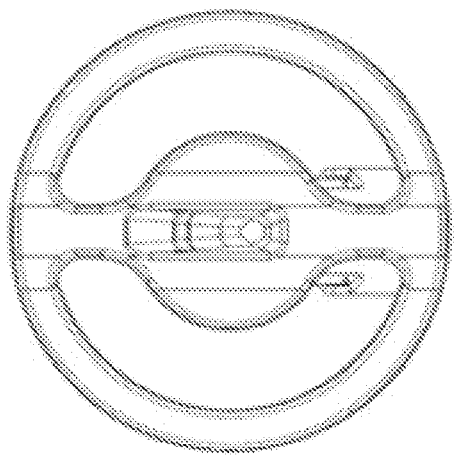
Figure 39C:
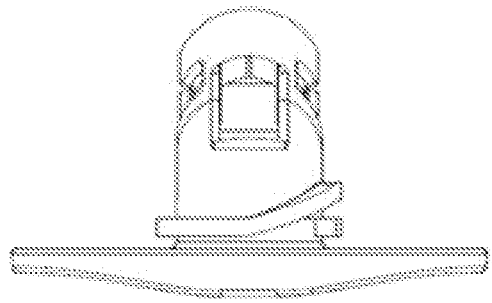
Figure 39D:
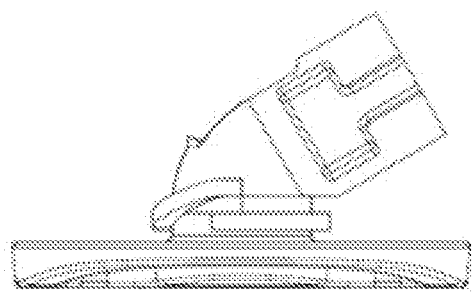
Figure 40A:
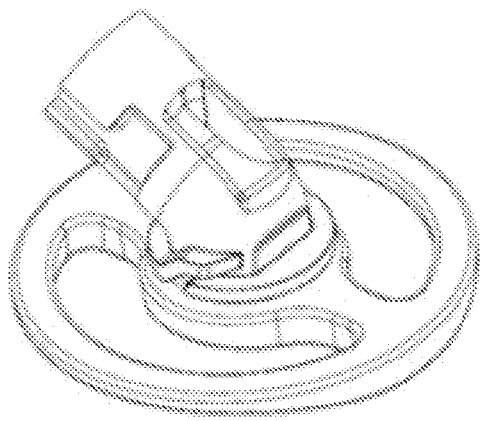
FIGS. 40A, 40B, 40C, and 40D are diagrams of perspective, top, front, and side views of an illustrative embodiment of a closure apparatus.
Figure 40B:
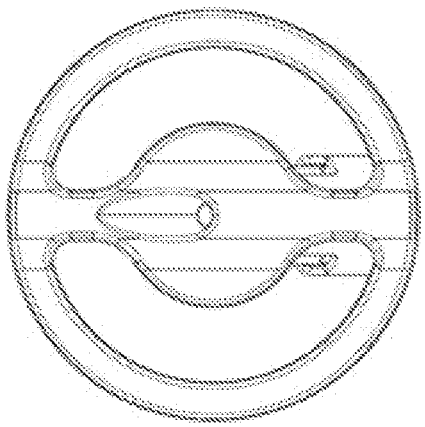
Figure 40C:
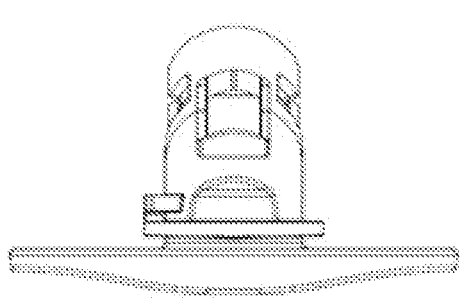
Figure 40D:
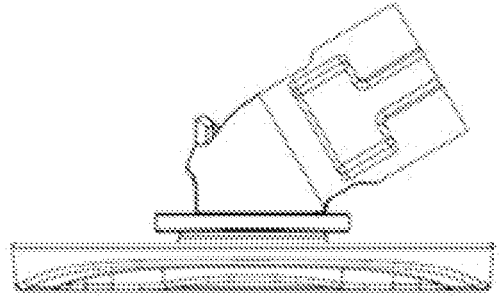
Figure 41A:
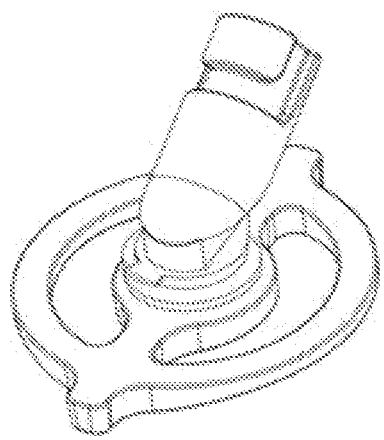
FIGS. 41A, 41B, 41C, and 41D are diagrams of perspective, top, front, and side views of an illustrative embodiment of a closure apparatus.
Figure 41B:
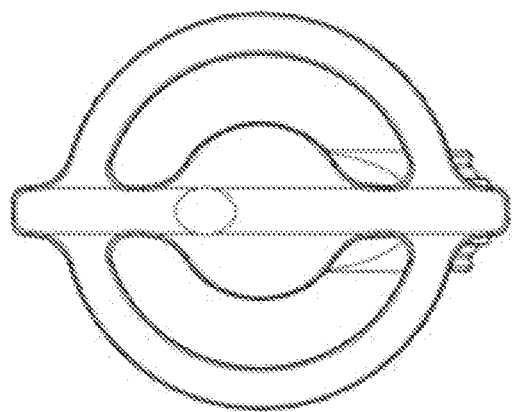
Figure 41C:
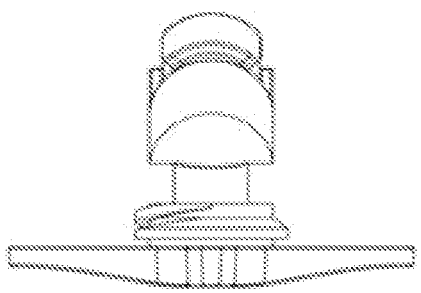
Figure 41D:
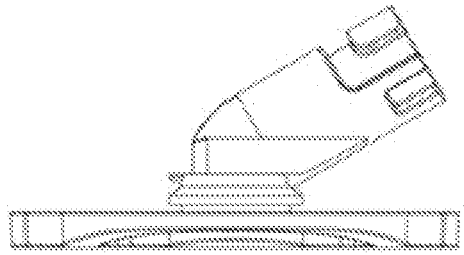
Figure 42A:
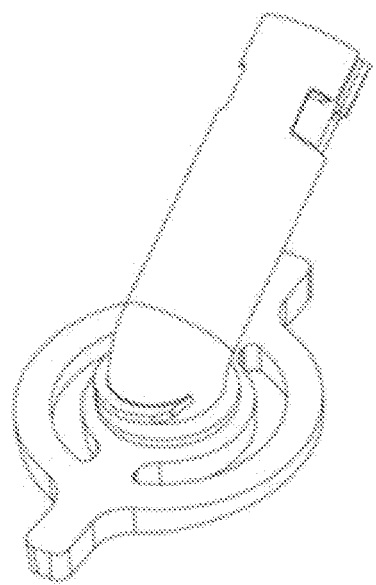
FIGS. 42A, 42B, 42C, and 42D are diagrams of perspective, top, front, and side views of an illustrative embodiment of a closure apparatus.
Figure 42B:
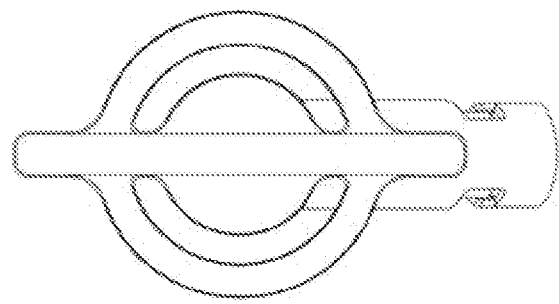
Figure 42C:
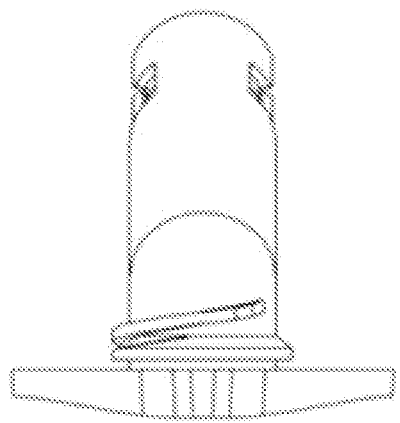
Figure 42D:
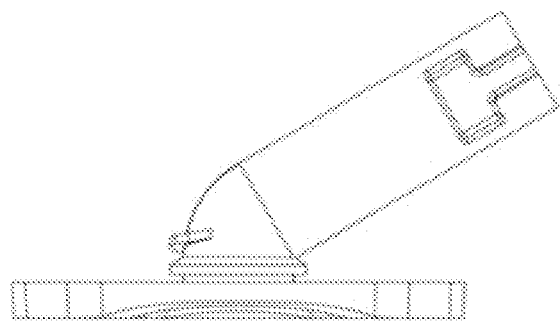
Figure 43A:
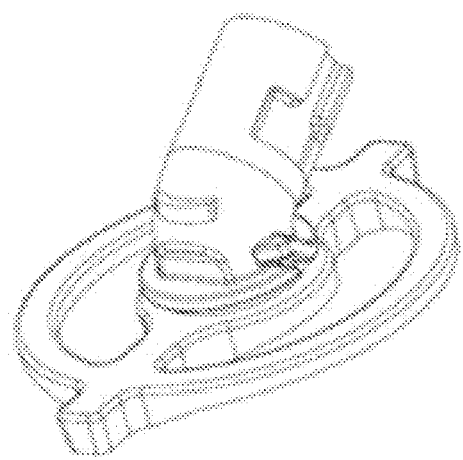
FIGS. 43A, 43B, 43C, and 43D are diagrams of perspective, top, front, and side views of an illustrative embodiment of a closure apparatus.
Figure 43B:
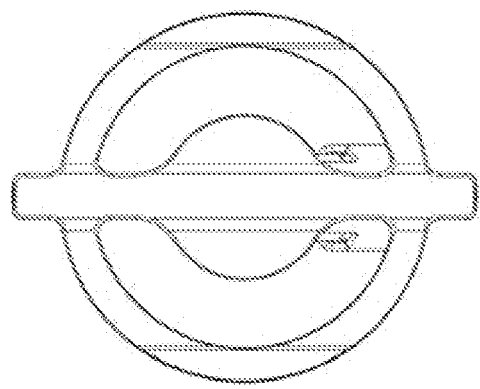
Figure 43C:
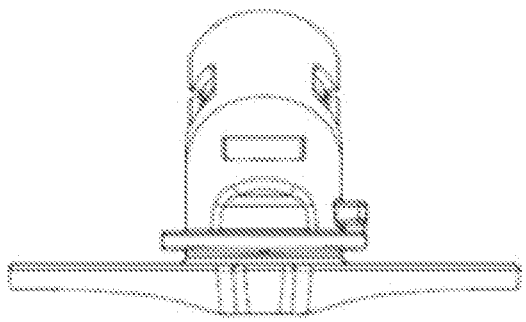
Figure 43D:
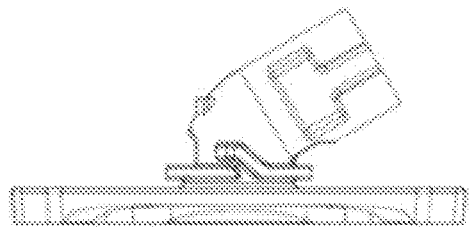
Figure 44A:
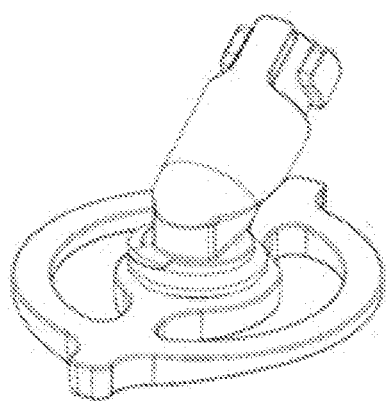
FIGS. 44A, 44B, 44C, and 44D are diagrams of perspective, top, front, and side views of an illustrative embodiment of a closure apparatus.
Figure 44B:
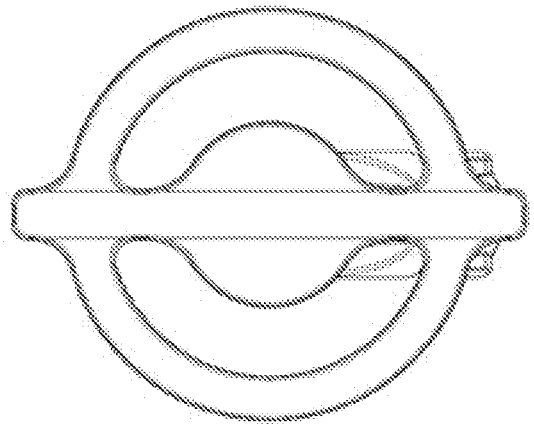
Figure 44C:
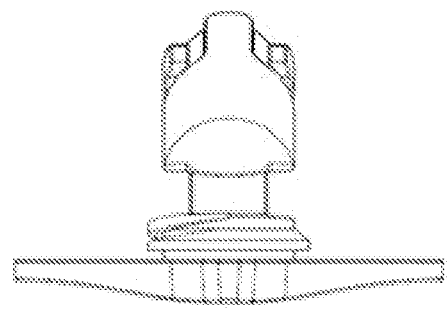
Figure 44D:
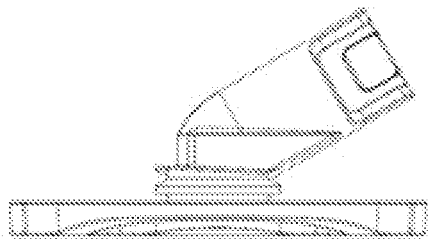
Figure 46A:
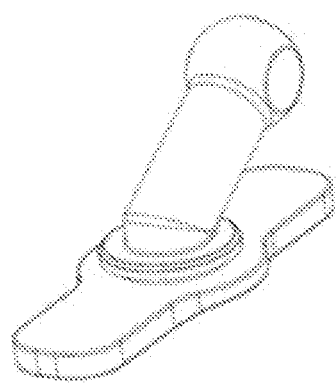
FIGS. 46A, 46B, 46C, and 46D are diagrams of perspective, top, front, and side views of an illustrative embodiment of a closure apparatus.
Figure 46B:
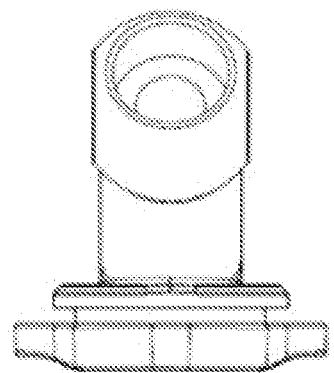
Figure 46C:
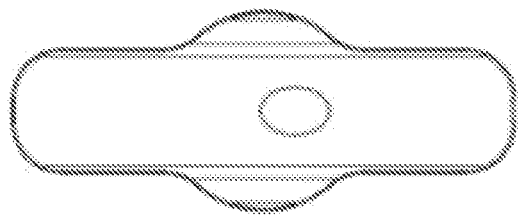
Figure 46D:
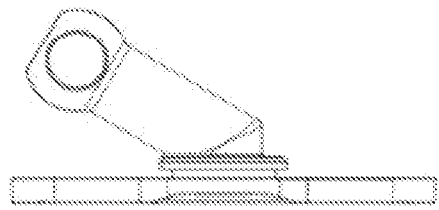
Figure 47A:
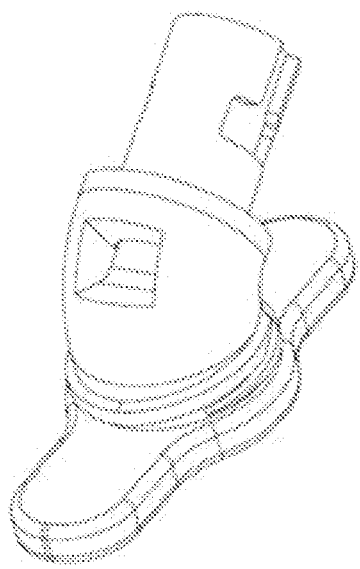
FIGS. 47A, 47B, 47C, and 47D are diagrams of perspective, top, front, and side views of an illustrative embodiment of a closure apparatus.
Figure 47B:
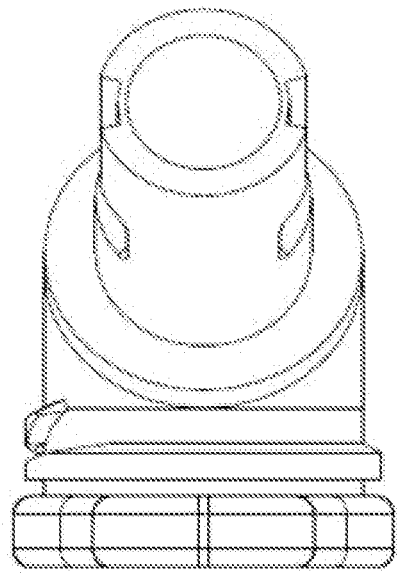
Figure 47C:
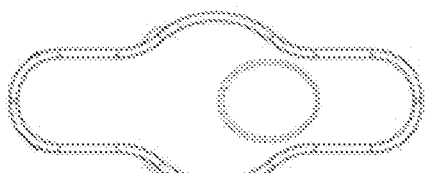
Figure 47D:
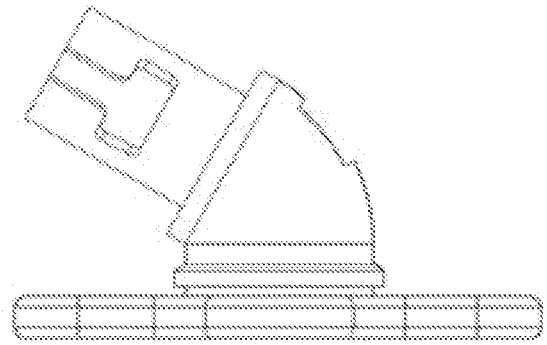
Figure 48A:
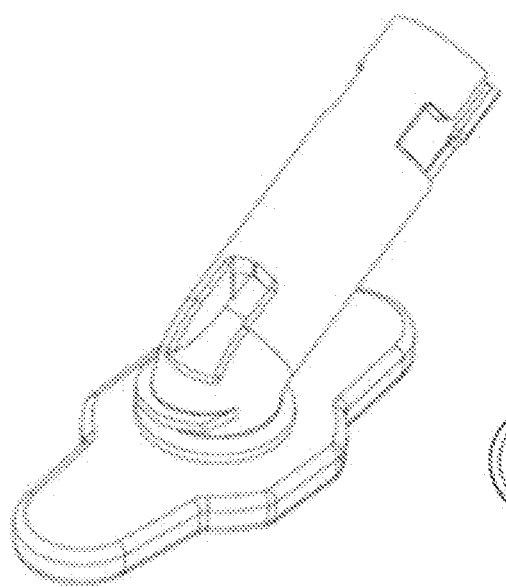
FIGS. 48A, 48B, 48C, and 48D are diagrams of perspective, top, front, and side views of an illustrative embodiment of a closure apparatus.
Figure 48B:
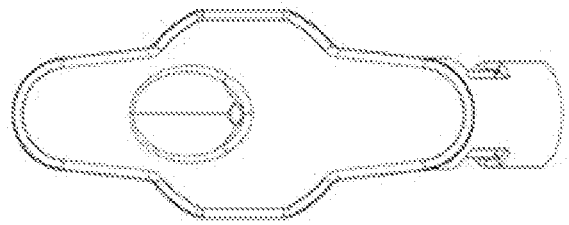
Figure 48C:
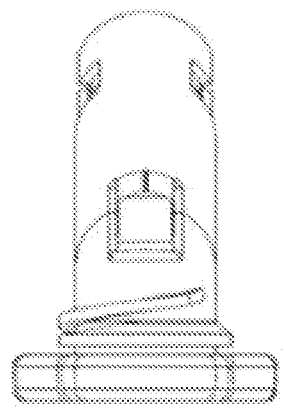
Figure 48D:
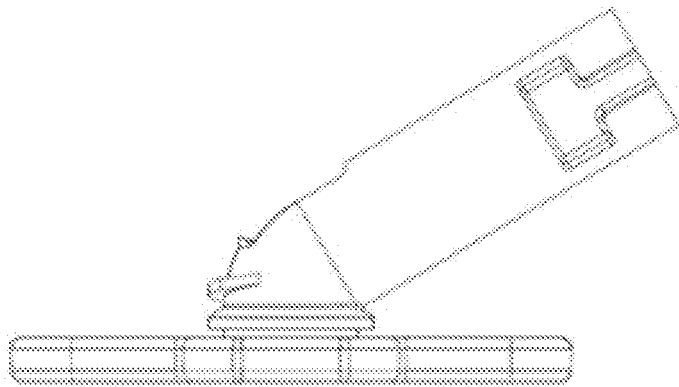
Figure 49A:
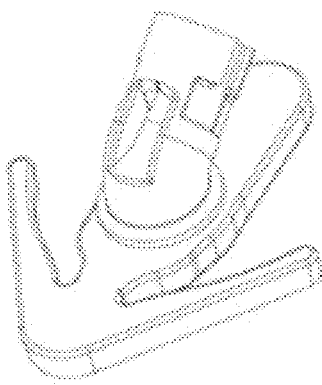
FIGS. 49A, 49B, 49C, and 49D are diagrams of perspective, top, front, and side views of an illustrative embodiment of a closure apparatus.
Figure 49B:
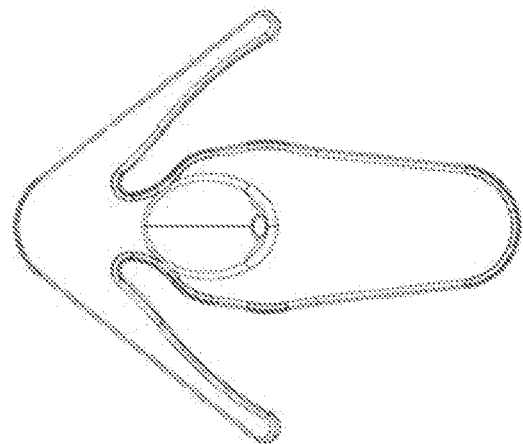
Figure 49C:
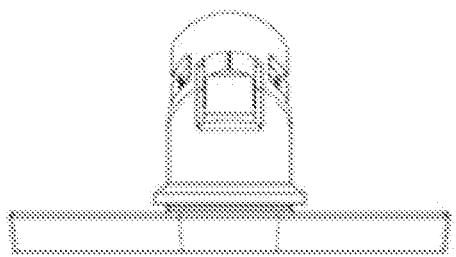
Figure 49D:
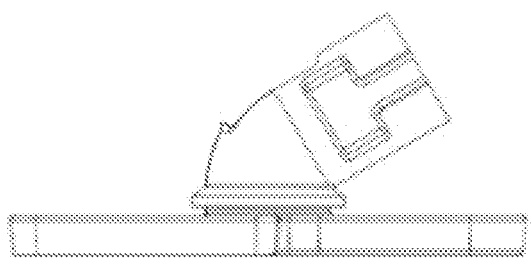
Figure 50A:
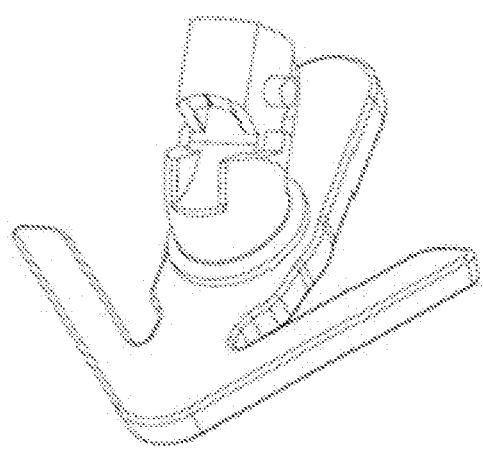
FIGS. 50A, 50B, 50C, and 50D are diagrams of perspective, top, front, and side views of an illustrative embodiment of a closure apparatus.
Figure 50B:
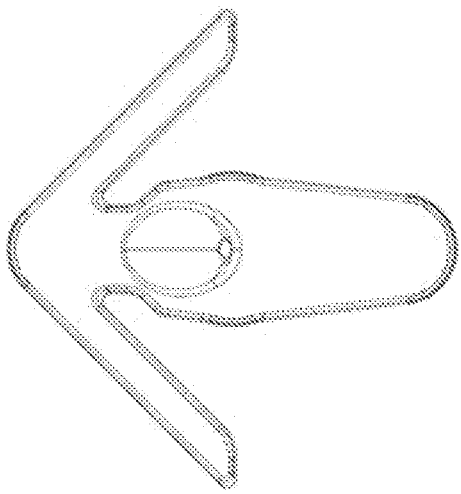
Figure 50C:
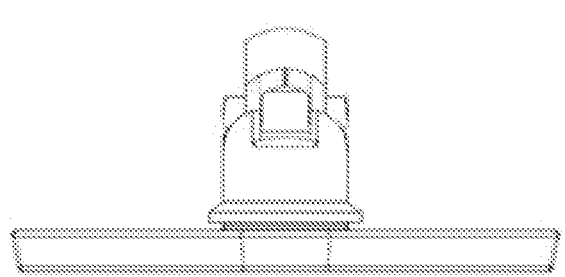
Figure 50D:
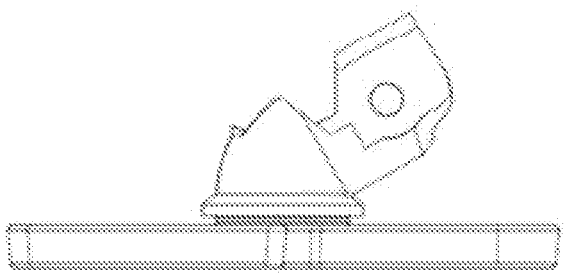
Figure 51A:
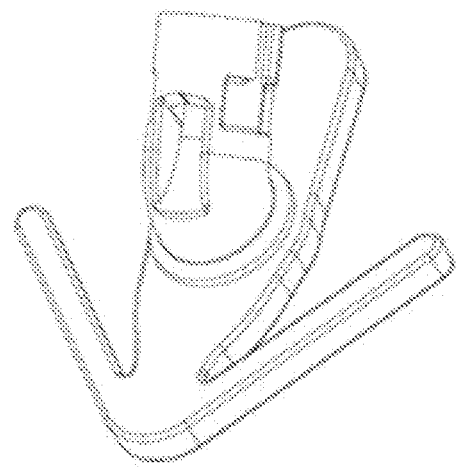
FIGS. 51A, 51B, 51C, and 51D are diagrams of perspective, top, front, and side views of an illustrative embodiment of a closure apparatus.
Figure 51B:
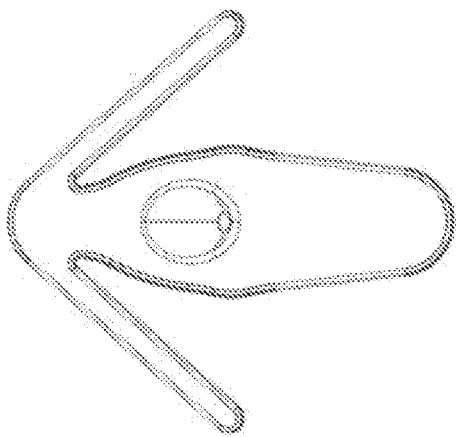
Figure 51C:
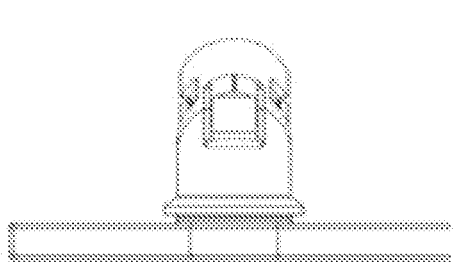
Figure 51D:
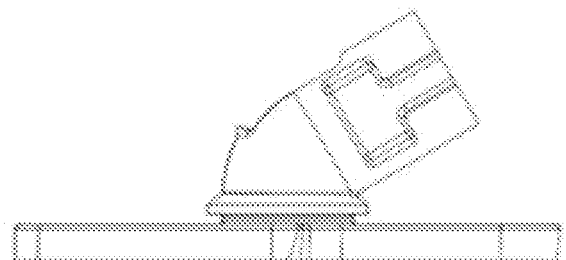
Figure 52A:
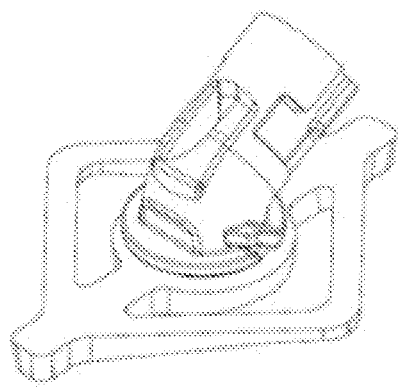
FIGS. 52A, 52B, 52C, and 52D are diagrams of perspective, top, front, and side views of an illustrative embodiment of a closure apparatus.
Figure 52B:
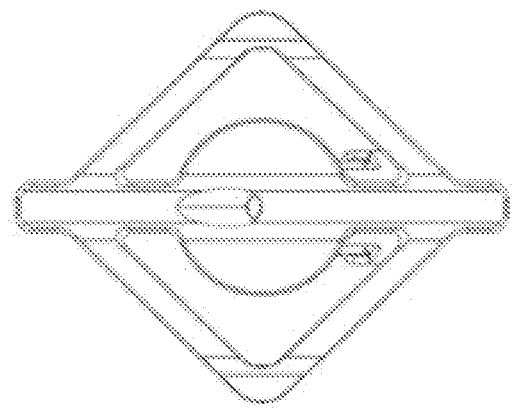
Figure 52C:
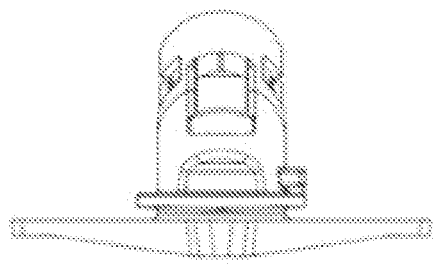
Figure 52D:
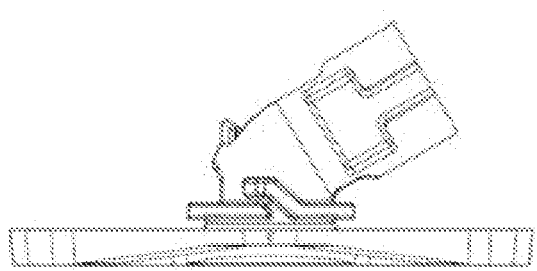
Figure 53A:
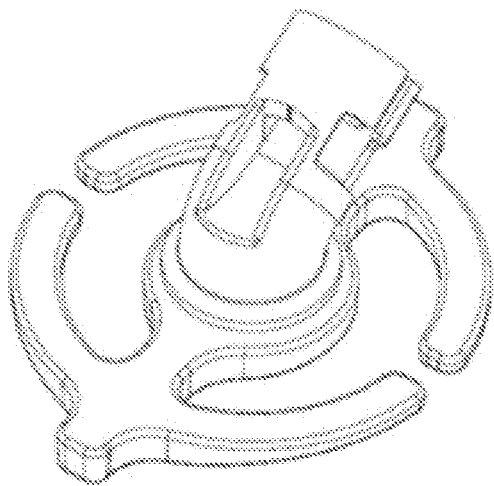
FIGS. 53A, 53B, 53C, and 53D are diagrams of perspective, top, front, and side views of an illustrative embodiment of a closure apparatus.
Figure 53B:
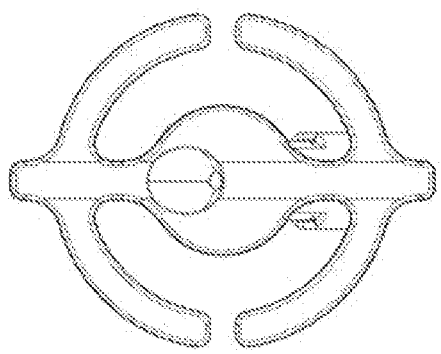
Figure 53C:
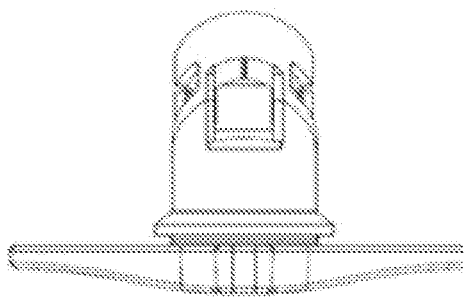
Figure 53D:
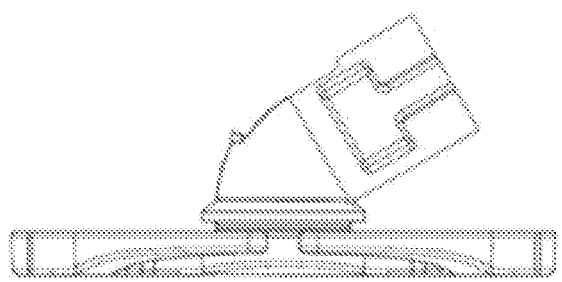
Figure 54A:
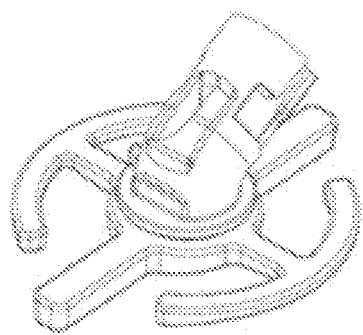
FIGS. 54A, 54B, 54C, and 54D are diagrams of perspective, top, front, and side views of an illustrative embodiment of a closure apparatus.
Figure 54B:
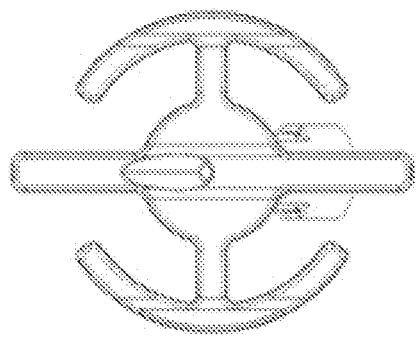
Figure 54C:
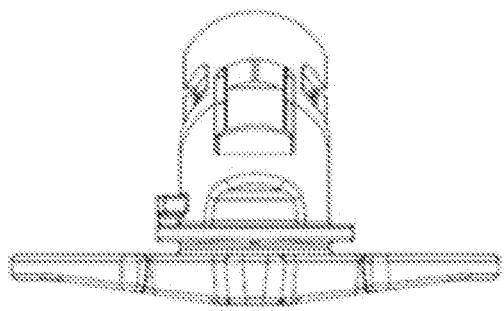
Figure 54D:
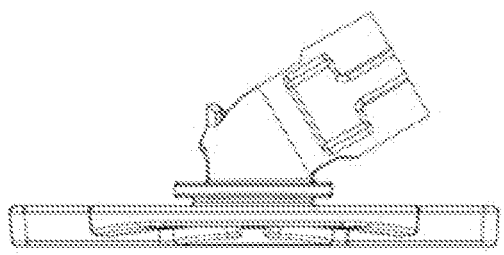
Figure 55A:
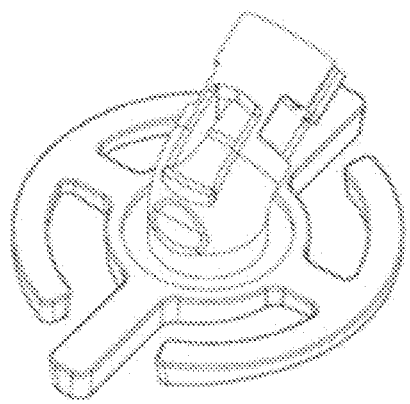
FIGS. 55A, 55B, 55C, and 55D are diagrams of perspective, top, front, and side views of an illustrative embodiment of a closure apparatus.
Figure 55B:
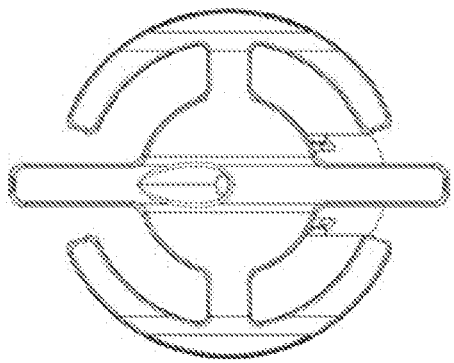
Figure 55C:
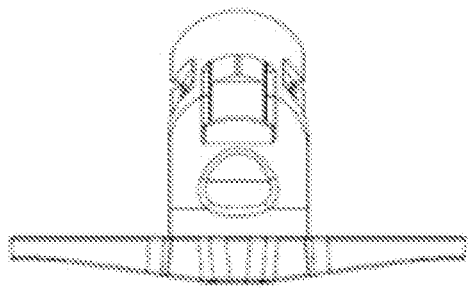
Figure 55D:
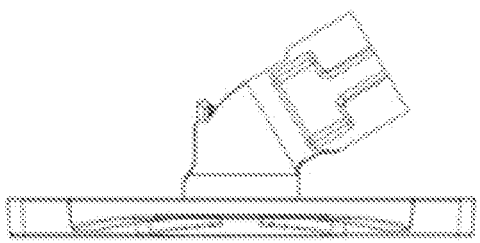
Figure 56A:
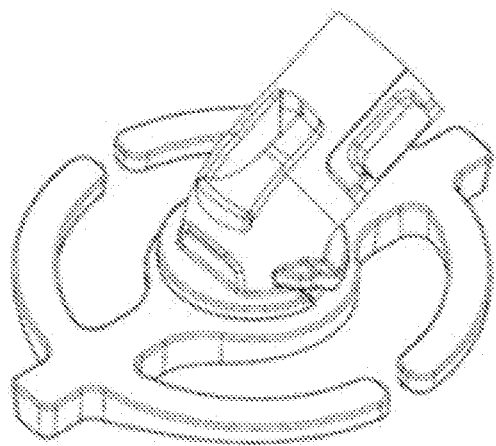
FIGS. 56A, 56B, 56C, and 56D are diagrams of perspective, top, front, and side views of an illustrative embodiment of a closure apparatus.
Figure 56B:
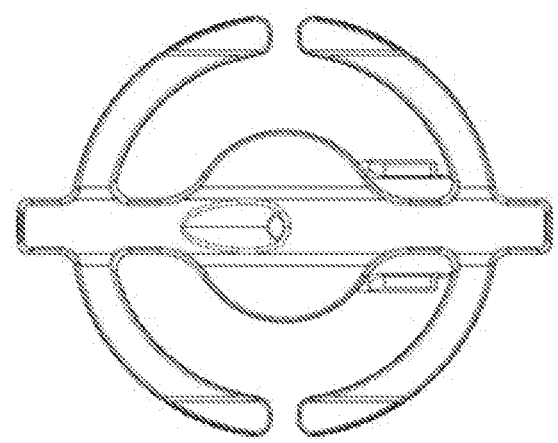
Figure 56C:
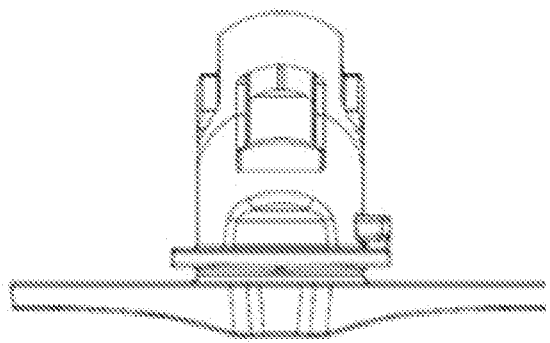
Figure 56D:
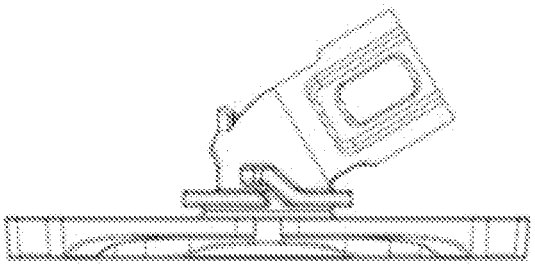
Figure 57A:
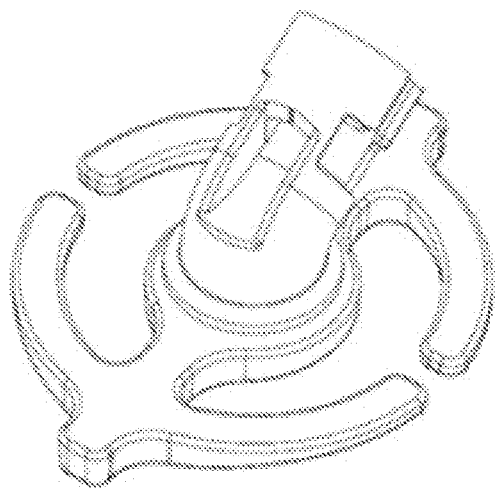
FIGS. 57A, 57B, 57C, and 57D are diagrams of perspective, top, front, and side views of an illustrative embodiment of a closure apparatus.
Figure 57B:
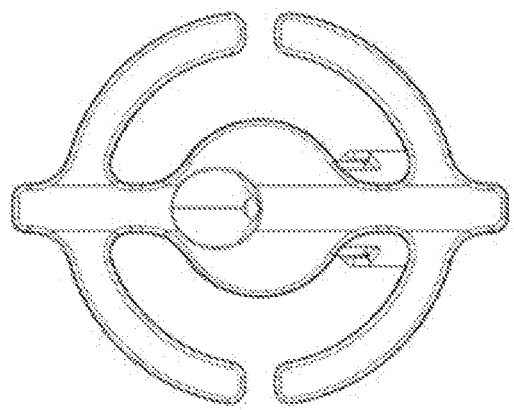
Figure 57C:
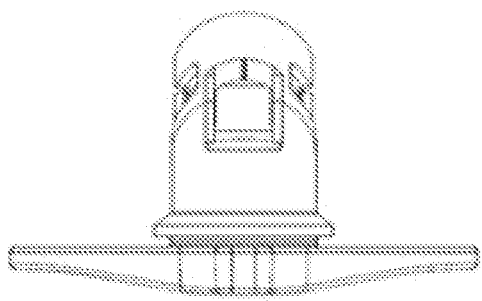
Figure 57D:
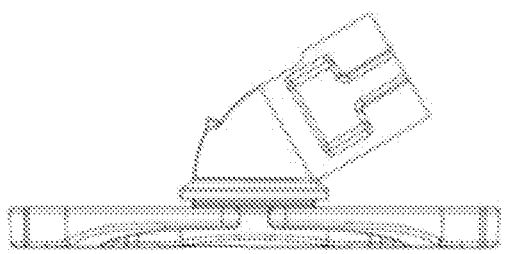
Figure 58A:
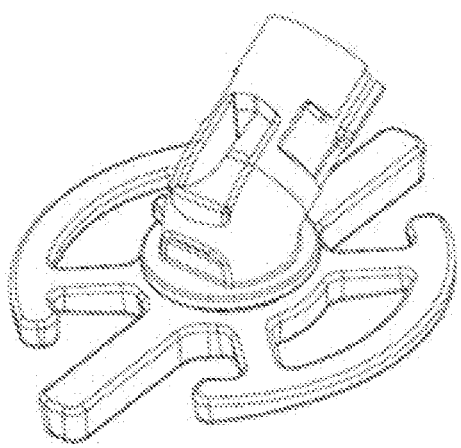
FIGS. 58A, 58B, 58C, and 58D are diagrams of perspective, top, front, and side views of an illustrative embodiment of a closure apparatus.
Figure 58B:
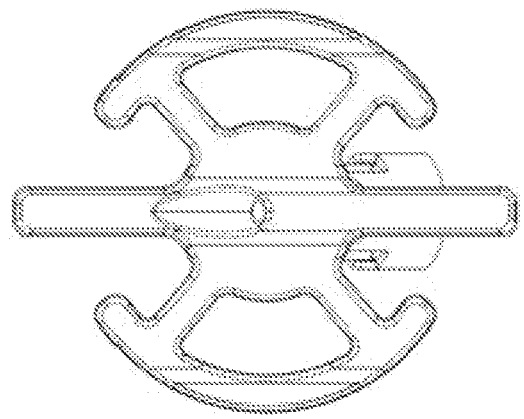
Figure 58C:
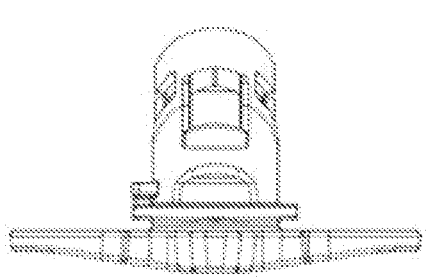
Figure 58D:
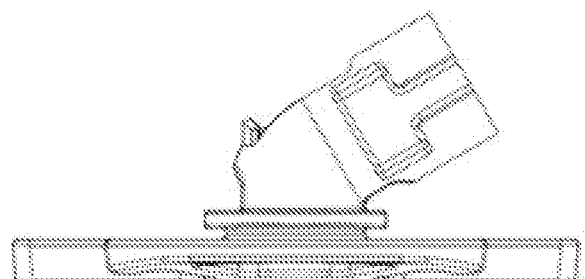
Figure 59A:
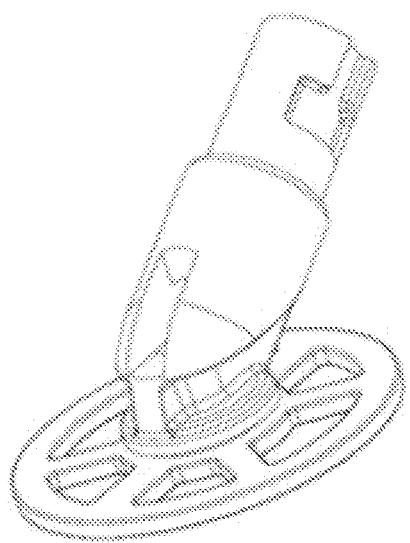
FIGS. 59A, 59B, 59C, and 59D are diagrams of perspective, top, front, and side views of an illustrative embodiment of a closure apparatus.
Figure 59B:
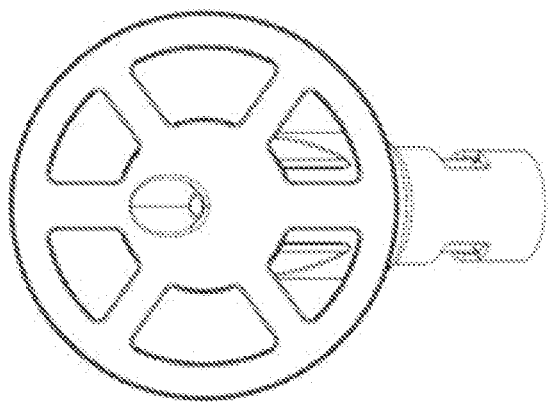
Figure 59C:
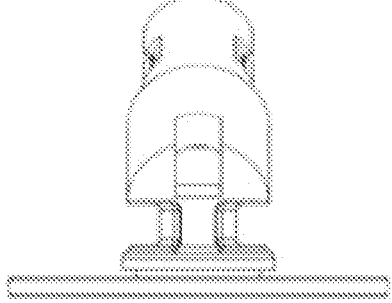
Figure 59D:
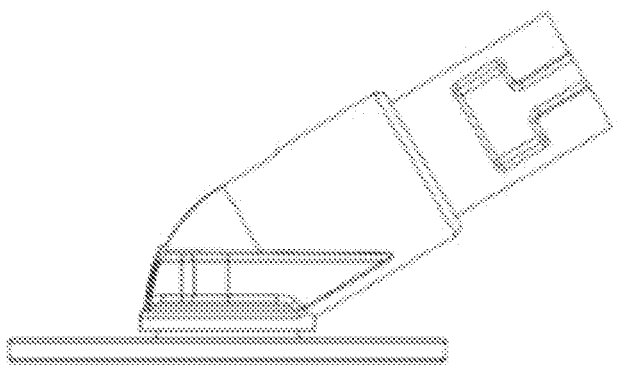
Figure 60A:
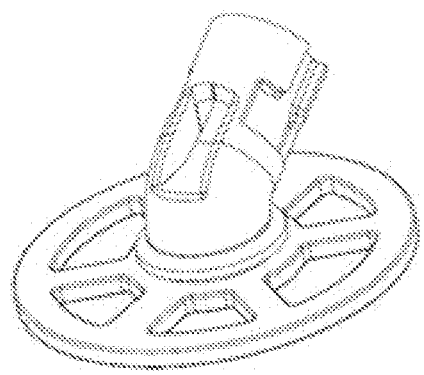
FIGS. 60A, 60B, 60C, and 60D are diagrams of perspective, top, front, and side views of an illustrative embodiment of a closure apparatus.
Figure 60B:
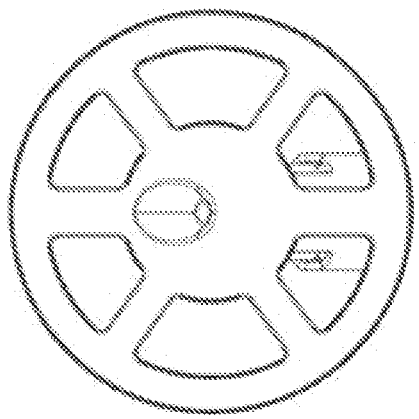
Figure 60C:
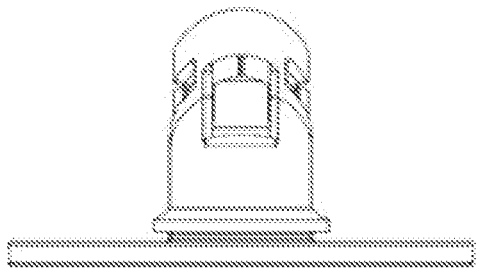
Figure 60D:
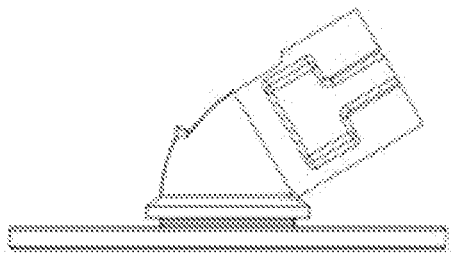
Figure 62A:
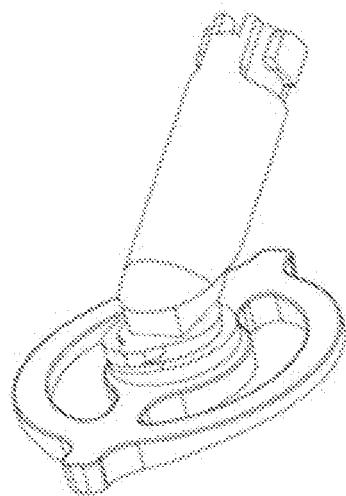
FIGS. 62A, 62B, 62C, and 62D are diagrams of perspective, top, front, and side views of an illustrative embodiment of a closure apparatus.
Figure 62B:
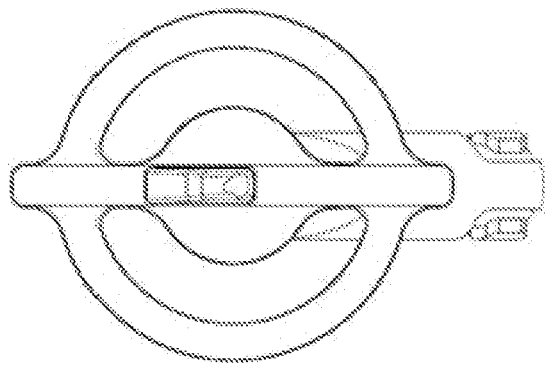
Figure 62C:
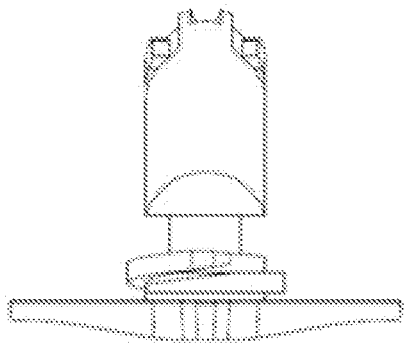
Figure 62D:
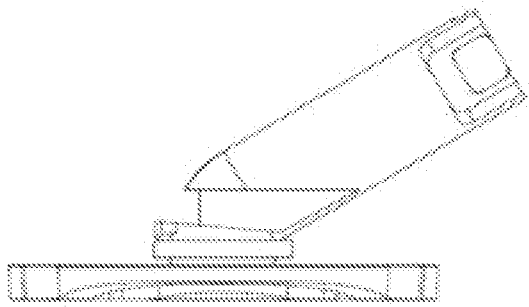
Figure 63A:
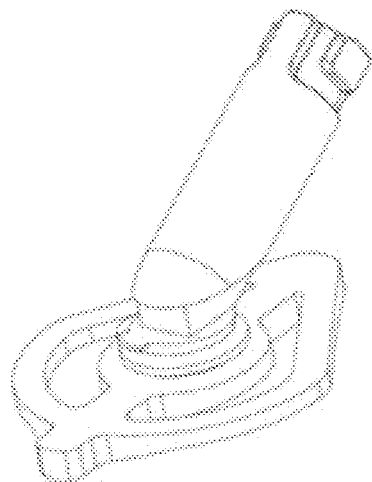
FIGS. 63A, 63B, 63C, and 63D are diagrams of perspective, top, front, and side views of an illustrative embodiment of a closure apparatus.
Figure 63B:
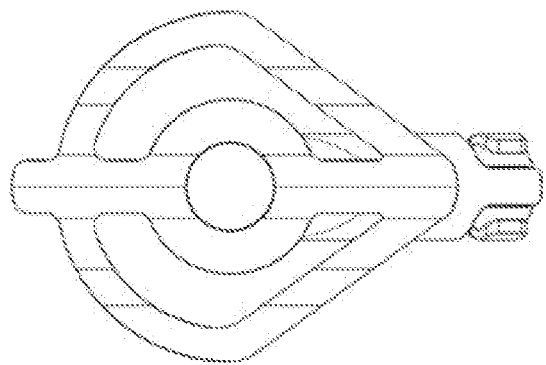
Figure 63C:
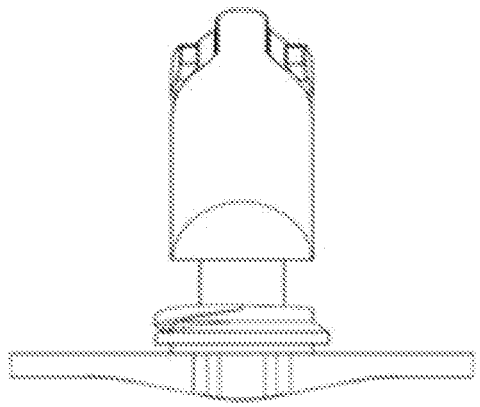
Figure 63D:
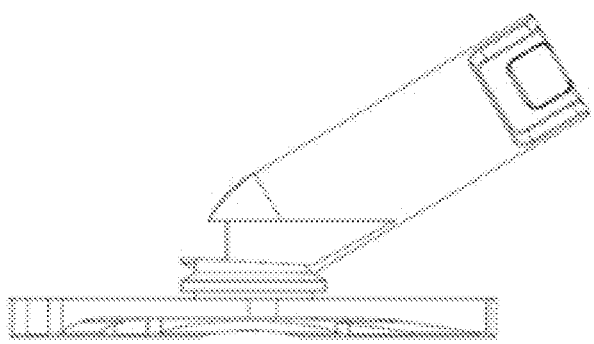
Figure 64A:
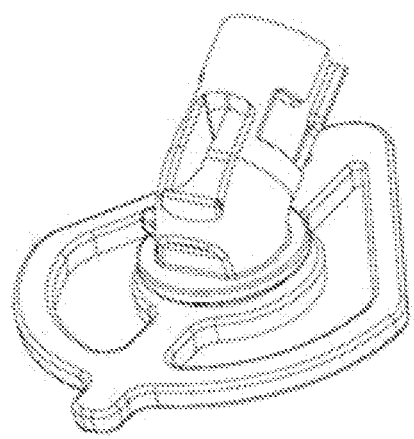
FIGS. 64A, 64B, 64C, and 64D are diagrams of perspective, top, front, and side views of an illustrative embodiment of a closure apparatus.
Figure 64B:
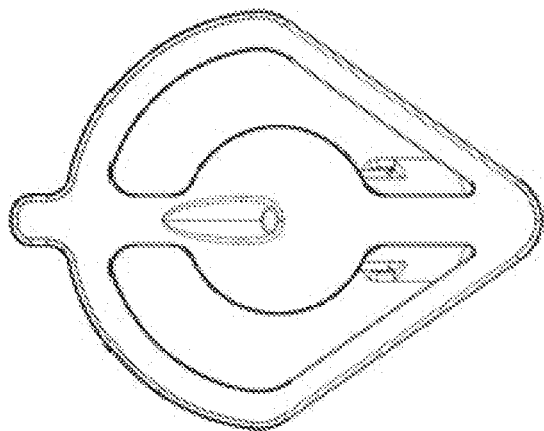
Figure 64C:
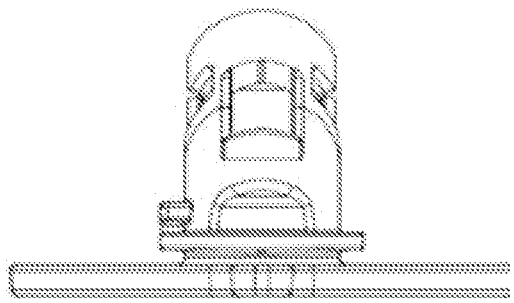
Figure 64D:
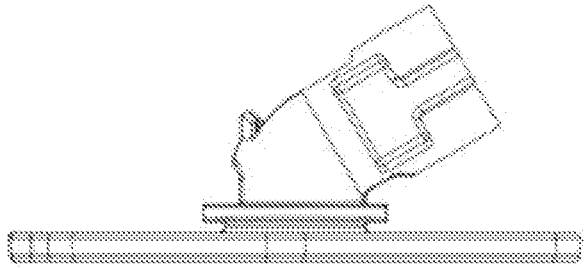
Figure 65A:
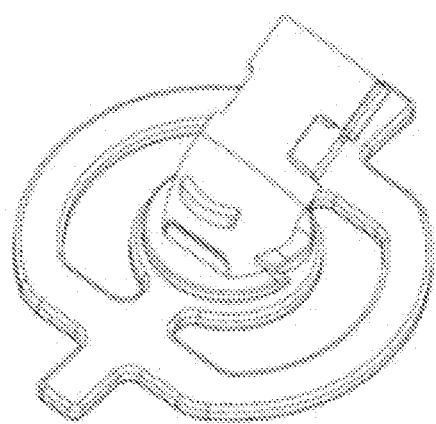
FIGS. 65A, 65B, 65C, and 65D are diagrams of perspective, top, front, and side views of an illustrative embodiment of a closure apparatus.
Figure 65B:
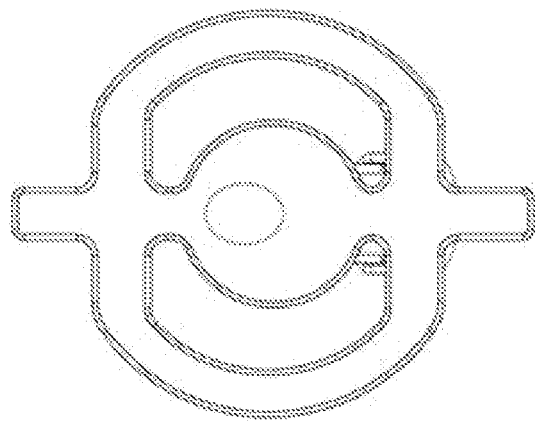
Figure 65C:
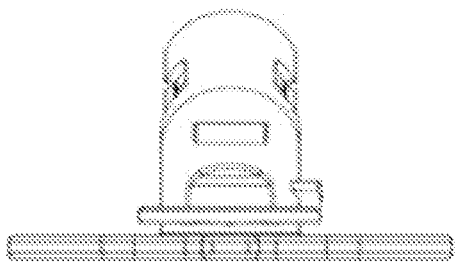
Figure 65D:
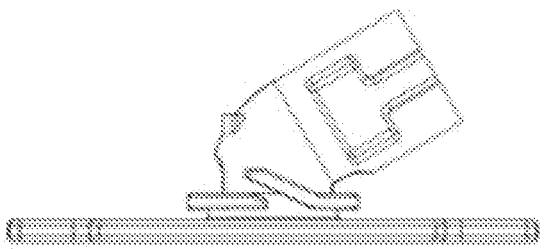
Figure 66A:
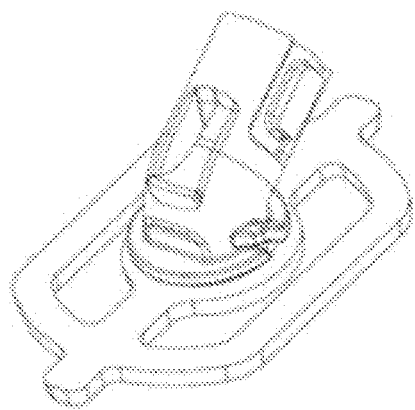
FIGS. 66A, 66B, 66C, and 66D are diagrams of perspective, top, front, and side views of an illustrative embodiment of a closure apparatus.
Figure 66B:
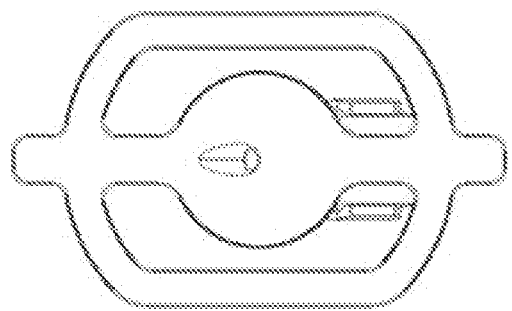
Figure 66C:
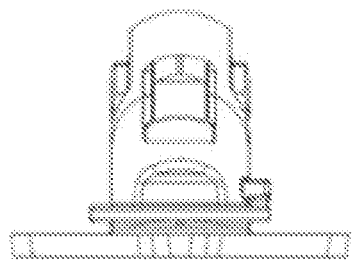
Figure 66D:
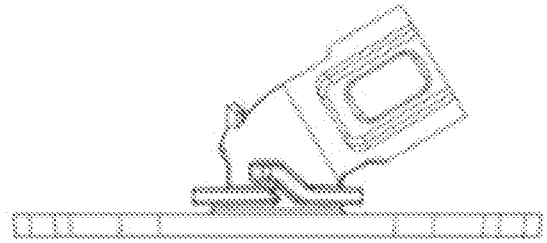
Figure 67A:
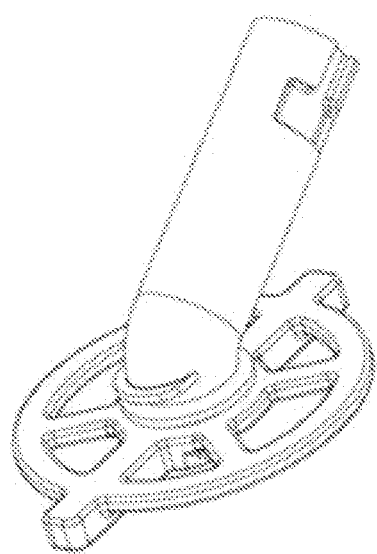
FIGS. 67A, 67B, 67C, and 67D are diagrams of perspective, top, front, and side views of an illustrative embodiment of a closure apparatus.
Figure 67B:
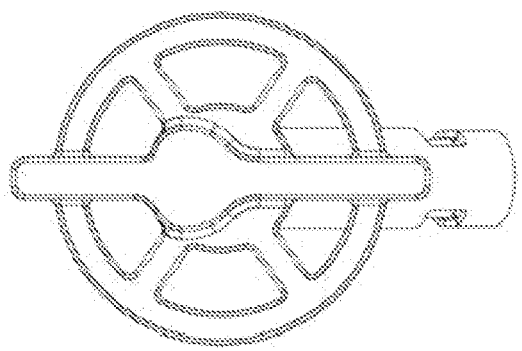
Figure 67C:
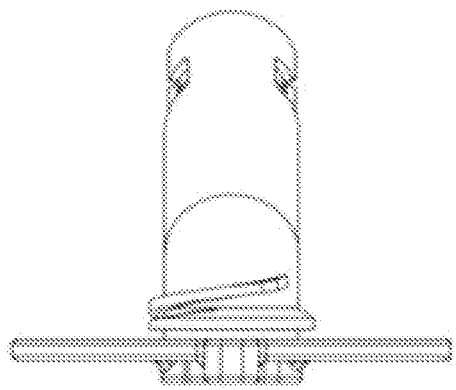
Figure 67D:
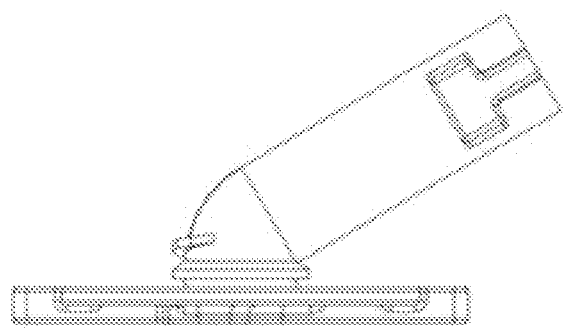
Figure 68A:
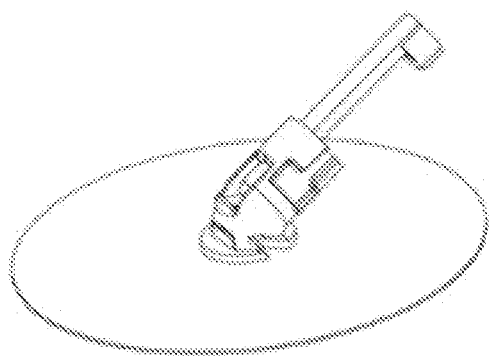
FIGS. 68A, 68B, 68C, and 68D are diagrams of perspective, top, front, and side views of an illustrative embodiment of a closure apparatus.
Figure 68B:
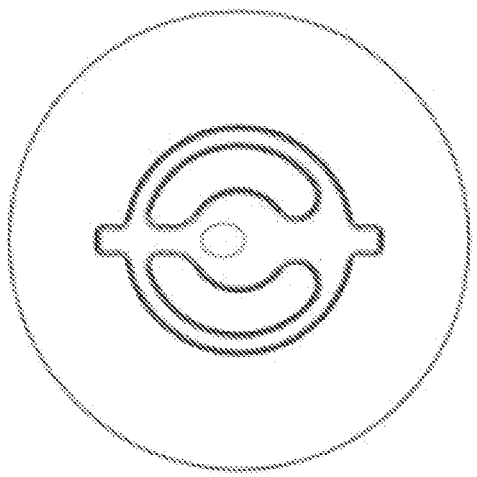
Figure 68C:
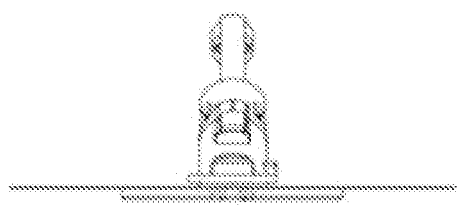
Figure 68D:
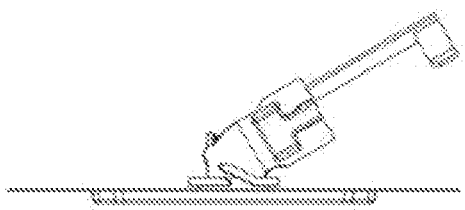
Figure 70A:
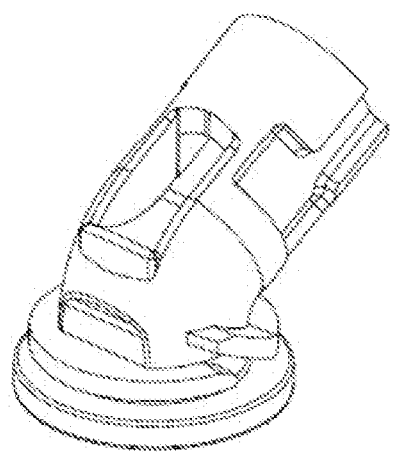
FIGS. 70A, 70B, 70C, and 70D are diagrams of perspective, top, front, and side views of an illustrative embodiment of a closure apparatus.
Figure 70B:
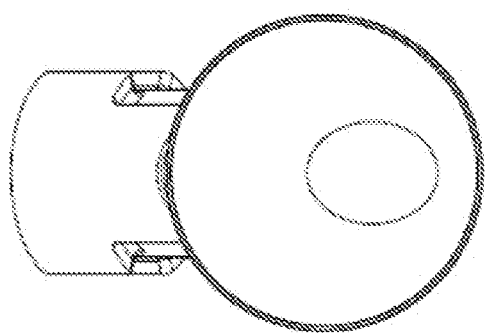
Figure 70C:
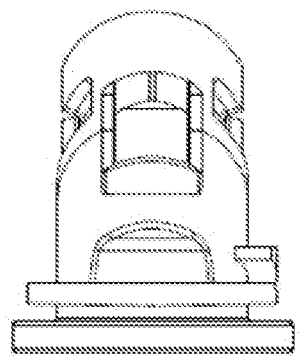
Figure 70D:
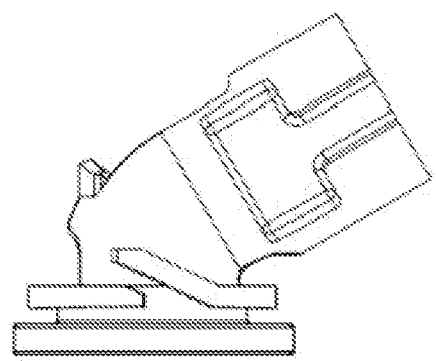
Figure 71A:
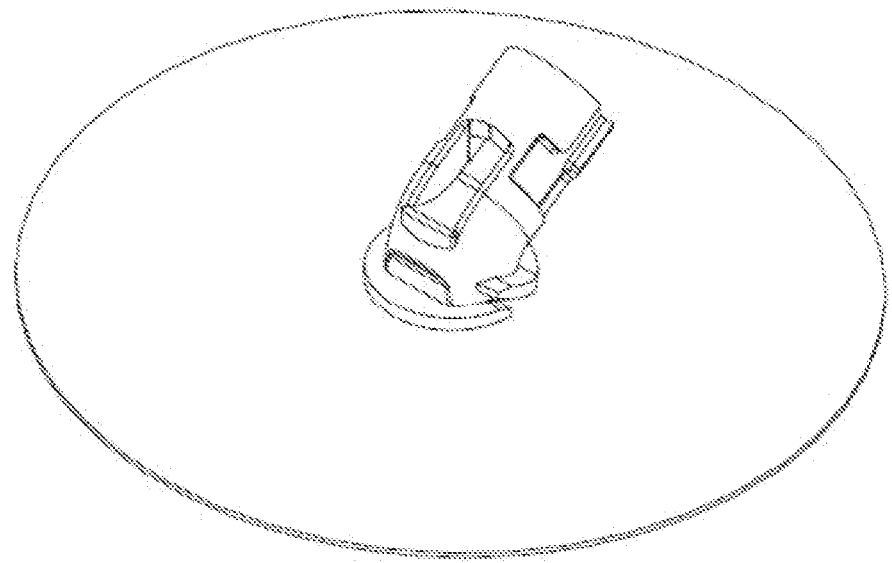
FIGS. 71A, 71B, and 71C are diagrams of perspective, front, and side views of an illustrative embodiment of a closure apparatus.
Figure 71B:
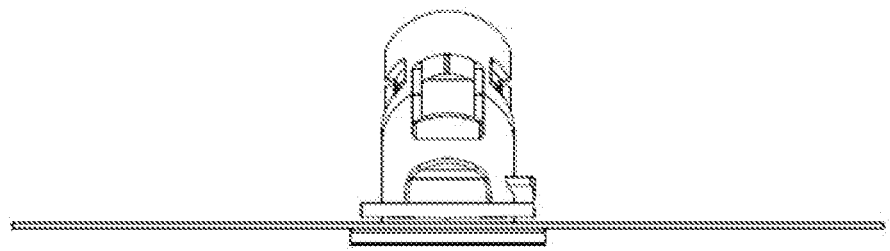
Figure 71C:
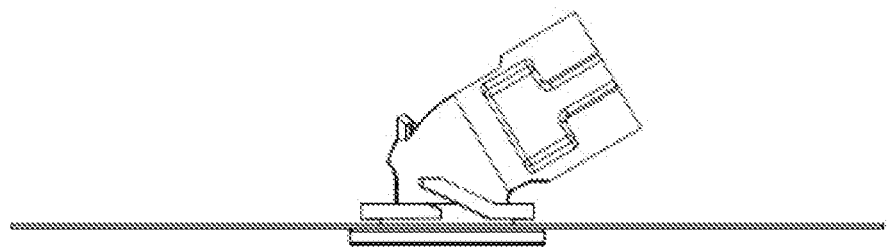
Figure 72A:
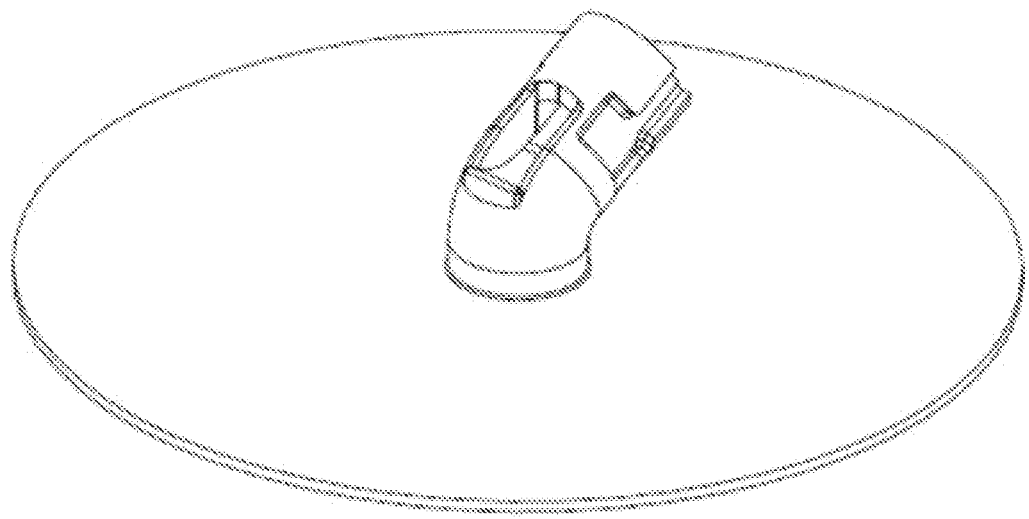
FIGS. 72A, 72B, and 72C are diagrams of perspective, front, and side views of an illustrative embodiment of a closure apparatus.
Figure 72B:
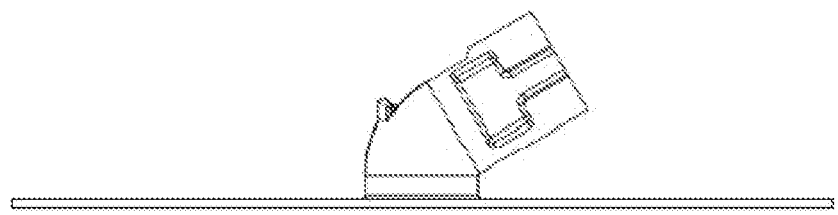
Figure 72C:
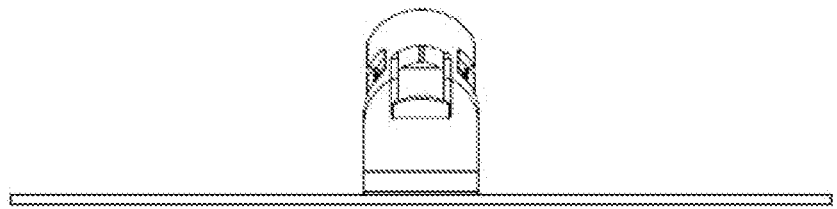

FIG. 21C shows the sealable member 106 and the support member 118 in their folded state. The folded implant is prepared for direct insertion into a body lumen, e.g., an artery. The loading funnel 2104 is then detached from the delivery cannula 2202. FIG. 22 is a diagram of the sealing member and support member in the delivery configuration in the delivery cannula 2202. Further examples of the loading funnel and delivery cannula is described in U.S. Patent Application Publication No. US 2014/0345109, filed Mar. 13, 2014, titled "Loading Devices and Methods for Percutaneous Perforation Closure Systems," the content of which is incorporated by reference herein in its entirety.

Figure 17A:
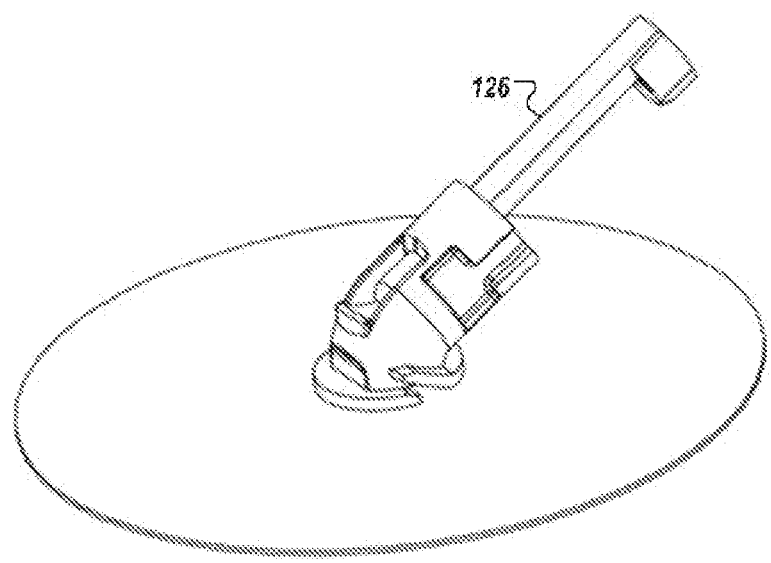
FIGS. 17A, 18A and 18B are diagrams showing a perspective view and a cross-sectional view of an assembled closure device.
Figure 17B:
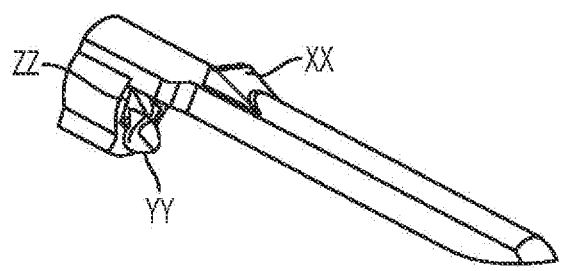
FIG. 17B is diagram showing a perspective view of a locking feature.
Figure 18A:
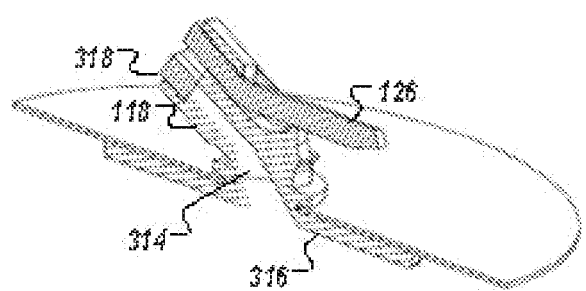
Figure 18B:
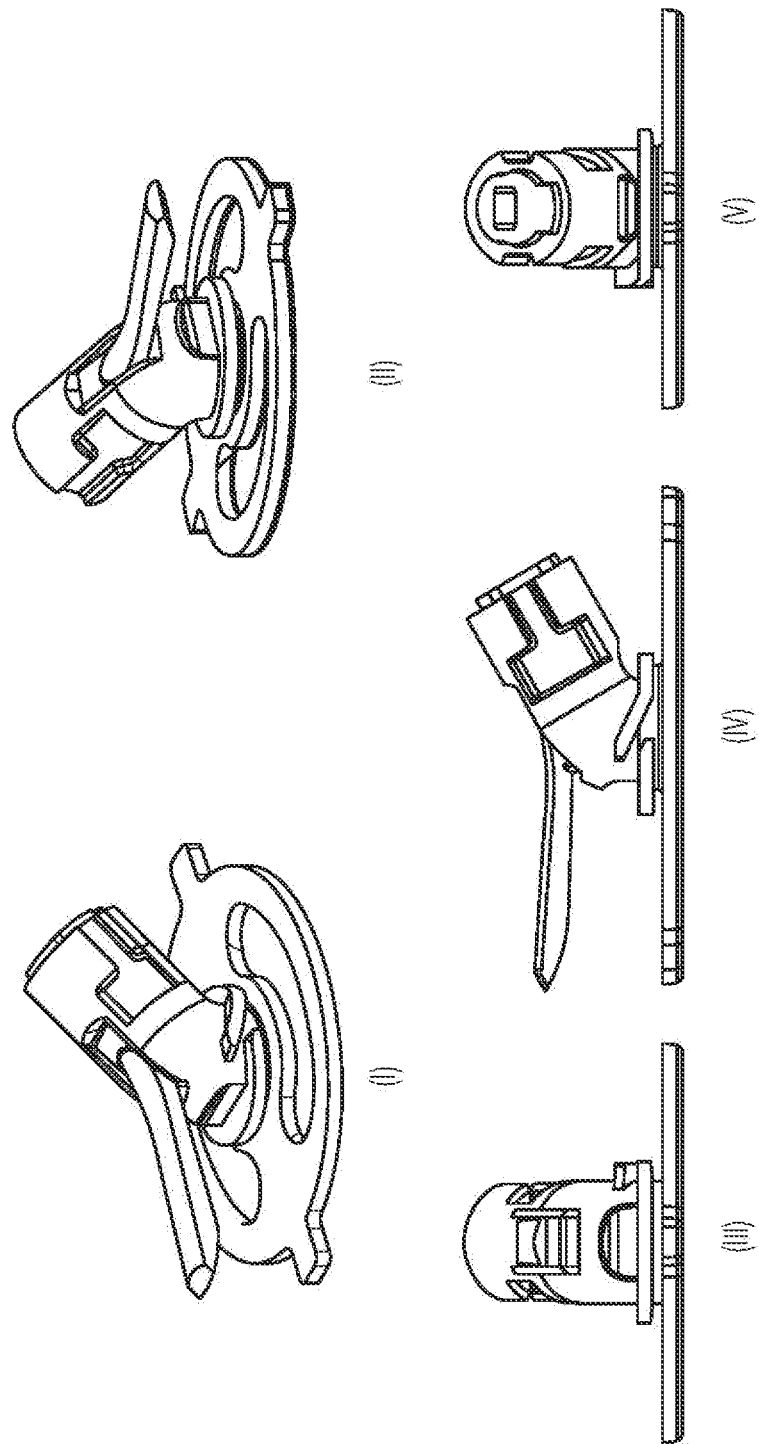

Referring back to FIG. 3B, the support member 118 has a channel 314 for guiding the guide wire 202 (see FIG. 2). In some embodiments, the channel 314 runs through the support member 118 between a bottom surface 316 of the base 120 and a top surface 318 of the column 122 (see FIG. 18A). Referring to FIGS. 17A, 17B, 18A and 18B, in certain embodiments, the channel 314 runs from the bottom of the center of the support member 118 to the top of the column 122 for guide wire access. FIG. 17A shows the closure device 100 and the guard member 126, prior to the deployment of the guard member 126. FIG. 17B shows an embodiment of guard member containing a locking feature (xx) to lock the guard member into position. A wedge feature (yy) which closes guide wire access channel 314 reduces blood loss through this avenue. The guard member contains a guide wire lumen (22) which can accommodate up to a 0.018" guide wire. FIG. 18A is a cross-sectional perspective view of diagram of the guard member 126 in the deployed state. FIG. 18B is view of a diagram of the guard member (FIG. 17B) in the deployed state in support member (FIG. 4C)

Threaded Portion on the Support Member

FIGS. 19A, 19B, and 19C are diagrams of a perspective view, a side view, and a front view of a closure device with a threaded portion 1900 to allow assembly of the sealable member 106 to the support member 118 without distortion or deformation of the sealable member 106. The threaded portion 1900 provides a region for the sealable member 106 to load onto the support member 118. Without having to distort and/or deform the sealable member 106 during assembly of the sealable member 106 onto the support member 118, the risk of damage to the sealable member 106 during manufacturing is reduced. The threaded portion may include a protrusion 1902 that encircles the body 1904 of the column 122. The protrusion 1902 includes a gap 1904. The protrusion 1902 has a greater diameter, in some embodiments, than that of the column 122.

The threaded portion may be employed with a support member having a rigid foot core. Further examples of rigid foot cores are described in U.S. Patent Application Publication No. US 2013/0274795, titled "Devices and Methods for Delivering Implants for Percutaneous Perforation Closure," the contents of which is incorporated herein in its entirety. Examples of rigid foot core with threaded portions are provided in FIGS. 23A-72C.

In some embodiments, the threaded portion is employed in conjunction with a "button" foot core design. The button foot core, in some embodiments, is round. The profile of the "button" foot core is such that the base diameter is only slightly wider than the hole in the center of the wing. The wing can, thus, be threaded onto the column of the button foot core. An example of the "button" foot core design is provided in FIGS. 70A-71C.

In some embodiments, the "button" foot core design is employed for smaller sized apertures (e.g., between 6 and 18 (F) French), e.g., for usage in smaller-sized blood vessels/lumens.

Figure 20A:
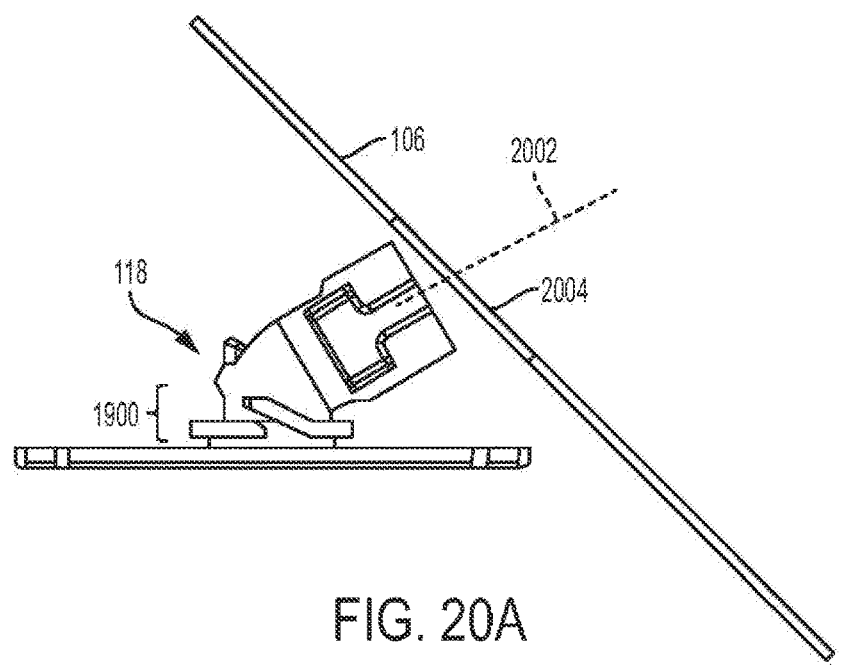
FIGS. 20A, 20B, 20C, and 20D are diagrams showing a sequence for assembling the sealing member to a support member configured with a threaded portion.

FIGS. 20A, 20B, 20C, and 20D are diagrams showing a sequence for assembling the sealing member to a support member configured with a threaded portion. In certain embodiments, the axis of the sealable member 106 is oriented along the longitudinal axis 2002 of the column 122. FIG. 20A is a diagram of a sealable member 106 oriented with respect to the sealable member 118 according to an embodiment.

The sealable member 106 comprises a hole 2004 that has a profile so as to translate along the axis 2002 without contacting the column 122 of the sealable member 118. Alternatively, the sealable member 106 is oriented along a plane parallel to the base 120 during assembly of the sealable member 106 and the support member 118 (not shown).

Figure 20B:
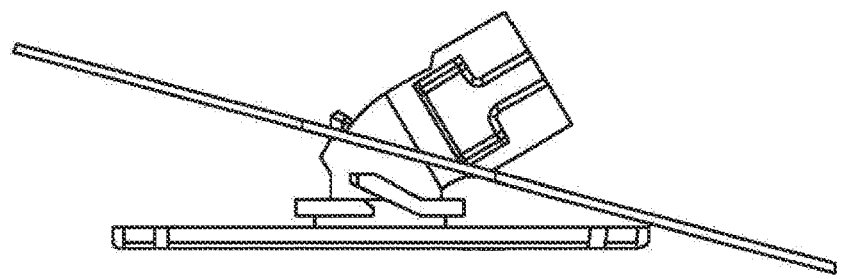

FIG. 20B is a diagram of the sealable member 106 disposed around the column 122.

Figure 20C:
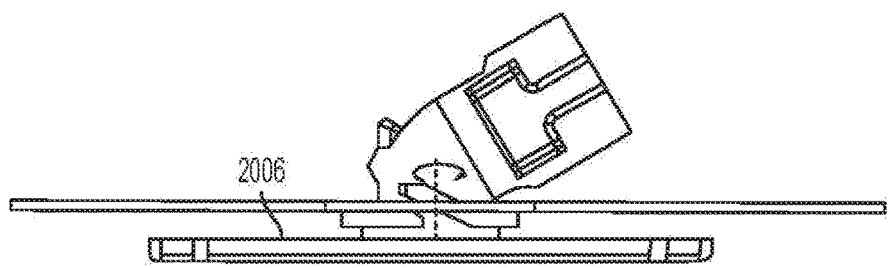

FIG. 20C is a diagram of the sealable member 106 being rotatably translated onto a contact surface 2006 of the base 120 of the support member 118.

Figure 20D:
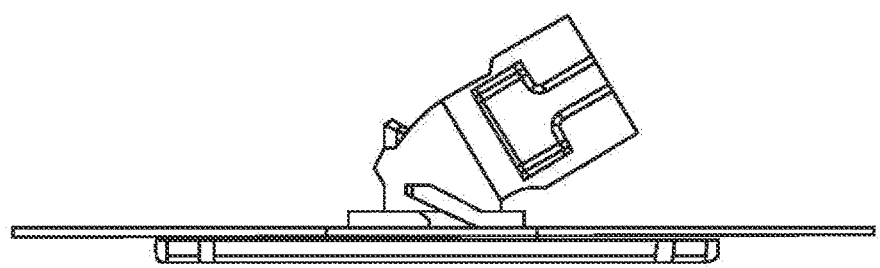

FIG. 20D is a diagram of the sealable member 106 resting on the contact surface 2306 of the base 120.

In certain embodiments, during the assembly, the support member 118 is stationary with respect to the sealable member 106, while the sealable member 106 is moved along the column 122 to the treaded section 1900. In other embodiments, the sealable member 106 is stationary with respect of the support member 118, while the support member 118 is moved through the hole 2004 of the sealable member 106. In yet other embodiments, both the sealable member 106 and the support member 118 move with respect to each other.

Slotted Shoe

In certain embodiments, the surgical closure systems, devices, and methods described herein comprise a device that can exert pressure on the external surface of a tissue. In certain embodiments, the surgical closure systems, devices, and methods described herein comprise an external, e.g., extra-arterial, securing component (e.g., a cage or "shoe"), e.g., to secure a vascular closure device (VCD) implant to a blood vessel and/or to help maintain the seal, e.g., of the arteriotomy or veinotomy by compressing a wall of the artery or vein between it and the wing of the VCD when the device is deployed. In certain embodiments, the cage or shoe, in combination with pressure present in a vessel, e.g., hydraulic pressure present in an artery or vein (e.g., hemodynamic pressure of blood), or other body lumen, improves tamponade formed by the device over the aperture, e.g., an arteriotomy or veinotomy. In some embodiments, the cage or shoe comprises one or more structural features, e.g., indentations, ridges, shoulders, planes, curved planes, cavities, notches, holes, slots, surfaces, and/or grooves. In certain embodiments, the cage or shoe comprises one or more engagement elements (e.g., indentations, ridges, shoulders, planes, curved planes, cavities, notches, holes, slots, surfaces, and/or grooves), e.g., elements that can engage with another device or element, e.g. a support member. In some embodiments, the cage or shoe can be used in combination with column 122 of the support member 118 (see FIG. 3A), e.g., to secure a VCD implant to a blood vessel, e.g., an artery or a vein. In certain embodiments, the column or the support member comprise a locking feature that can engage with a feature of the shoe (e.g., an engagement element, e.g., an indentation, notch, hole, surface, slot, and/or groove). In certain embodiments, when the shoe is deployed and fully engaged, a locking feature engages with an engagement element to lock the cage or shoe in place. In certain embodiments, the column or the support member comprise a centering feature that can engage with a feature of the shoe (e.g., an indentation, notch, hole, surface, slot, and/or groove) when the shoe is deployed and fully engaged, e.g., to prevent the cage or shoe from rotating and/or prevent the cage or shoe from becoming unlocked and/or disengaged from the implant.

Figure 73A:
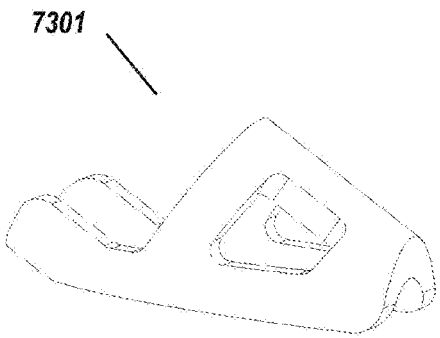
FIGS. 73A and 73B are diagrams showing perspective views of an exemplary extra-arterial shoe.
Figure 73B:
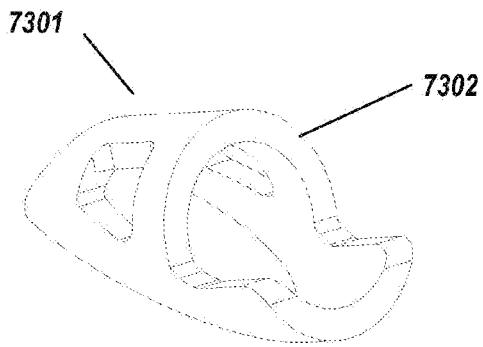

In certain specific embodiments, the cage or shoe is a shoe 7301 as shown in FIGS. 73A and 73B. In certain embodiments, the cage or shoe has a caged structure and/or comprises one or more concave structural elements. In certain embodiments, the radius (e.g., inner radius) of a concave structural element corresponds to a radius of a surface of the column or the support member, e.g., of a cylindrical portion of the column or the support member. In certain embodiments, the shoe comprises one or more engagement elements that can engage with a support member (e.g., an indentation, notch, hole, surface, slot, and/or groove). In certain embodiments, the shoe comprises a shoulder, e.g., shoulder 7302.

Figure 74A:
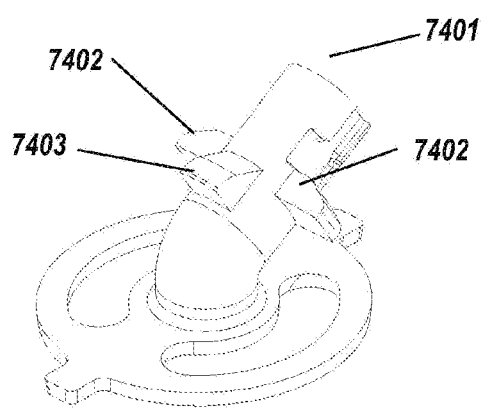
FIGS. 74A, 74B, and 74C are diagrams showing a perspective view, a front view, and a side view of a support member of the closure device, according to an illustrative embodiment.
Figure 74B:
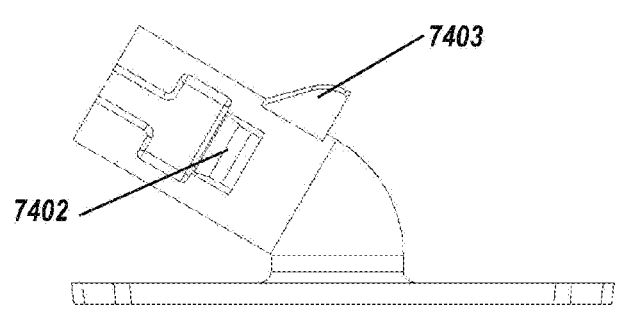
Figure 74C:
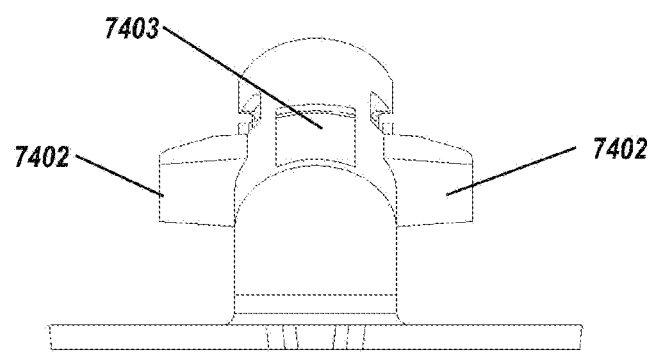

In certain embodiments, a support member, e.g., support member 118, comprises tabs, e.g., as shown in FIG. 74. In certain embodiments, a tabbed support member, e.g., tabbed support member 7401, comprises one or more locking tabs 7402, and/or one or more centering tabs 7403. In certain embodiments, a tabbed support member comprises 1, 2, 3, 4, 5, or more locking tabs. In certain embodiments, a tabbed support member comprises 1, 2, 3, 4, 5, or more centering tabs. The locking tabs and/or the centering tabs can be positioned anywhere on the tabbed support member. In certain embodiments, the tabbed support member comprises one centering tab and two locking tabs. In certain embodiments, the locking tabs are positioned opposite to each other along the circumference of a cylindrical portion of the tabbed support member. In certain embodiments, the one or more locking tabs and the one or more centering tabs are aligned. In certain embodiments, a centering tab is a locking tab. In certain embodiments, the locking tabs "lock" with a feature of the cage or shoe (e.g., an engagement element, e.g., an indentation, notch, hole, surface, slot, and/or groove) when the cage or shoe is deployed and fully engaged, e.g., the locking tabs snap fit with the shoe. In certain embodiments, the locking tabs "lock" in behind the shoulder of the shoe when the shoe is deployed and fully engaged, e.g., the locking tabs snap-fit with the cage or shoe. In some embodiments, the centering tab or tabs can prevent the shoe biasing to one side of the implant, e.g., by preventing the shoe from rotating around the longitudinal axis of column 122. In certain embodiments, the one or more centering tabs engage an interior surface or interior portion or interior feature of the cage or shoe. In certain embodiments, the one or more centering tabs engage the shoulder of the shoe. In certain embodiments, the one or more centering tabs can prevent the shoe biasing to one side of the implant, e.g., by reversibly engaging one or more features (e.g., notch, hole, surface, slot, and/or groove) of the cage or shoe. In certain embodiments, the one or more centering tabs engage an interior surface, or interior portion, or one or more interior features (e.g., notch, hole, surface, slot, and/or groove) of the cage or shoe. Without wishing to be bound by theory, if the cage or shoe were to move from its intended final position, e.g., toward one side of the implant, one or more of the locking tabs could potentially disengage from the cage or shoe releasing the implant.

Figure 75:
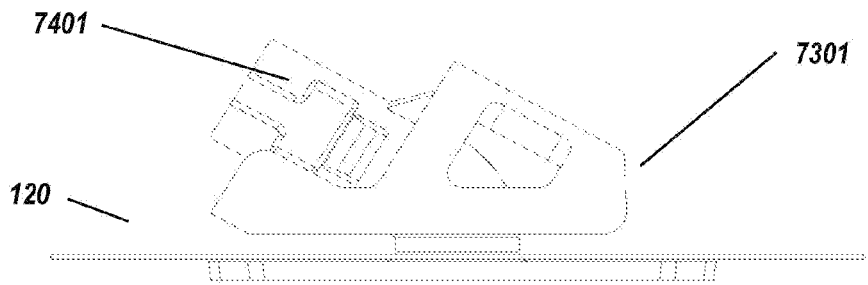
FIG. 75 is a diagram of an exemplary extra-arterial shoe engaged with a support member of the closure device, according to an illustrative embodiment.

FIG. 75 depicts shoe 7301 deployed on an exemplary tabbed support member 7401 according to an exemplary embodiment. In certain embodiments, the shoe can secure a vascular closure device (VCD) implant to a blood vessel and/or help maintain the seal, e.g., of an arteriotomy or a veinotomy, e.g., by compressing the wall of an artery or vein between it and a base 120.

Figure 76A:
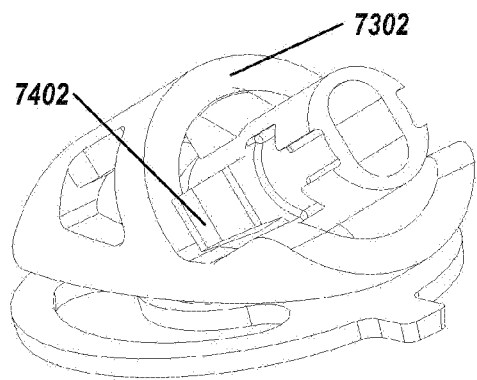
FIGS. 76A, 76B, and 76C are diagrams showing a perspective view and a rear view of a support member of the closure device, according to an illustrative embodiment.
Figure 76B:
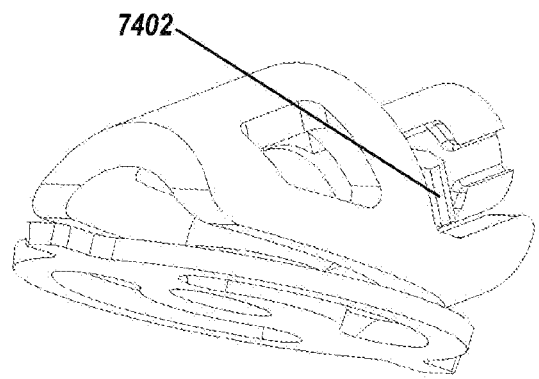
Figure 76C:
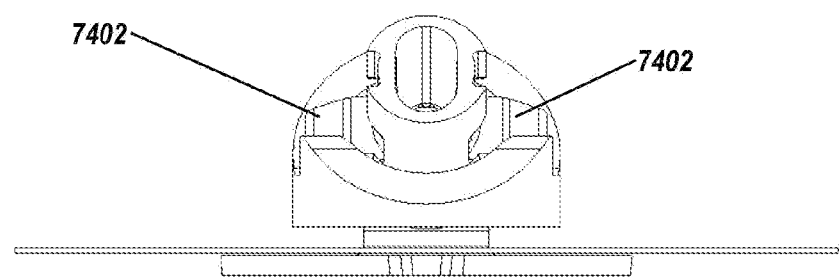

FIG. 76 depicts shoe 7301 engaged with an exemplary tabbed support member 7401 according to an exemplary embodiment. In certain embodiments, one or more locking tabs 7402 engage the shoulder of the shoe (e.g., shoe 7301), as shown, e.g., in FIG. 76A and FIG. 76B. In certain embodiments, two locking tabs 7402 engage the shoulder of the shoe as shown, e.g., in FIG. 76C. In certain embodiments, a centering tab engages an interior surface or interior portion or one or more interior features (e.g., notch, hole, surface, and/or groove) of the shoe.

Figure 77:
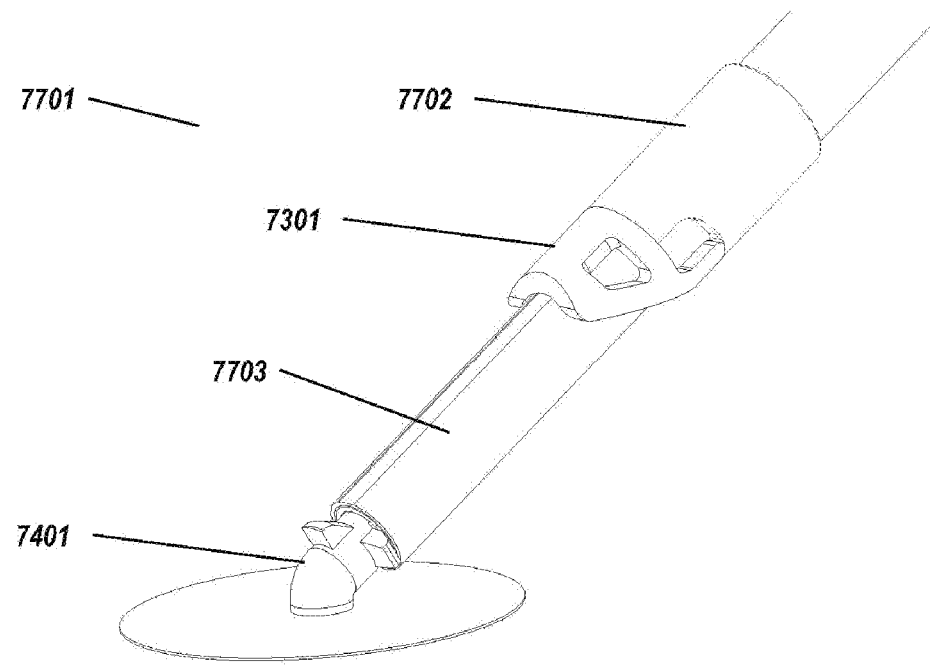
FIG. 77 is a diagram of an exemplary shoe connected to an exemplary delivery system in an initial position, according to an illustrative embodiment.

The extra-arterial securing component (e.g., a cage or "shoe") can be deployed using a variety of methods. FIG. 77 depicts shoe 7301 connected to an exemplary delivery system in an initial position. In certain embodiments, the shoe is mounted on an external shaft, e.g., external shaft 7703, of the delivery system. In certain embodiments, the shoe is slideably moveable along the longitudinal axis of the external shaft and/or along the axis 502 corresponding to a longitudinal axis of a delivery shaft, e.g., delivery shaft 504. In certain embodiments, the shoe is rotatable around the longitudinal axis of the external shaft 7703 and/or along the axis 502. In certain embodiments, the shoe is not rotatable around the longitudinal axis of the external shaft 7703 and/or around the axis 502.

In certain embodiments, the shoe (e.g., shoe 7301) can be moved by a shoe delivery element, e.g., a shoe pusher (e.g., shoe pusher 7702) and/or a delivery shaft, along the longitudinal axis of the external shaft 7703 and/or along the axis 502. In certain embodiments, the shoe pusher is mounted on an external shaft, e.g., external shaft 7703, of the delivery system. In certain embodiments, the shoe pusher is slideably moveable along the longitudinal axis of the external shaft and/or along the axis 502 corresponding to a longitudinal axis of a delivery shaft, e.g., delivery shaft 504. In certain embodiments, deploying the shoe comprises the steps of reversibly engaging the shoe pusher with the shoe and advancing the shoe pusher distally (e.g., toward the implant), e.g., advancing the shoe pusher a set distance. In certain embodiments, the shoe pusher is reversibly engaged with the shoe such that the shoe can only be moved distally (e.g., toward the implant and away from the operator). In certain embodiments, the shoe pusher is engaged with the shoe such that the shoe can be moved distally and/or proximally (e.g., away from the implant and toward from the operator).

Figure 78:
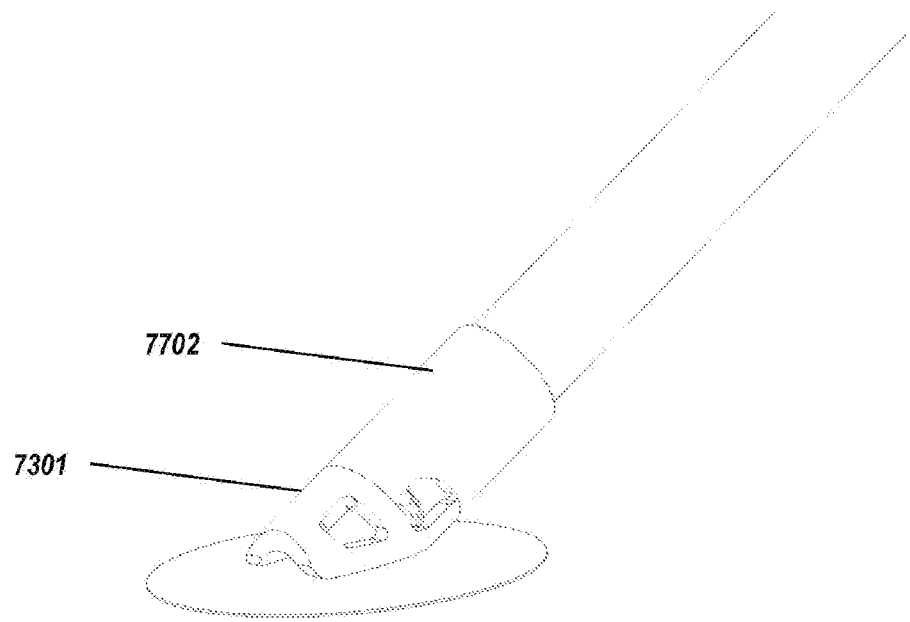
FIG. 78 is a diagram of an exemplary shoe connected to an exemplary delivery system in a second position, according to an illustrative embodiment.

In certain embodiments, deploying the shoe comprises the steps of reversibly engaging the shoe pusher with the shoe and advancing the shoe pusher distally (e.g., toward the implant), e.g., advancing the shoe pusher a set distance, and engaging the shoe with the implant (e.g., with the tabbed support member 7401) by locking the shoe onto the locking tabs, e.g., locking tabs 7402, e.g., as shown in FIG. 78.

Figure 79:
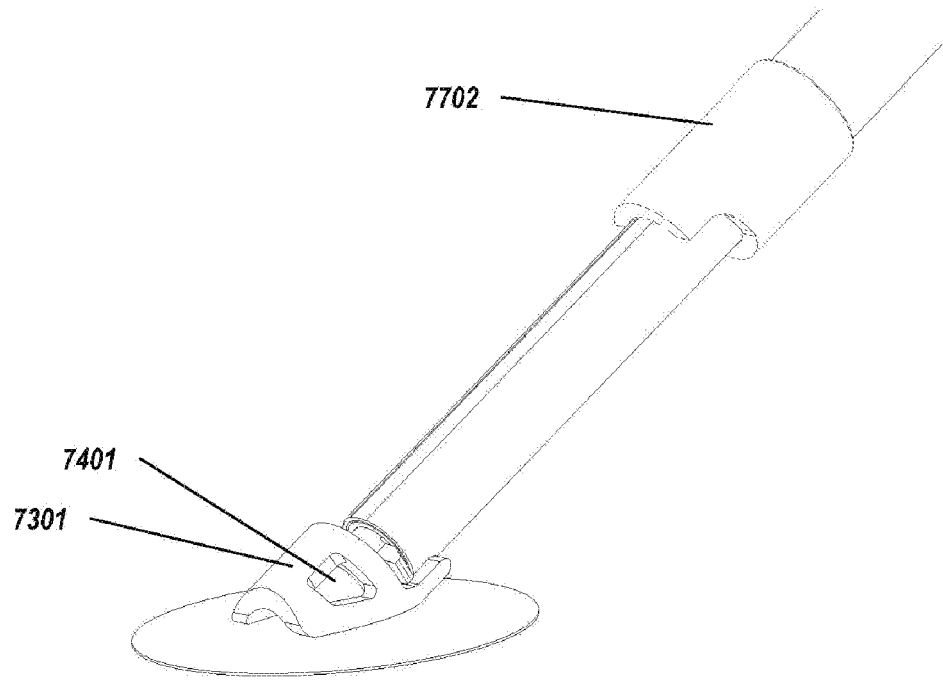
FIG. 79 is a diagram of an exemplary shoe connected to an exemplary delivery system in a second position, with the shoe pusher in a retracted position according to an illustrative embodiment.

FIG. 79 depicts the shoe 7301 deployed and engaged with the implant via tabbed support member 7401 after deployment and after retraction of the shoe pusher 7702 according to an exemplary embodiment.

Figure 80:
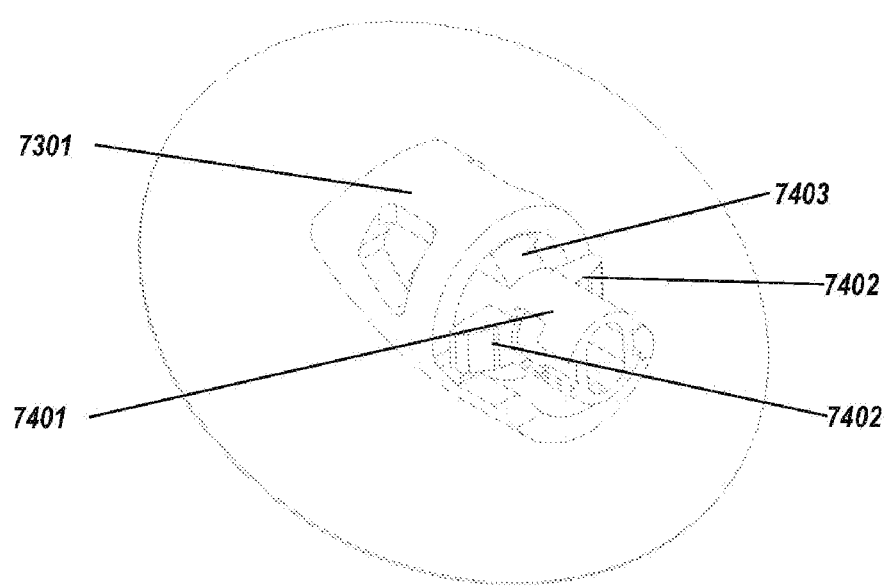
FIG. 80 is a diagram of an exemplary shoe deployed and engaged with a tabbed support member, according to an illustrative embodiment.

FIG. 80 depicts the shoe 7301 deployed and engaged with tabbed support member 7401 via locking tabs 7402 after deployment of the implant according to an exemplary embodiment. In certain embodiments, the shoe is only deployed when the implant has been withdrawn to the arteriotomy or veinotomy, and tamponade has been achieved.

In some embodiments, the cage or shoe comprises one or more shoe connector elements (e.g., shoe connector profiles) and/or delivery shaft profiles. In some embodiments, one or more shoe connector profiles and/or delivery shaft profiles can engage a delivery element, e.g., a shoe pusher and/or a delivery shaft. In some embodiments, one or more shoe connector profiles and/or delivery shaft profiles can engage the implant, e.g., are equivalent to, are part of, comprise, or are identical to the engagement elements engaging the implant, as described above.

In certain specific embodiments, the cage or shoe is a shoe 8101, e.g., as shown in FIGS. 81A and 81B. In certain embodiments, the shoe comprises one or more shoulders, e.g., shoulder 8102. In certain embodiments, the shoe comprises a connector element, e.g., shoe connector profile 8103, which can engage a shoe delivery element.

Without wishing to be bound by theory, the shoe connector and the shoe are designed such that the shoe connector can engage the shoe, e.g., at a shoe connector profile, in order to control the alignment of the shoe relative to the support member, e.g., by preventing the shoe from rotating around the longitudinal axis of column 122. In certain embodiments, the shoe connector profile can have the shape of a circle, square, rectangular, triangle, rhombus and/or any combination or composition thereof. In certain embodiments, the shoe connector profile can have the shape of a key hole.

FIG. 82 depicts exemplary shoe 8101 as part of an exemplary delivery system in an initial position. In certain embodiments, the shoe (e.g., shoe 8101) can engage a shoe delivery element, e.g., shoe connector 8202, via a matching shoe connector profile, e.g., shoe connector profile 8103.

Figure 83:
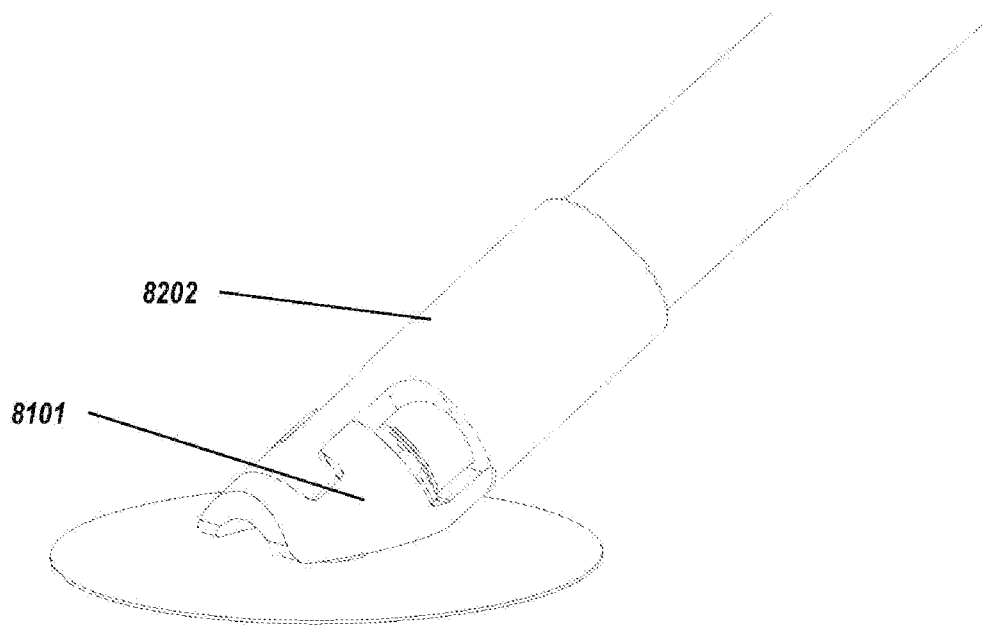
FIG. 83 is a diagram of an exemplary shoe connected to an exemplary delivery system in a second position, according to an illustrative embodiment.

In certain embodiments, the shoe (e.g., shoe 8101) is deployed by advancing the shoe connector (e.g., shoe connector 8202) distally (e.g., toward the implant), e.g., to a set distance, and engaging the shoe with the implant (e.g., with the tabbed support member 7401) by locking the shoe onto the locking tabs, e.g., locking tabs 7402, e.g., as shown in FIG. 83.

Figure 84:
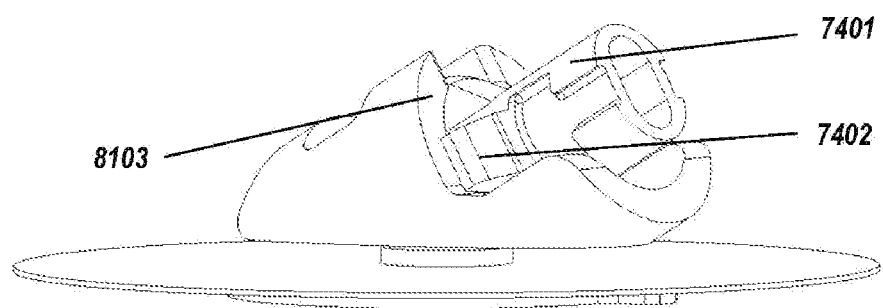
FIG. 84 is a diagram of an exemplary shoe deployed and engaged with a tabbed support member, according to an illustrative embodiment.
Figure 85:
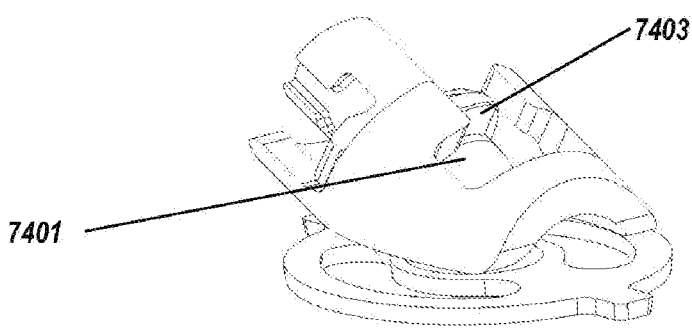
FIG. 85 is a diagram of an exemplary shoe deployed and engaged with a tabbed support member, according to an illustrative embodiment.
Figures 86A, 86B:
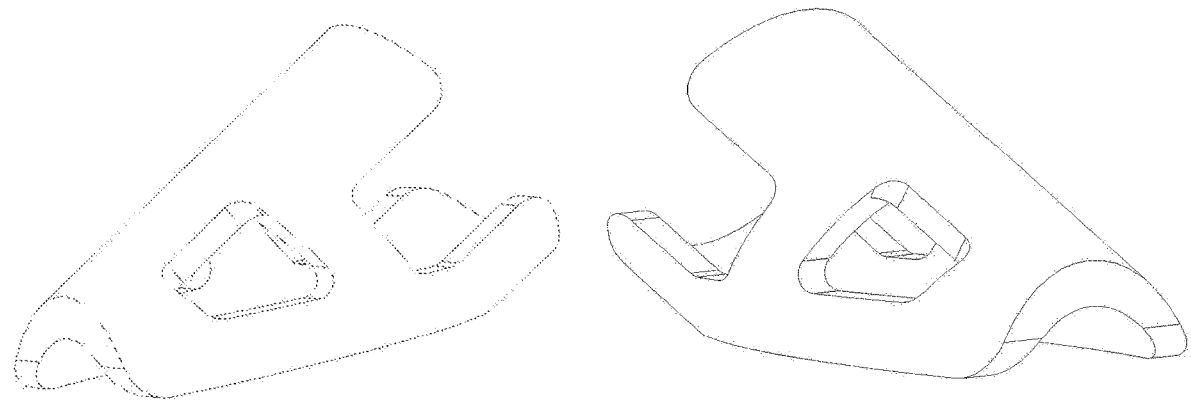
FIGS. 86A and 86B are diagrams showing perspective views of an exemplary extra-arterial shoe.
Figure 87A:
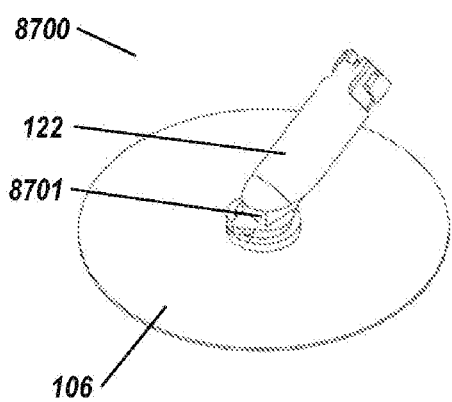
FIGS. 87A, 87B, 87C, and 87D are diagrams showing a perspective view, a bottom view, a front view, and a side view of a support member of the closure device, according to an illustrative embodiment.
Figure 87B:
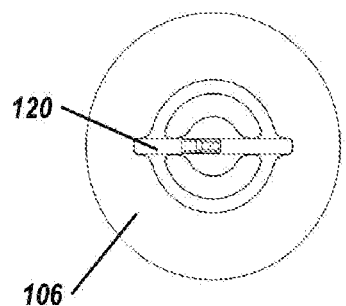
Figure 87C:
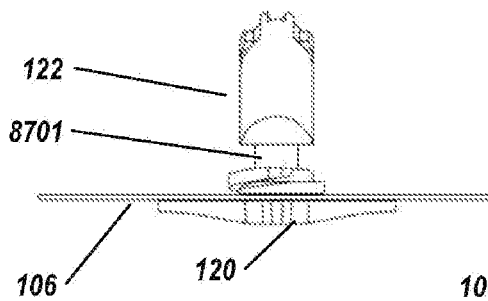
Figure 87D:
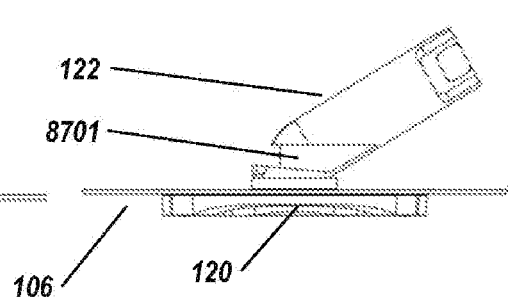
Figure 89A:
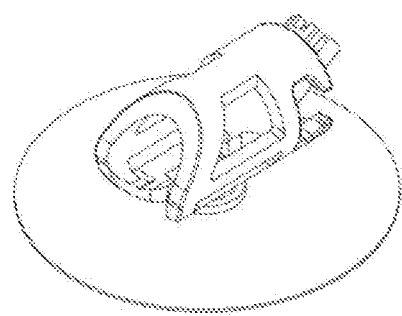
FIGS. 89A, 89B, 89C, and 89D are diagrams showing a perspective view, a bottom view, a rear view, and a side view of an exemplary extra-arterial shoe deployed and engaged with a support member, according to an illustrative embodiment.
Figure 89B:
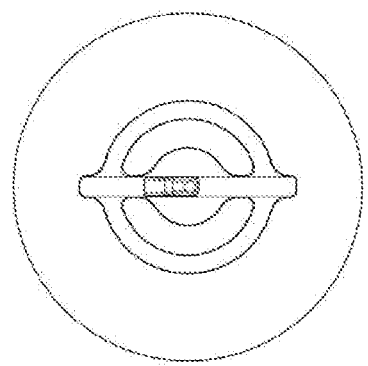
Figure 89C:
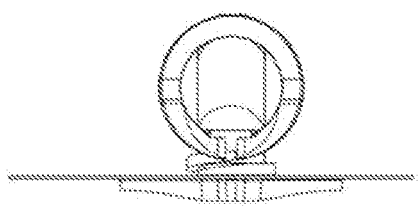
Figure 89D:
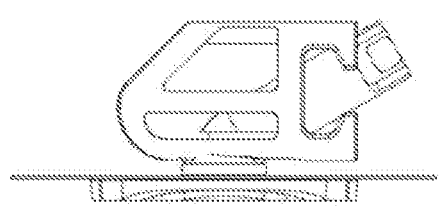
Figure 94A:
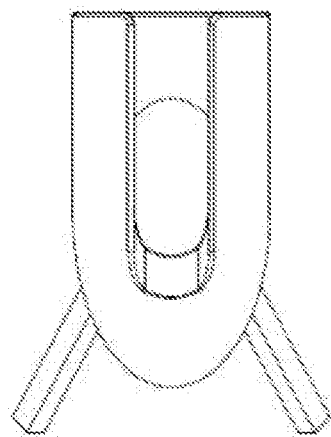
FIGS. 94A, 94B, 94C, and 94D are diagrams showing front, top, perspective and side views of an alternative embodiment of an extra-arterial shoe.
Figure 94B:
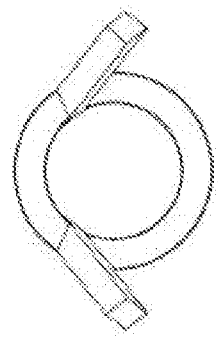
Figure 94C:
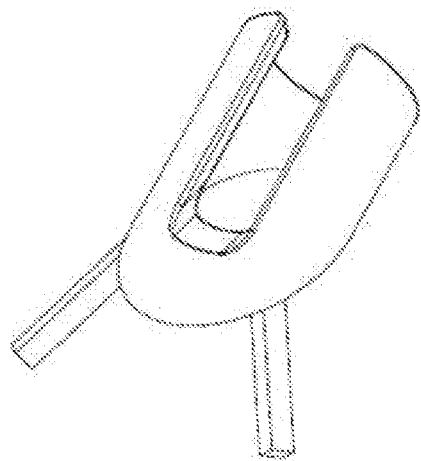
Figure 94D:
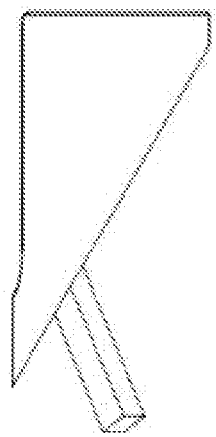
Figures 96A, 96B:
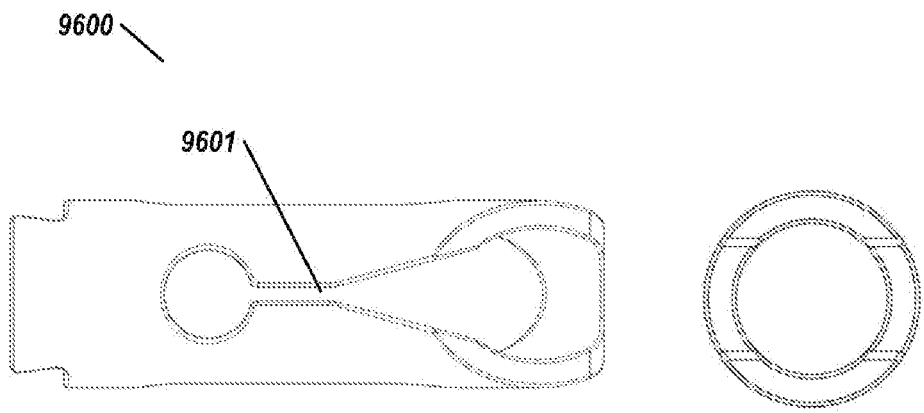
FIGS. 96A, 96B, 96C, and 96D are diagrams showing front, top, perspective and side views of an alternative embodiment of an extra-arterial shoe.
Figures 96C, 96D:
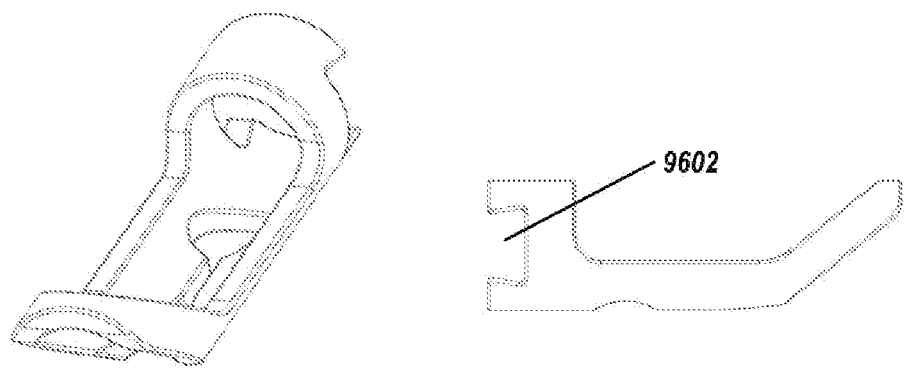
Figure 97A:
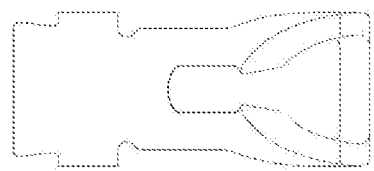
FIGS. 97A, 97B, 97C, and 97D are diagrams showing front, top, perspective and side views of an alternative embodiment of an extra-arterial shoe.
Figure 97B:
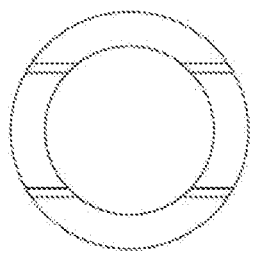
Figure 97C:
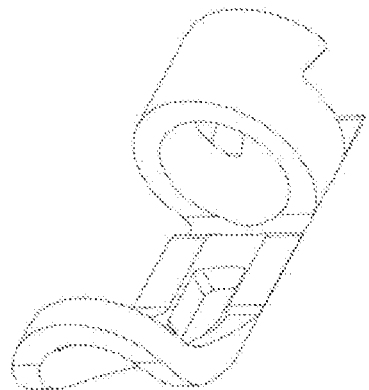
Figure 97D:
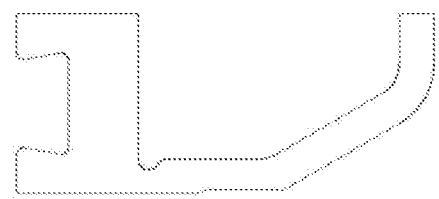

FIG. 84 shows the shoe 8101 deployed and engaged with tabbed support member 7401 via locking tabs 7402 after deployment of the implant according to an exemplary embodiment. In certain embodiments, locking tabs 7402 engage shoulders 8102 after deployment of the implant. F FIG. 85 shows the shoe 8101 deployed and engaged with tabbed support member 7401 after deployment of the implant according to an exemplary embodiment. In certain embodiments, one or more centering tabs (e.g., centering tab 7403) can engage the shoe (e.g., shoe 8101) via a matching shoe connector profile, e.g., shoe connector profile 8103. Alternative shapes and/or designs for the cage or shoe are envisioned, e.g., a shoe as shown in FIGS. 86A and 86B.

In some embodiments, the cage or shoe engages with the implant by engaging a locking neck, e.g., on column 122. FIG. 87 depicts an implant 8700 comprising a sealable member 106, a base 120, and a column 122 comprising a locking neck 8701.

FIG. 88 depicts a sample embodiment of the cage or shoe, e.g., shoe 8800 comprising an engagement slot 8801. In some embodiments, after deployment of the implant (e.g., implant 8700), the shoe (e.g., shoe 8800) is deployed, e.g., as described above, e.g., using a shoe pusher. In some embodiments, the shoe pusher pushes the shoe onto the engagement neck such that the engagement slot is splayed during the distal movement of the shoe. In its final engaged position, the shoe is engaged by snap-fitting the engagement slot with the locking neck, e.g., as depicted in FIG. 89. In some embodiments, a cage or shoe can have one or more engagement elements that engage the implant via engagement tabs and/or an engagement neck.

FIGS. 90-97 depict exemplary embodiments of the cage or shoe. In some embodiments, the cage or shoe has an aperture (e.g., a hole or a slot), e.g., to allow a pin (e.g., a locator pin), or a guard member (e.g., guard member 126) or other element to pass through the cage or shoe. In one exemplary embodiment shown in FIG. 90, the shoe 9000 comprises hole 9001 to allow a pin (e.g., a locator pin), or a guard member (e.g., guard member 126) or other element to pass through the cage or shoe. Exemplary shoe 9000 comprises a shoe connector element 9002, e.g., to connect the shoe to a shoe pusher or delivery shaft. Other embodiments of a similar configuration are shown in FIGS. 91 and 92.

In one exemplary embodiment shown in FIG. 93, the shoe 9300 comprises slot 9301, to allow a pin (e.g., a locator pin), or a guard member (e.g., guard member 126) or other element to pass through the cage or shoe. Exemplary shoe 9300 comprises a shoulder 9302. In some embodiments, a shoe or cage, e.g., shoe 9300, engages with a delivery element, e.g., a shoe pusher, via a shoulder, e.g., shoulder 9302. Another exemplary embodiment of a shoe as described herein is shown in FIG. 94.

In one exemplary embodiment shown in FIG. 95, the shoe 9500 comprises an engagement slot 9501. In certain embodiments, the engagement slot can have the shape of a circle, square, rectangular, triangle, rhombus and/or any combination or composition thereof. In certain embodiments, the shoe connector profile can have the shape of a key hole. In some embodiments, the shape of the engagement slot complements the shape of the engagement neck. In one exemplary embodiment shown in FIG. 96, the shoe 9600 comprising a narrow, key hole shaped engagement slot 9601 and a connector element 9602. Another exemplary embodiment of a shoe as described herein is shown in FIG. 97.

In some embodiments, the extra-arterial securing component (e.g., a cage or "shoe") comprises at least one material selected from the group consisting of Polydioxanone, Poly-L-lactide, Poly-D-lactide, Poly-DL-lactide, Polyglycolide, ε-Caprolactone, and Polyethylene glycol. In some embodiments, the material of the support member and/or sealable member is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

Although the present invention relating to extra-arterial securing component (e.g., a cage or "shoe") has been described with reference to particular examples and exemplary embodiments, it should be understood that the foregoing description is in no manner limiting.

Moreover, the features described herein may be used in any combination.

Example: Implant for Closing a Hollow Vessel

In some embodiments, the disclosed technology is an implant capable of closing holes in hollow vessels. The implant consists of three distinct parts: a flexible sealing member (e.g., wing), a pin, and a rigid support member (e.g., foot core). This implant may be attached to and packaged with a delivery system. A design is now described below, though other variants, as described herein, may be employed as viable designs to accomplish the same outcomes.

In an example embodiment, the foot core is designed to support the wing during assembly, delivery, and final deployment in the hollow vessel to provide a fast and secure closure of the access site hole. It comprises a flat base with an O-ring shape, two tabs in parallel axis to the foot core column, which protrude out from the perimeter of the O-ring, a threaded section, and recessed sections and through holes.

In some embodiments, the foot core is an integral part of the implant. It includes a hole from the bottom of the center of the O-ring section to the top of the column for guide wire access. It further includes a hole in the foot core column to hold the pin. It includes two recesses on the proximal tip of the column for engaging with the delivery system.

In some embodiments, the shapes of the two spokes in the O-ring are different. This serves the purpose of the larger rear spoke providing extra support (see, for example, FIGS. 4A and 4B) that helps to push the wing against the vessel luminal surface, thereby providing an improved seal. This rear spoke also provides additional security to the user, so that the implant is less likely to be accidently withdrawn fully out of the artery due to folding and/or deformation of the rear spoke. This in turn, provides enhanced tactile feedback to the user during deployment.

In some embodiments, the surface of a vessel lumen can be uneven and is not always uniformly smooth. The ability of the wings to form an effective seal against a vessels wall can be adversely affected if it has a very uneven topography. The rear spoke member, in some embodiments, pushes the wing against the vessel wall forcing the artery to conform to the wing. This creates a seal between the wing and the vessel surface in a variety of vessel surface topographies.

In some embodiments, the base of the O-Ring is flat, at rest, while the artery has a curvature. When the O-Ring implant is deployed into the artery, the flat foot core base adapts to the curvature of the artery and, in some embodiments, pushes the wing against the artery wall to form a contact between the flexible wing and artery inner luminal wall. This may directly enhance the effectiveness of the seal at the tamponade stage of the deployment as it does not rely on the user having to hold the device in a precise location.

In some embodiments, although the O-Ring foot core is constructed of a plastic material, its profile is thin enough to facilitate the "compression/folding" of the transverse sections and not damage itself or the flexible wing during pass through of the implant in the funnel into the loading cannula. The geometry of the foot core base allows the supporting members to fold down under the foot core as it is withdrawn through the loading funnel. The extra support member also keeps the wing in contact with the funnel internal surface during loading giving more consistent loading.

The O-ring foot core design and its variants provides, in some embodiments, support for the flexible wing portion of the implant throughout the life cycle of the implant from initial manufacturing when the implant is assembled through transportation and storage and ultimately during all stages of implant deployment into the hole in the hollow vessel for which it is intended to seal. The O-ring foot core provides, in some embodiments, structural support for the flexible wing when the device is fully assembled in its storage tray. During deployment to close a hole in a hollow vessel, the implant is loaded into a cannula through a loading funnel which reduces the cross-sectional area of the implant (O-ring and flexible wing) to make it possible to deliver the implant through an introducer catheter into a hollow vessel (such as an artery or a vein) within which there had been made an access hole to perform a minimally invasive procedure. During this delivery and deployment of the implant, in certain embodiments, the O-ring foot core supports the wing.

Uses can include closing access site holes in hollow vessels; closing access site holes in blood vessels; closing holes in arteries; closing small and large holes up to 30 F in hollow vessels; closing access site holes in the abdominal post endoscopic procedures; and closing access site holes in the femoral artery, subclavian artery, ascending aorta, axillary and brachial arteries.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Some embodiments of the present invention are directed to a closure system, device, and method of percutaneous closure of an arteriotomy following endovascular/intra S arterial procedures.

Although the present invention has been described with reference to particular examples and exemplary embodiments, it should be understood that the foregoing description is in no manner limiting. Moreover, the features described herein may be used in any combination.

In certain embodiments, the invention is used for closing access site holes in blood vessels or arteries, for example, but not limited to, the femoral artery, subclavian artery, ascending aorta, axillary and brachial arteries.

In certain embodiments, the invention is used for closing access site holes in the abdominal post endoscopic procedures.

In certain embodiments, the invention is used for closing access site holes in hollow vessels. The size of the site holes may be up to 30 French (F) in certain embodiments.

Experimental Data

The provided technologies were tested in vitro and in vivo. For the in vitro test, the sealable member was tested on a test bench using either a flexible tube or a bovine artery to simulate the body lumen. The bovine artery has an inner diameter between 7.8 mm and 9 mm and a wall thickness between 1.4 and 1.9 mm. The flexible tube has an inner diameter of 7.1 mm and a wall thickness of 0.55 mm. In each of the flexible tube and the bovine artery, an aperture was created with a diameter of 6 and 8 mm respectively. A deployment sheath (e.g., the delivery cannula), used in the procedure, has an inner/outer diameter of 20 F/24 F.

The test was performed with water flowing through each of the respective bovine artery and flexible tube, under physiological conditions with a pulse of approximately 60 hertz, a systolic pressure of about 120 mm-Hg, and a diastolic pressure of about 80 mm-Hg. Ten data samples were collected for each test. The amount of water leaked within 5 minutes from the time of deployment is measured and provided in Table 4 and Table 5 below.

TABLE 4

Bovine artery: in vitro test comparison of devices, including
(i) a baseline closure device having a rigid base core
and a flexible sealable member (see "Current Device
R#1") and (ii) a closure device configured with
a flexible support base and a flexible sealable member
(e.g., comprising a mesh layer and substrate) (see "New Device R#2").

| Total leak in 5 ml (ml) | Current Device R#1 | New Device R#2 |
|---|---|---|
| Mean | 5.2 | 0.9 |
| SD | 4.2 | 0.7 |
| Min | 0.8 | 0.0 |
| Max | 12 | 2.0 |

TABLE 5

Flexible tube: in vitro test comparison of devices, including
(i) the same baseline closure device having a rigid base core
and a flexible sealable member (see "Current Device R#1") and
(ii) the same closure device configured with a flexible support
base and a flexible sealable member (e.g., comprising a mesh
layer and substrate) (see "New Device R#2").

| Total leak in 5 ml (ml) | Current Device R#1 | New Device R#2 |
|---|---|---|
| Mean | 13.6 | 1.8 |
| SD | 12.0 | 1.2 |
| Min | 0 | 0.6 |
| Max | 16 | 4.1 |

The test illustrates a 5× improvement of the closure device, configured with a flexible support member and a flexible sealable member (e.g., comprising the mesh layer and substrate), in reducing the amount of fluid leakage over the design employing a sealable with no mesh layer (and having a rigid core). In addition to the seal formed from the R #2 closure device having improved leakage performance, as shown in the plots of the histograms and the standard deviation values of the tables, a more consistent closure is also provided.

For the in vivo test, the sealable member was tested in animal subjects. A similar 6 mm puncture was made in a pig aorta. The deployment sheath, used in the procedure, also has an inner/outer diameter of 20 F/24 F. Six data samples were collected for each test using the R #1 design and the R #2 design. The total deployment time, tamponade time, time to hemostasis, and total procedure time are provided in Table 6 below.

TABLE 6

Pig Aorta: in vivo study comparison of devices, including (i) the
same baseline closure device having a rigid base core and a flexible
sealable member (see "R#1") and (ii) the same closure
device configured with a flexible support base and a flexible sealable
member (e.g., comprising the mesh layer and substrate) (see "R#2").

| n = 6 | Deployment Time (mm:ss) (Inc TT) | Tamponade Time (TT) (mm:ss) | Time to Hemostasis (TTH) (mm:ss) | Total Procedure Time (mm:ss) | ACT (sec) |
|---|---|---|---|---|---|
| R#1 in vivo study ||||||
| Average | 07:01 | 04:08 | 05:49 | 12:50 | 190 |
| Max | 07:45 | 04:30 | 30:15 | 37:38 | 217 |
| Min | 06:24 | 04:00 | 00:00 | 07:00 | 165 |
| R#2 in vivo study ||||||
| Average | 02:50 | 00:57 | 00:38 | 03:29 | 294 |
| Max | 03:07 | 01:37 | 01:30 | 04:30 | 404 |
| Min | 02:15 | 00:20 | 00:00 | 02:15 | 194 |

As shown in Table 6, the R #2 design improves the total deployment time by 2.5× over the R #1 design. The total deployment time, used in the observations, includes the time for the device to be positioned and deployed in the pig aorta and for the leakage to stop.

In addition, the R #2 design improves the time to hemostasis by 9× over the R #1 design. The time to hemostasis (TTH), used in the observations, refers to the time from which a seal is created and the time for leakage to stop. Less variability in the time to hemostasis is also observed.

In addition, the R #2 design reduces the overall closure procedure time by 3.7× over the R #1 design. The activated clotting time (ACT time) was longer by over 100 seconds. The activated clotting time refers to the time for whole blood to clot upon exposure to an activator.

Although the present invention has been described with reference to particular examples and exemplary embodiments, it should be understood that the foregoing description is in no manner limiting. Moreover, the features described herein may be used in any combination.

What is claimed is:

1. A device for sealing an aperture in a tissue of a body lumen comprising:
   a closure device comprising:
   (i) a flexible support member comprising a base and a column disposed in the center of the base, the column comprising a centering tab and/or one or more locking tabs;
   (ii) a sealable member comprising a thin, flexible sheet, a hole in the center of the flexible sheet, wherein the flexible sheet is disposed over the base, and wherein the column passes through the hole;
   (iii) an extra-arterial shoe comprising one or more engagement elements for engagement with an exterior of the column to secure the closure device; and
   (iv) a guard member comprising an elongate body, a locking feature, a wedge feature, and a guidewire lumen, wherein the elongate body of the guard member is inserted through a first aperture of the extra-arterial shoe; and a delivery system comprising a delivery shaft,
  wherein the extra-arterial shoe comprises a hollow cylindrical shape and a centerline configured to be collinear with a centerline of the column of the support member when the extra-arterial shoe is engaged on the column,
  wherein the longitudinal axis of the column forms an angle between 10 degrees and 70 degrees with a lateral plane of the base,
  wherein the column is angled over a proximal end of the base, and
  wherein the one or more engagement elements of the extra-arterial shoe comprises at least one of a notch, a hole, and a groove.

2. The device of claim 1, wherein the entirety of the extra-arterial shoe is disposed between a first radius around the centerline of the extra-arterial shoe and a second radius around the centerline of the extra-arterial shoe, wherein the second radius is larger than the first radius.

3. The device of claim 2, wherein the first radius is large enough to allow the column to be disposed therethrough when the extra-arterial shoe is engaged with the column.

4. The device of claim 1, wherein a body of the extra-arterial shoe is disposed between a first radius around the centerline of the extra-arterial shoe and a second radius around the centerline of the extra-arterial shoe, wherein the second radius is larger than the first radius.

5. The device of claim 4, the extra-arterial shoe further comprising at least one angled prong extending externally away at an angle from the body of the extra-arterial shoe beyond the second radius, wherein the at least one angled prong is attached to the distal end of the body of the extra-arterial shoe, and wherein the distal tip of the at least one angled prong exerts pressure against an exterior surface of the body lumen when the extra-arterial shoe is engaged with the column.

6. The device of claim 5, wherein the extra-arterial shoe comprises 2, 3, 4, 5, or 6 angled prongs spaced around the centerline of the extra-arterial shoe at about 180, 120, 90, 72, or 60 degrees apart, respectively.

7. The device of claim 1, wherein the extra-arterial shoe comprises at least one material selected from the group consisting of ε-Caprolactone and Polyethylene glycol.

8. The device of claim 1, further comprising a shoe pusher, wherein the shoe pusher is mounted on the delivery shaft and is slideably moveable along a longitudinal axis of the delivery shaft, and wherein the shoe pusher is configured to push the extra-arterial shoe distally toward the flexible support member.

9. The device of claim 1, wherein the base comprises a generally circular planar shape and one or more lateral support portions forming a continuous outer ring structure at the circumference of the circular planar shape, wherein the outer ring structure is connected to the center of the base by at least one radial spoke.

10. The device of claim 9, wherein the base comprises at least one space between the one or more lateral support portions and the center of the base.

11. The device of claim 10, wherein the one or more lateral support portions comprise at least one gap, wherein the at least one gap forms a discontinuity in the outer ring structure of the base.

12. The device of claim 11, wherein the one or more lateral support portions comprise two gaps spaced about 180 degrees apart on lateral sides of the base, wherein the two gaps form two discontinuities in the outer ring structure of the base.

13. The device of claim 11, wherein the one or more lateral support portions comprise two pairs of gaps comprising a first pair of gaps disposed at a distal end of the base and a second pair of gaps disposed at a proximal end of the base, the first pair and the second pair spaced about 180 degrees apart, and wherein the two pairs of gaps form discontinuities in the outer ring structure of the base.

14. The device of claim 13, wherein the base comprises:
  an anterior region extending distally from a distal end of the base outside the outer ring structure, the anterior region disposed between the first pair of gaps; and
  a posterior region extending proximally from a proximal end of the base outside the outer ring structure, the posterior region disposed between the second pair of gaps.

15. The device of claim 1, wherein the first aperture is located on the cylindrical body of the extra-arterial shoe.

16. The device of claim 1, wherein the flexible support member further comprises a second aperture located on the column and a channel disposed through the center of the column, and wherein the channel runs between a bottom surface of the base and a top surface of the column.

17. The device of claim 1, wherein the first aperture overlaps with the second aperture when the extra-arterial shoe is engaged with the column, wherein the guard member is inserted through the channel of the column, and passes through the second aperture and through the first aperture, and wherein the wedge feature closes the channel.

18. The device of claim 1, wherein the extra-arterial shoe further comprises a shoe connector element to connect the shoe to the shoe pusher or to the delivery shaft.

19. The device of claim 1, wherein the body lumen comprises the inside space of a vein or an artery.

20. The device of claim 1, wherein the column comprises a threaded portion near the base of the column to load the sealable member, wherein the threaded portion comprises a protrusion that encircles the body of the column, and wherein the protrusion comprises a gap in the protrusion.

* * * * *